US012790289B2

(12) United States Patent
Zhang et al.

(10) Patent No.: US 12,790,289 B2
(45) Date of Patent: Nov. 10, 2026

(54) LIPID COMPOUND AND THE COMPOSITION THEREOF

(71) Applicant: GUANGZHOU RIBOBIO CO., LTD, Guangzhou (CN)

(72) Inventors: Bill Biliang Zhang, Guangzhou (CN); Haoting Zhao, Guangzhou (CN); Jain Wen, Guangzhou (CN)

(73) Assignee: GUANGZHOU RIBOBIO CO., LTD, Guangzhou (CN)

( * ) Notice: Subject to any disclaimer, the term of this patent is extended or adjusted under 35 U.S.C. 154(b) by 619 days.

(21) Appl. No.: 17/622,649

(22) PCT Filed: May 27, 2021

(86) PCT No.: PCT/IB2021/054662
§ 371 (c)(1),
(2) Date: Dec. 23, 2021

(87) PCT Pub. No.: WO2022/112855
PCT Pub. Date: Jun. 2, 2022

(65) Prior Publication Data

US 2023/0242474 A1 Aug. 3, 2023

(30) Foreign Application Priority Data

Nov. 27, 2020 (CN) ......................... 202011355845.4
Mar. 31, 2021 (WO) .................. PCT/IB2021/052705

(51) Int. Cl.

| | |
|---|---|
| ***C07C 229/16*** | (2006.01) |
| ***A61K 9/00*** | (2006.01) |
| ***A61K 9/51*** | (2006.01) |
| ***A61K 47/54*** | (2017.01) |
| ***A61K 47/62*** | (2017.01) |
| ***C07C 229/12*** | (2006.01) |

(52) U.S. Cl.
CPC .......... *C07C 229/16* (2013.01); *A61K 9/0019* (2013.01); *A61K 9/5123* (2013.01); *A61K 9/5146* (2013.01); *A61K 47/549* (2017.08); *A61K 47/62* (2017.08); *C07C 229/12* (2013.01)

(58) Field of Classification Search
CPC ............................ A61K 9/5123; A61K 9/0019
See application file for complete search history.

(56) References Cited

U.S. PATENT DOCUMENTS

| | | | |
|---|---|---|---|
| 10,106,490 | B2 | 10/2018 | Du |
| 10,166,298 | B2 | 1/2019 | Ansell et al. |
| 10,730,924 | B2 | 8/2020 | Ticho et al. |
| 2005/0208015 | A1 | 9/2005 | Nemoto et al. |
| 2015/0376115 | A1 | 12/2015 | Ansell et al. |
| 2017/0119904 | A1 | 5/2017 | Ansell et al. |
| 2020/0368173 | A1 | 11/2020 | Hatanak et al. |

FOREIGN PATENT DOCUMENTS

| | | | | |
|---|---|---|---|---|
| CN | 106795096 A | 5/2017 | | |
| CN | 108368028 A | 8/2018 | | |
| CN | 109640962 A | 4/2019 | | |
| TW | 201713614 A | 4/2017 | | |
| WO | WO-2010144740 A1 | 12/2010 | | |
| WO | WO-2013016058 A1 | 1/2013 | | |
| WO | WO-2014210356 A1 | 12/2014 | | |
| WO | WO-2016176330 A1 | 11/2016 | | |
| WO | WO-2016210190 A1 | 12/2016 | | |
| WO | WO-2017049245 A2 * | 3/2017 | ......... | A61K 31/7105 |
| WO | WO-2017075531 A1 | 5/2017 | | |
| WO | WO-2017201340 A2 | 11/2017 | | |
| WO | WO-2018232357 A1 | 12/2018 | | |
| WO | WO-2020061284 A1 | 3/2020 | | |
| WO | WO-2020061295 A1 | 3/2020 | | |
| WO | WO-2020061367 A1 | 3/2020 | | |
| WO | WO-2021155274 A1 | 8/2021 | | |
| WO | WO-2022112855 A1 | 6/2022 | | |

OTHER PUBLICATIONS

Anonymous, CAS Registry No. 856078-46-1, ACS, Jul. 20, 2005 (Year: 2005).*
Berge, S.M., et al., "Pharmaceutical Salts," J Pharm. Sci. 66:1-19, Elsevier, Netherlands (Jan. 1977).
International Search Report and Written Opinion for International Application No. PCT/IB2021/054662, National Intellectual Property Administration, China, mailed on Sep. 9, 2021, 13 pages.
Ramishetti, S. et al., "A Combinatorial Library of Lipid Nanoparticles for RNA Delivery to Leukocytes" Advanced Materials, Jan. 30, 2020, 32(12): 1906128 (1 to 8).

* cited by examiner

*Primary Examiner* — Craig D Ricci
*Assistant Examiner* — Paul Hoerner
(74) *Attorney, Agent, or Firm* — Sterne, Kessler, Goldstein & Fox P.L.L.C.

(57) ABSTRACT

The invention relates to a lipid compound of formula (I), including lipid nanoparticles thereof, and the manufacturing method and the use of pharmaceutical delivery. The lipid compounds have formula (I):

(I)

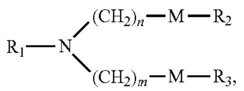

or a salt or an isomer thereof, wherein $R_1$, $R_2$, $R_3$ n and m are defined herein.

16 Claims, 3 Drawing Sheets

LIPID COMPOUND AND THE COMPOSITION THEREOF

TECHNICAL FIELD

The invention belongs to the field of biomedicine and biotechnology, and relates to a series of lipid compounds and therapeutic pharmaceutical delivery systems thereof.

BACKGROUND

Exogenous biomolecules and some pharmaceutical molecules are hard to reach the cytoplasm though the cell membrane for curing effect. mRNA is one kind of biomolecule with negative charge, which has to overcome the barrier of cell membrane, for translating to protein and playing the biological function. Thus, delivering the biomolecules efficiently in vivo is an important challenge.

Lipid Nanoparticle (LNP) is one kind of new nucleic molecule delivery technology, which typically includes four components: (1) ionizable lipid, which combines with mRNA into a particle as large as bacteria, and releases mRNA from endosome to cytoplasm; (2) PEG-lipid, which improves the half-life of LNPs in blood; (3) cholesterol, which improves the stability of nanoparticles; (4), phospholipid, which is beneficial to form the double lipid structure (lipid bilayer). LNPs function to not only protect the mRNA from being decomposed by RNA enzyme (RNAses) or recognized by TLRs, but to also avoid the over-reaction of the innate immune system. The ionizable lipid can accelerate the cell uptake, and help the pharmaceutical molecules to release from endosome, achieving therapeutic effect.

The first LNP-siRNA medicine encapsulated by MC3 cationic lipid has been approved for marketing, proving that LNP can deliver the nucleic acid pharmaceuticals effectively in vivo, with an acceptable safety profile to some extent. In recent years, the study found that LNP also showed great application potential in the field of mRNA pharmaceutical and vaccine. The development direction of LNP delivery system is mainly focused on the ionizable lipid, the formula thereof and how to overcome the toxicity of some lipid preparations.

PCT/US2016/052352, published as WO2017/049245, discloses compounds and compositions and their use for intracellular delivery of therapeutic agents, including several novel lipid structures which can deliver the mRNA molecule to the target cell. PCT/US2010/038224, published as WO2010/144740 discloses the chemical structure of MC3 which can encapsulate the siRNA pharmaceuticals with high efficiency, and avoid decomposition and removal during the delivery. Currently, the LNP delivery system is considered as a key technology for promoting nucleic acid pharmaceuticals into therapeutic application.

SUMMARY OF THE DISCLOSURE

For the current technical question, it was necessary to discover novel ionizablelipid compounds to improve the delivery efficiency and lower the toxicity of nucleic acid pharmaceuticals, such as mRNA and siRNA. The disclosure provides a series of novel ionizable lipid compounds which form the aliphatic chain by ester group of glycerol and ether group. The delivery effects of such lipids are better than the ionizable lipid of aliphatic chain. The novel ionizable lipids are combined with other lipid ingredients and formed into lipid nanoparticles which deliver mRNA or other pharmaceutical agents effectively in vivo where the intended biological function occurs. For example, delivering siRNA into a cell plays a role in gene silencing therapy; delivering mRNA into a cell can translate to protein or antigen efficiently for vaccine or pharmaceutical therapy; delivering antibody in vivo plays a role in therapy; and delivering Cas 9 mRNA in vivo plays a role in gene editing.

DETAILED DESCRIPTION

Figure 1:
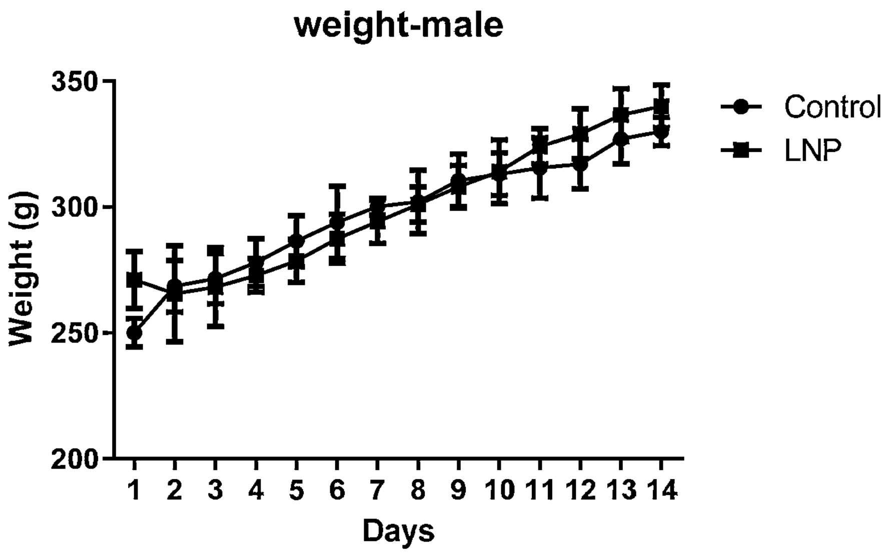
FIG. 1 is a graph depicting the weight change of male rat in LNP safety evaluation.

The disclosure provides a series of novel ionizable lipids, synthesis methods thereof, and pharmaceutical molecules mixed and encapsulated by a mixture comprising ionizable lipid, PEG lipid, structural lipid (such as, cholesterol) and phospholipid, thereby forming a nanoparticle delivery system which can used for in vitro cell delivery and in vivo organ targeted cell delivery.

In one embodiment, the disclosure relates to a compound of the following formula (I):

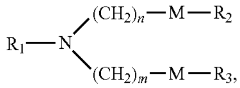

(I)

wherein $R_1$ is selected from —$R_1$'—X, $R_1$' is —$(CH_2)_{0-6}$—, and X is amino, hydroxyl, ethynyl, cyano, —$C(O)(CH_2)_{1-3}NR_aR_b$, —$C(O)O(CH_2)_{1-3}NR_aR_b$, —$OC(O)(CH_2)_{1-3}NR_aR_b$, —$C(O)NH(CH_2)_{1-3}NR_aR_b$, —$NHC(O)(CH_2)_{1-3}NR_aR_b$, —$NHC(O)CH(NR_aR_b)(CH_2)_{1-3}NR_aR_b$, $C_{3-7}$ cycloalkyl, 4-7 membered heterocyclic group, $C_{6-10}$ aryl or 5-10 membered heteroaryl, the said cycloalkyl, heterocyclic group, aryl or heteroaryl are optionally substituted by the following groups: —$(CH_2)_{1-3}OH$, —$(CH_2)_{1-3}NR_aR_b$, —$(CH_2)_{1-3}C(O)NR_aR_b$; or X can also be:

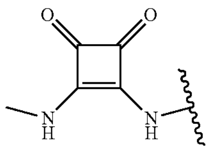

or

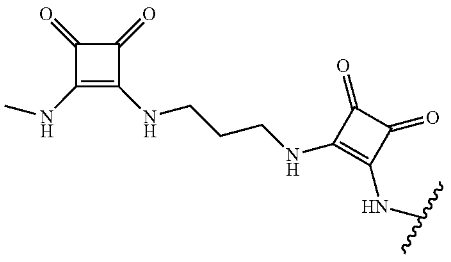

$R_a$, and $R_b$ are independently selected from H, $C_{1-3}$ alkyl, $-(CH_2)_{1-3}NH_2$, $-(CH_2)_{1-3}NH(CH_2)_{1-3}NH_2$; or Ra and Rb together with the nitrogen to which they are connected form a 5-10 membered heterocycle that includes 1-3 heteroatoms selected from N, O or S, said heterocycle is optionally substituted by the following groups: $C_{1-6}$ alkyl, $C_{1-6}$ alkyl halide, $C_{1-6}$ alkyl hydroxyl group and $C_{1-6}$ alkyl amino group;

$R_2$, and $R_3$ are independently selected from H, $C_{2-18}$ alkyl, $C_{4-18}$ alkenyl or

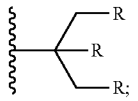

each M is independently selected from $-CH_2-$, $-CH{=}CH-$, $-NH-$, $-C(O)-$, $-C(O)O-$, $-OC(O)-$, $-C(O)NH-$, or $-NHC(O)-$;

each R is independently selected from H, R', —OR* or —R"OR*;

each R' is independently selected from $C_{1-10}$ alkyl or $C_{3-12}$ alkenyl;

each R" is independently selected from $C_{1-10}$ alkyl or $C_{3-12}$ alkenyl;

each R* is independently selected from $C_{1-10}$ alkyl or $C_{3-12}$ alkenyl;

n, and m are independently an integer independently selected from 1 through 9;

or a salt or an isomer thereof.

In one embodiment, the ionizable lipid is a compound of formula (I), wherein:

R' is $-(CH_2)_{2-3}-$, and X is hydroxyl, $-C(O)(CH_2)_{2-3}NR_aR_b$, $-C(O)O(CH_2)_{2-3}NR_aR_b$, $-C(O)NH(CH_2)_{2-3}NR_aR_b$, or 5-10 heteroaryl which is optionally substituted by one or more of the following groups: $-(CH_2)_{2-3}OH$, $-(CH_2)_{2-3}NR_aR_b$, $-(CH_2)_{2-3}C(O)NR_aR_b$; or X can also be:

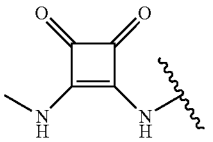

or

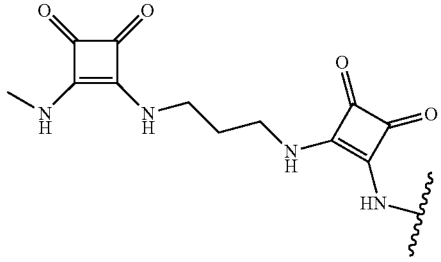

;

$R_a$, and $R_b$ are independently selected from H, $C_{1-3}$ alkyl, $-(CH_2)_{2-3}NH_2$, $-(CH_2)_{2-3}NH(CH_2)_{2-3}NH_2$; or the 5-10 membered heterocycle including 1-3 heteroatoms selected from N or O, which is formed together by $R_a$, $R_b$ and their connected nitrogen, the said heterocycle is optionally substituted by the one or more of the following groups: $C_{1-6}$ alkyl, $C_{1-6}$ alkyl halide, $C_{1-6}$ alkyl hydroxyl group and $C_{1-6}$ alkyl amino group.

In one embodiment, the ionizable lipid is a compound of formula (I), wherein:

each M is independently selected from $-CH_2-$, $-CH{=}CH-$, $-C(O)O-$, $-OC(O)-$, $-C(O)NH-$, or $-NHC(O)-$.

In one embodiment, the compound of formula (I) is a compound of formula (II):

(II)

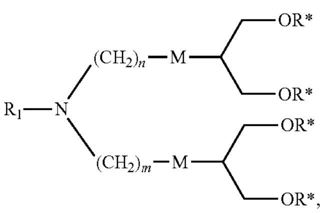

wherein:

each R* is independently selected from $C_{2-10}$ alkyl, preferably $C_{6-10}$ alkyl, preferably $C_6$ alkyl.

In one embodiment, the ionizable lipid is a compound of formula (II), wherein:

each M is independently selected from $-C(O)O-$ or $-OC(O)-$, preferably $-C(O)O-$.

In one embodiment, the ionizable lipid is a compound of formula (II), wherein:

$R_1$ is selected from $-R_1'-X$, $R_1'$ is $-(CH_2)_{1-6}-$, and X is hydroxyl.

In one embodiment, the ionizable lipid is a compound of formula (II), wherein:

$R_1$ is selected from $-R_1'-X$, $R_1'$ is $-(CH_2)_{1-6}-$, and X is $-C(O)(CH_2)_{2-3}NR_aR_b$, $-C(O)O(CH_2)_{2-3}NR_aR_b$, $-C(O)NH(CH_2)_{2-3}NR_aR_b$, $R_a$. and $R_b$ are independently selected from H, $C_{1-3}$ alkyl, $-(CH_2)_{2-3}NH_2$; or 5-10 membered heterocycle containing 1-3 heteroatoms selected from N or O, which is formed together by $R_a$, and $R_b$ and their connected nitrogen atom, preferably morpholinyl or piperidinyl, the said heterocycle is optionally substituted by $C_{1-6}$ alkyl hydroxyl.

In one embodiment, the ionizable lipid is a compound of formula (II), wherein:

$R_1$ is selected from $-R_1'-X$, $R_1'$ is $-(CH_2)_{1-6}-$, X is 5-6 membered heteroaromatic group, preferably triazolyl, said heteroaromatic group is optionally substituted by one or more of the following groups: $-(CH_2)_{2-3}OH$, $-(CH_2)_{2-3}NR_aR_b$, and $-(CH_2)_{2-3}C(O)NR_aR_b$, $R_a$, and $R_b$ are independently selected from H, $C_{1-3}$ alkyl, $-(CH_2)_{2-3}NH_2$, $-(CH_2)_{2-3}NH(CH_2)_{2-3}NH_2$, or 5-10 membered heterocycle containing 1-3 heteroatoms selected from N or O, which is formed together by $R_a$, and $R_b$ and their connected nitrogen atom, preferably morpholinyl, piperazinyl or piperidinyl, the said heterocycle is optionally substituted by one or more of the following groups: $C_{1-6}$ alkyl, and hydroxyl.

In one embodiment, the ionizable lipid is a compound of formula (II), wherein:

$R_1$ is selected from $-R_1'-X$, $R_1'$ is $-(CH_2)_{1-6}-$, and X is

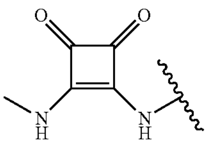

or

-continued

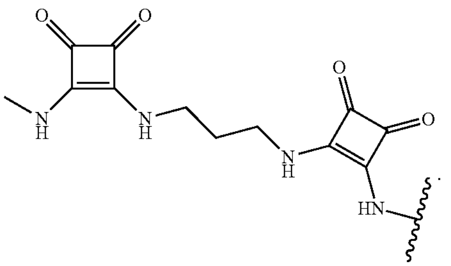

In one embodiment, the ionizable lipid is a compound of formula (II), wherein:

each n is 7, m is 7.

In one embodiment, the compound of formula (I) is a compound of formula (III):

(III)

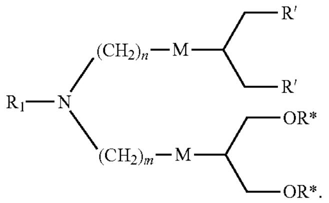

In one embodiment, the ionizable lipid is a compound of formula (III), wherein:

each R' is independently selected from $C_{1-10}$ alkyl, preferably $C_{2-8}$ alkyl.

In one embodiment, the ionizable lipid is a compound of formula (III), wherein:

each M is independently selected from —C(O)O— or —OC(O)—, preferably —C(O)O—.

In one embodiment, the ionizable lipid is a compound of formula (I) is compound of formula (IV):

(IV)

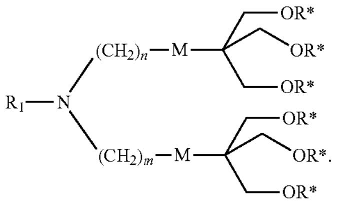

In one embodiment, the ionizable lipid is a compound of formula (IV), wherein:

each R* is independently selected from $C_{2-10}$ alkyl, preferably $C_{6-10}$ alkyl, preferably $C_6$ alkyl.

In one embodiment, the ionizable lipid is a compound of formula (IV), wherein:

each M is independently selected from —C(O)O— or —OC(O)—, preferably —C(O)O—.

In one embodiment, the ionizable lipid is a compound of formula (I) is a compound of formula (V):

(V)

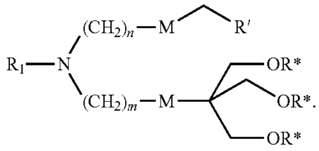

In one embodiment, the ionizable lipid is a compound of formula (V), wherein:

each R* is independently selected from $C_{2-10}$ alkyl, preferably $C_{6-10}$ alkyl, preferably $C_6$ alkyl.

In one embodiment, the ionizable lipid is a compound of formula (V), wherein:

each M is independently selected from —CH═CH—, —C(O)O— or —OC(O)—, preferably —CH═CH— or —C(O)O—.

In one embodiment, the ionizable lipid is a compound of formula (V), wherein:

each R' is independently selected from $C_{1-10}$ alkyl or $C_{3-12}$ alkenyl, preferably $C_{10}$ alkyl or $C_8$ alkenyl.

In another embodiment, the compound is a salt of any of the prior embodiments.

In another embodiment, the compound is a stereoisomer of any of the prior embodiments.

In one embodiment, the said compound is selected from the following compounds, salts or stereoisomers thereof: A1, A5, A6, A7, A9, A10, A11, A12, A13, A15, A16, A17, A18, A19, A20, A21, A22, A23, A24, A25, A26, A27, A28, A29, A30, A31, A32, A34, A35, A36, A37, A38, A39, A40, A41, A42, A43, A44, A45, A46, A47, and 48.

In one embodiment, the disclosure related to a composition comprising a ionizable lipid compound according to the claim 1, in admixture with a PEG lipid, a structural lipid and a phospholipid.

In one embodiment, the phospholipids are selected from at least any one of the following groups: 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-0-octadecenyl-5«-glycero-3-phosphocholine (18:0 Diether PC), 1-oleoyl-2-cholesterylhemisuccinoyl-5«-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanol amine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamin, 1,2-dioleoyl-sn-glycero phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidyethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE). One or more of the recited phospholipids can be used in the mixture.

In one embodiment, the PEG lipid is selected from at least any one of the following groups: PEG-modified phosphatidylethanolamine, PEG-modified phosphatidic acid, PEG-modified ceramide, PEG-modified dialkylamine, PEG-modified diacylglycerol, PEG-modified dialkylglycerol. One or more PEG lipids can be used in the mixture.

In one embodiment, the structural lipid is selected from at least any one of the following groups: cholesterol, fecosterol, sitosterol, ergosterol, campesterol, stigmasterol, brassicasterol, tomatidine, ursolic acid, alpha-tocopherol. One or more structural lipids can be used in the mixture.

In one embodiment, in the composition, ionizable lipid compound is from 20% to 80%, PEG lipid is from 1% to 10%, structural lipid is from 10% to 50% and phospholipid is from 5% to 30%, each of these percentages being calculated based on mole percentage of all lipids in the composition. In another embodiment, ionizable lipid compound is 20%, 25%, 30%, 35%, 40%, 45%, 50%, 55%, 60%, 65%, 70%, 75%, or 80%, calculated based on mole percentage of all lipids in the composition. In another embodiment, PEG lipid is 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%, calculated based on mole percentage of all lipids in the composition. In another embodiment, structural lipid is 10%, 15%, 20%, 25%, 30%, 35%, 40%, 45%, or 50%, calculated based on mole percentage of all lipids in the composition. In another embodiment, phospholipid is 5%, 10%, 15%, 20%, 25%, or 30%, calculated based on mole percentage of all lipids in the composition.

In one embodiment, the composition is in the form of a lipid nanoparticle.

In another embodiment, the lipid nanoparticle also comprises active ingredient. The active ingredient can be selected from at least any one of: DNA, RNA, protein, or an active pharmaceutical molecule.

In one embodiment, the RNA is selected from at least any one of: mRNA, siRNA, aiRNA, miRNA, dsRNA, aRNA, lncRNA, antisense nucleotide (ASO) or oligonucleotide.

In one embodiment, the protein is selected from at least any one of: antibody, enzyme, recombinant protein, polypeptide and short chain polypeptide.

The disclosure also relates to a method of producing lipid nanoparticles, comprising step (1): mixing the ionizable lipid compound, a PEG lipid, a structural lipid and a phospholipid in ethanol to form a lipid mixture.

The method may further comprise step (2): mixing the lipid mixture with an active ingredient to form lipid nanoparticle by mixer.

In one embodiment, the ionizable lipid compound, PEG lipid or PEG modified lipid, structural lipid and phospholipid are dissolved and mixed in ethanol, then mixed with an active ingredient by mixer to form lipid nanoparticle.

In one embodiment, the disclosure relates to an ionizable compound for use in the production of lipid nanoparticle.

In one embodiment, the lipid nanoparticle is neutral and uncharged in a neutral medium, and is positively charged after being protonated in an acidic medium.

In one embodiment, the lipid nanoparticle is as defined in the specification.

In one embodiment, disclosed is a pharmaceutical composition comprising the lipid nanoparticle and a pharmaceutically acceptable carrier.

In one embodiment, the disclosure relates to the lipid nanoparticle or a pharmaceutical composition thereof for use in the production of medicine.

In one embodiment, the medicine also comprises an active ingredient, wherein the active ingredient comprises at least any one of DNA, RNA, protein, and an active pharmaceutical molecule.

In one embodiment, the RNA is selected from at least any one of: mRNA, siRNA, aiRNA, miRNA, dsRNA, aRNA, and lncRNA.

In one embodiment, the invention relates to the lipid nanoparticle for use in the production of medicine, encapsulating an active ingredient into the said lipid nanoparticle.

In one embodiment, the invention relates to the use of medicine, the medicine can be applied to a human by intravenous injection, intramuscular injection, subcutaneous injection, microneedle patch, oral administration, oral and nasal spray, or painting.

The structures of representative ionizable lipid compounds of the disclosure are shown as follows:

A1

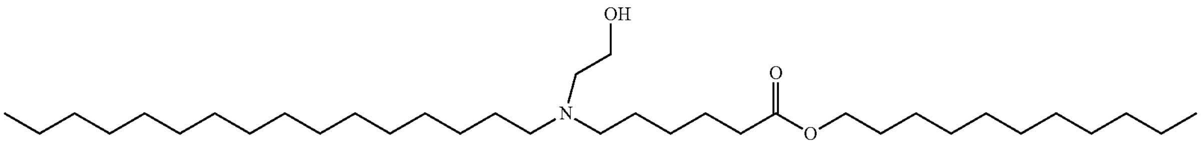

A5

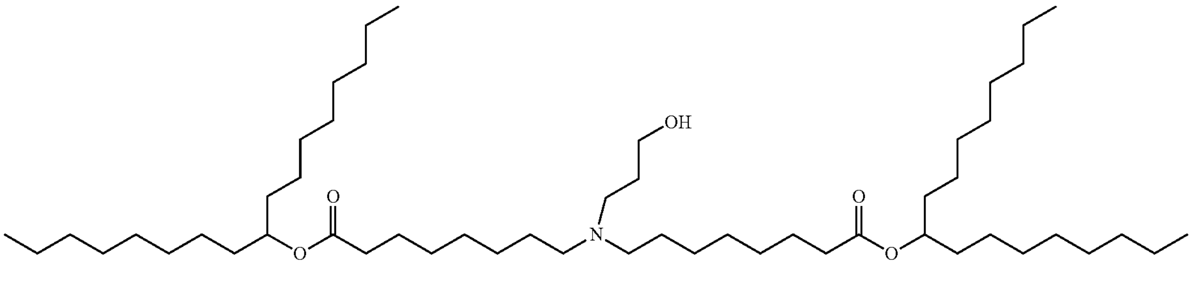

-continued
A6
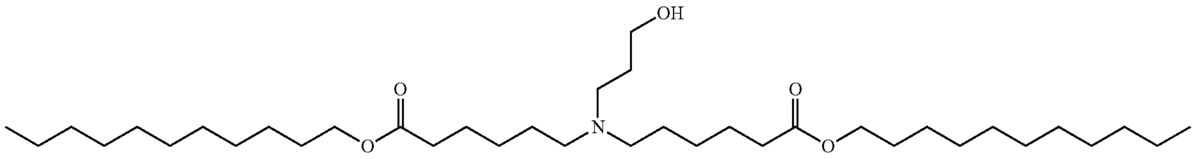
A7
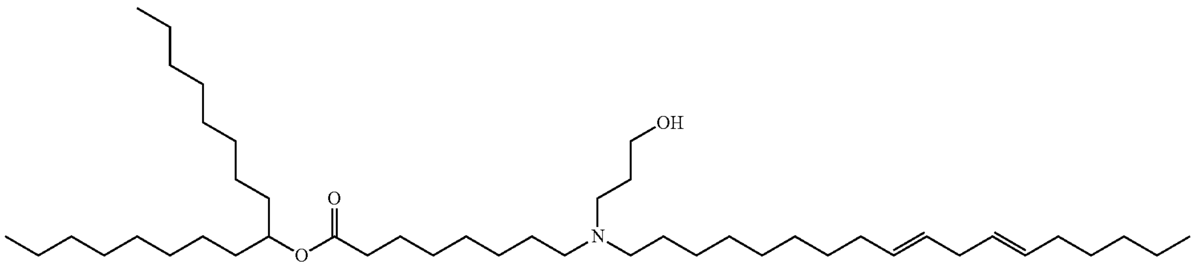
A9
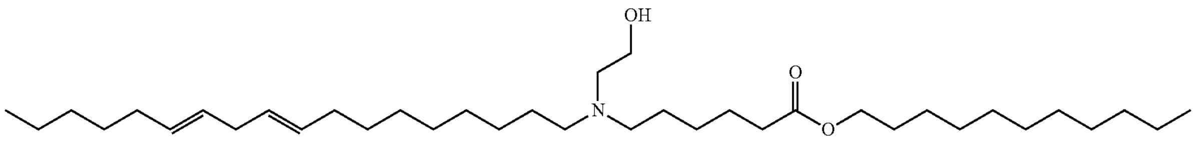
A10
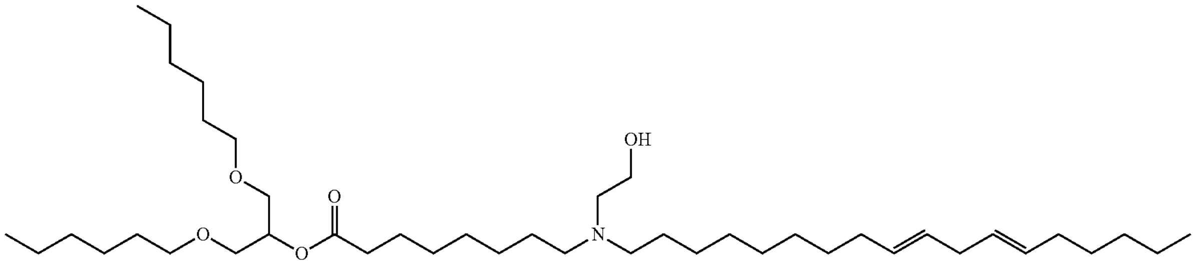
A11
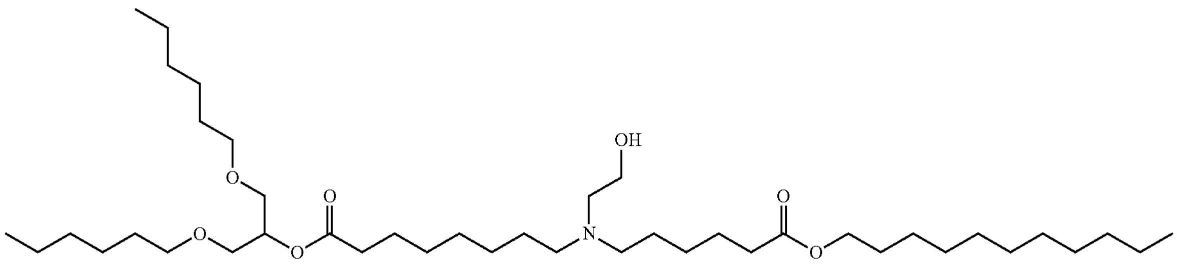
A12
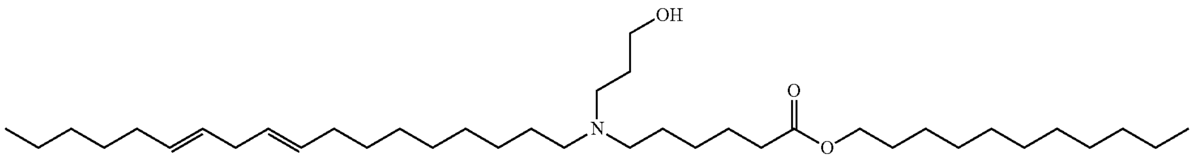

-continued
A13
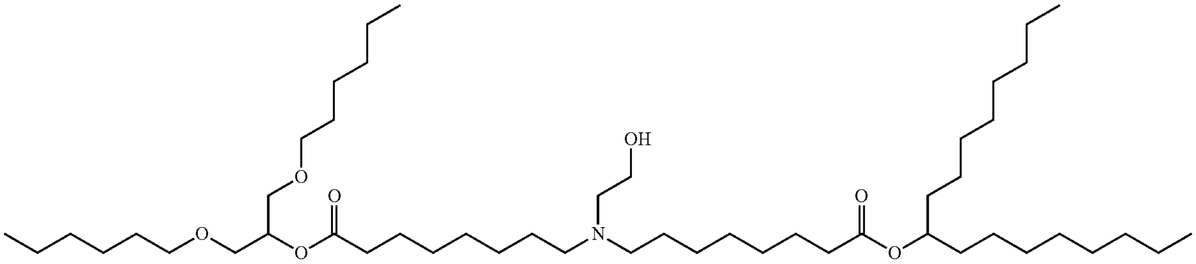
A15
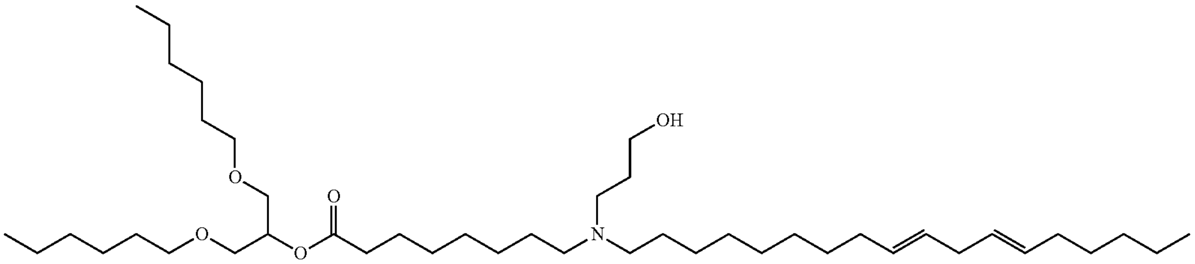
A16
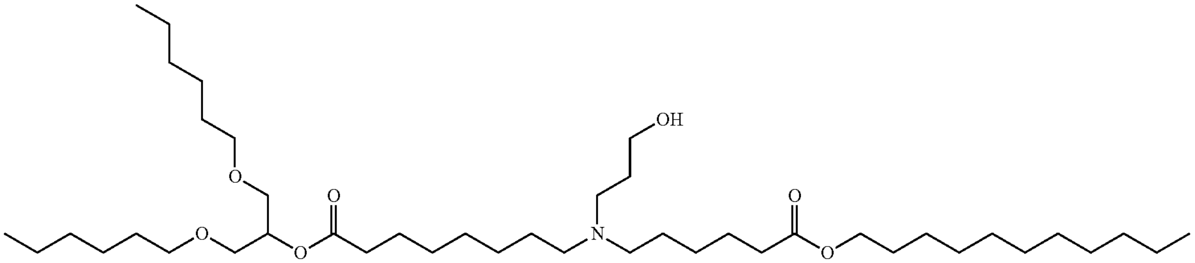
A17
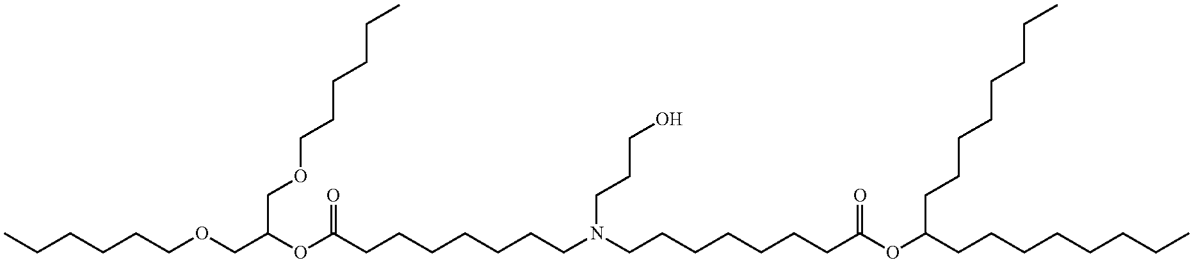
A18
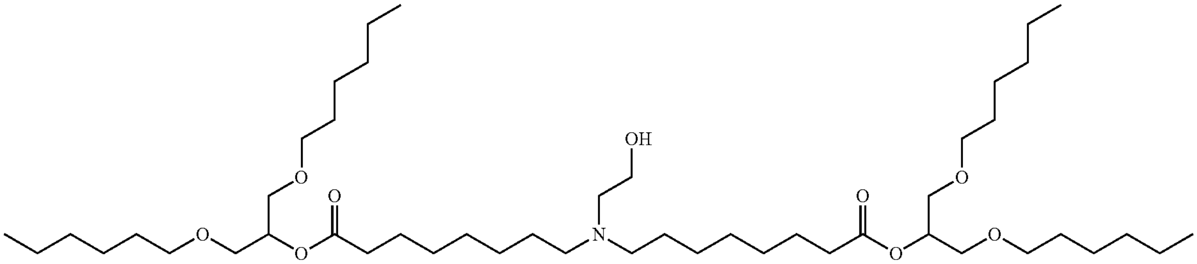

-continued
A19
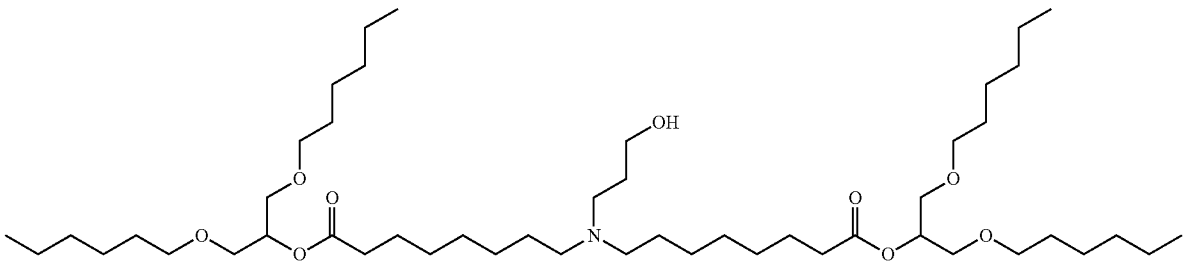
A20
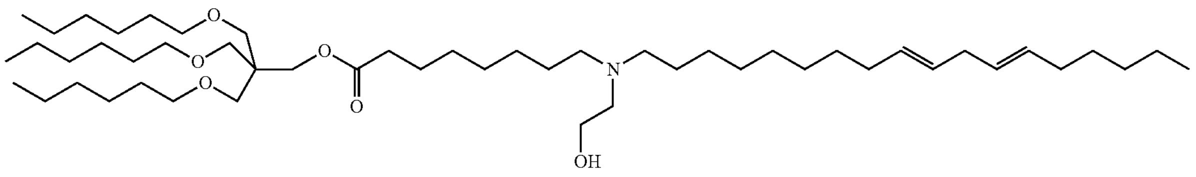
A21
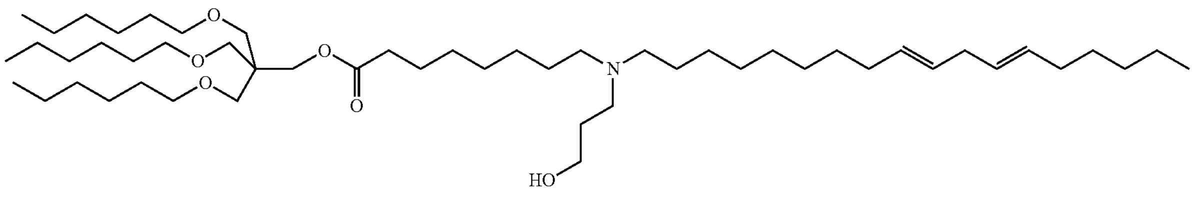
A22
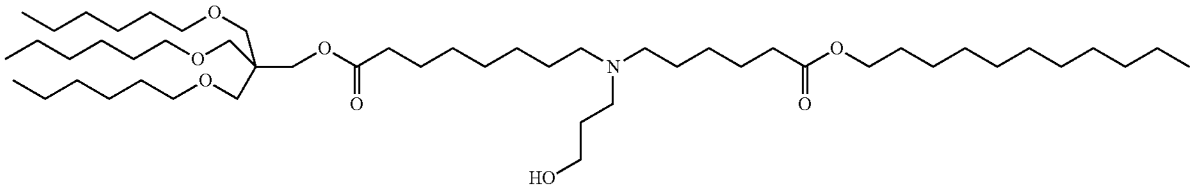
A23
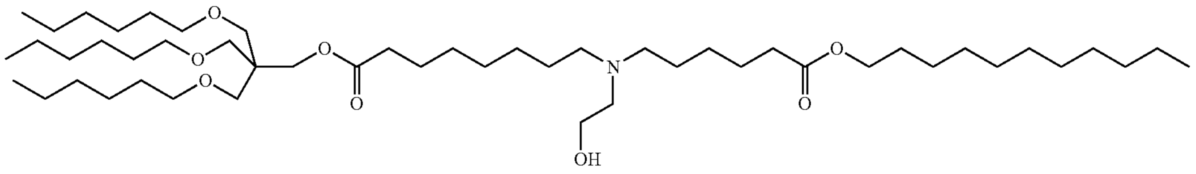
A24
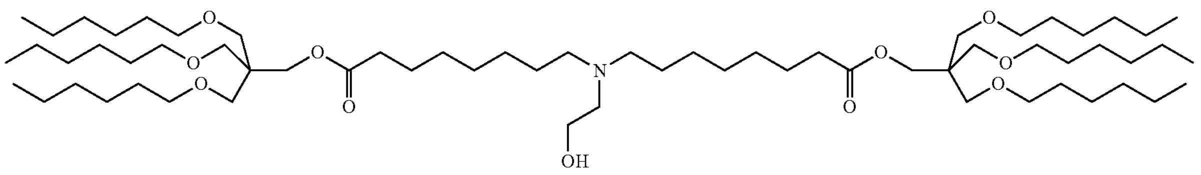
A25
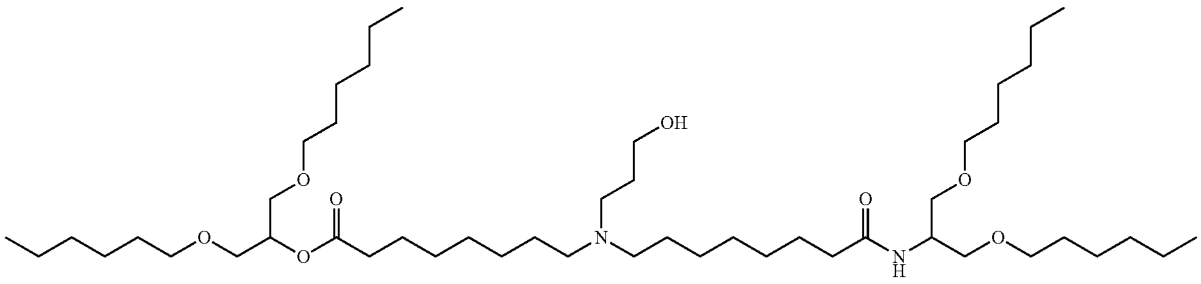

-continued
A26
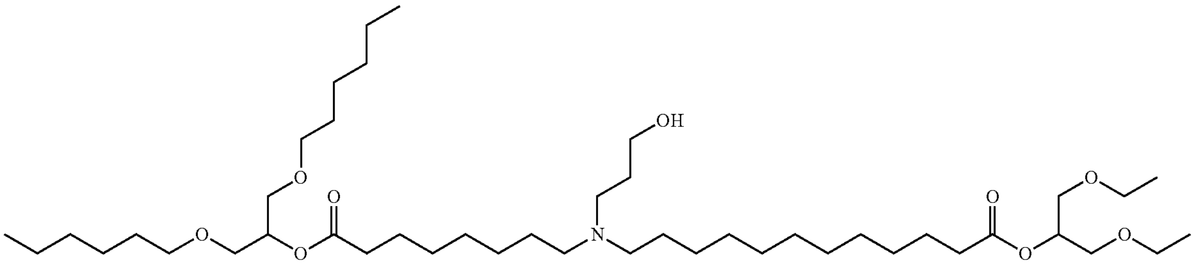
A27
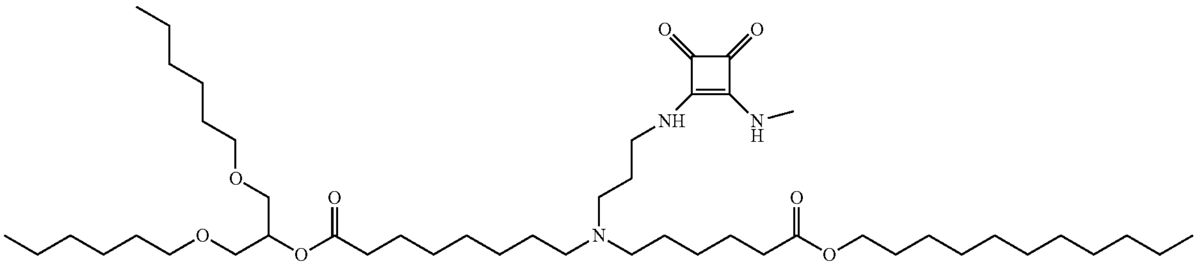
A28
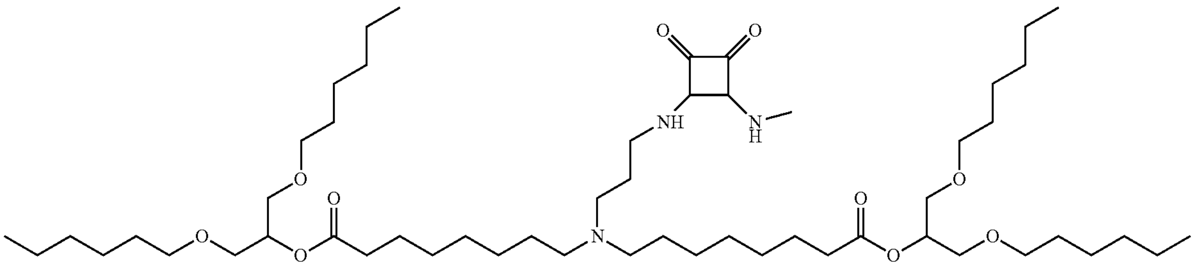
A29
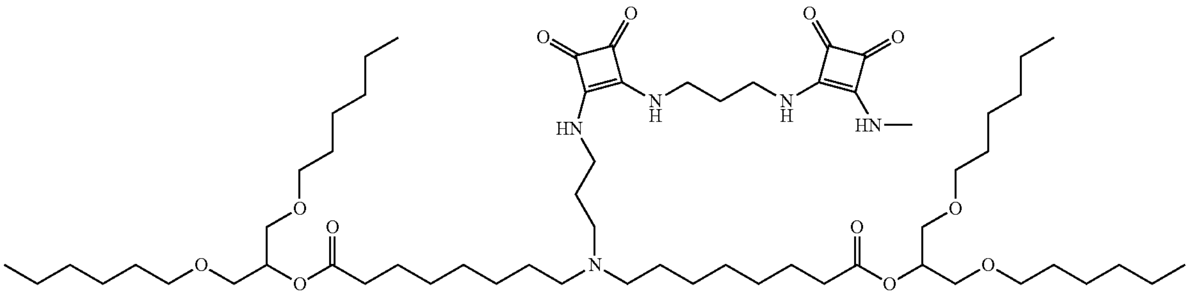

-continued
A30
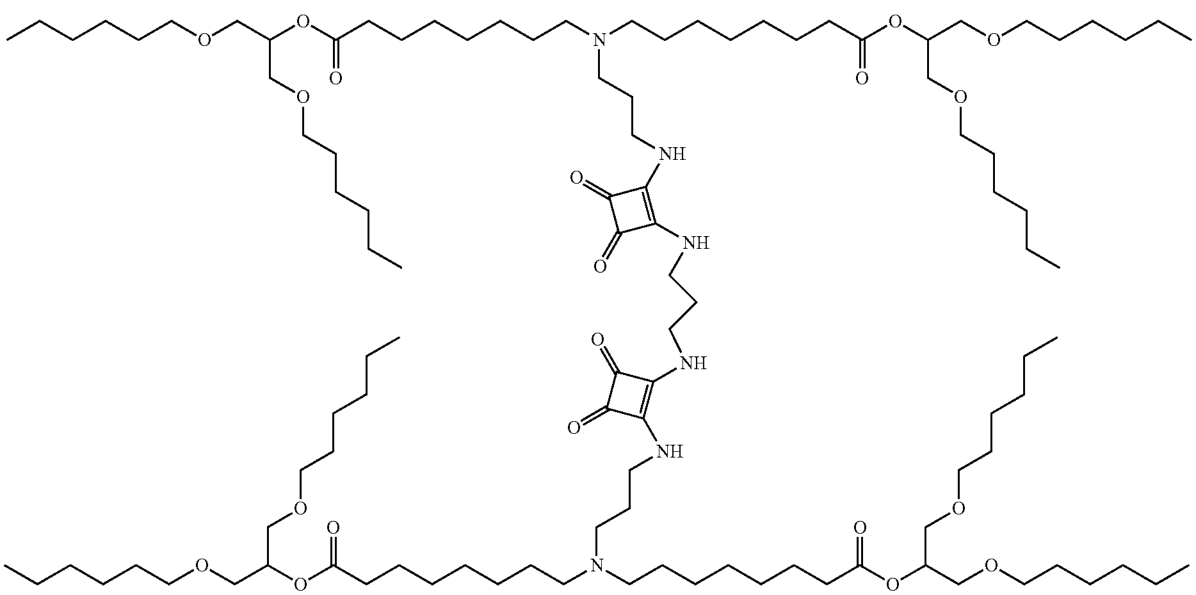
A31
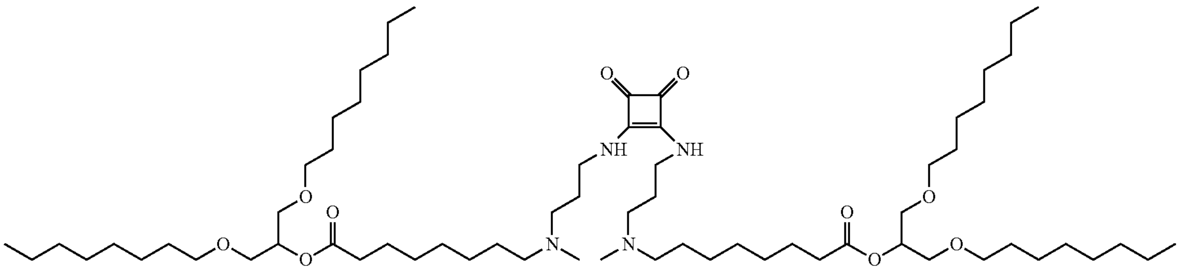
A32
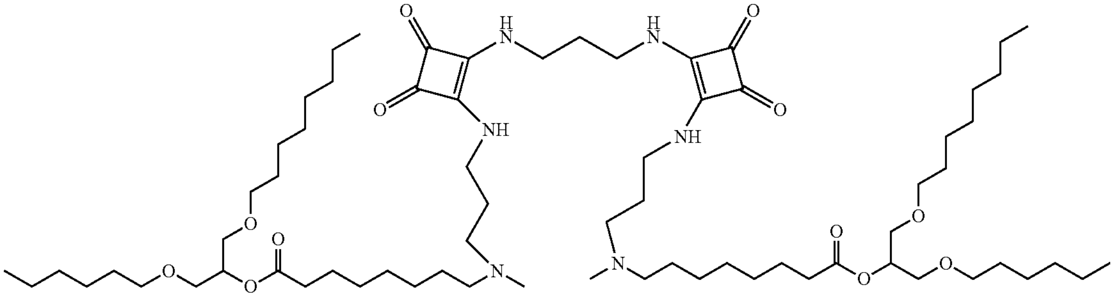
A34
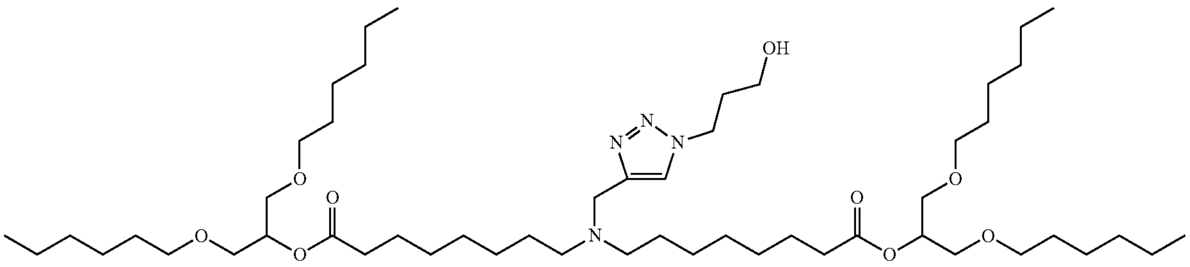

-continued
A35
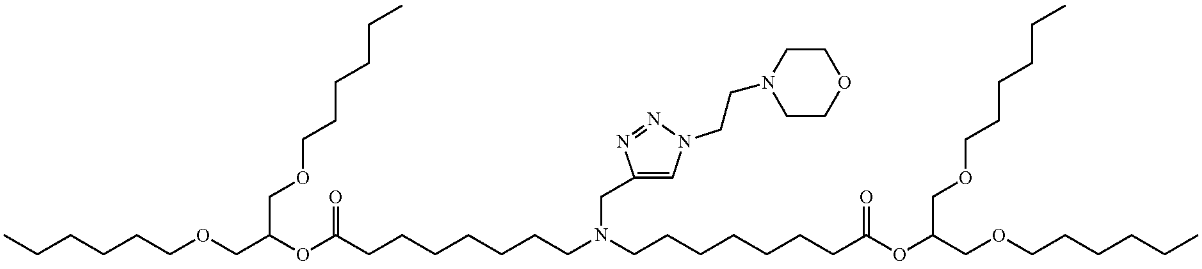
A36
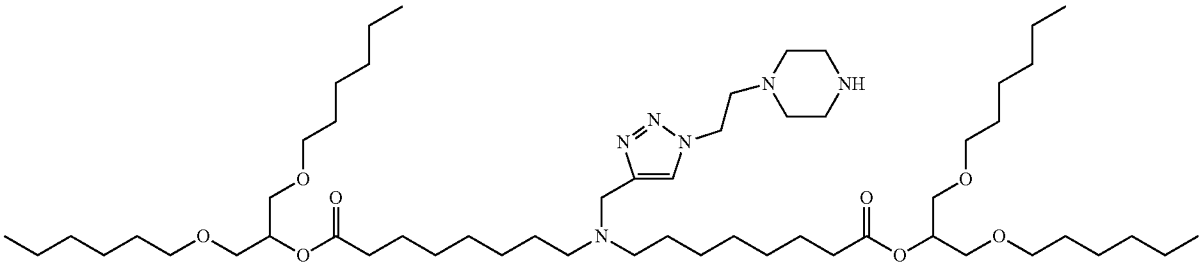
A37
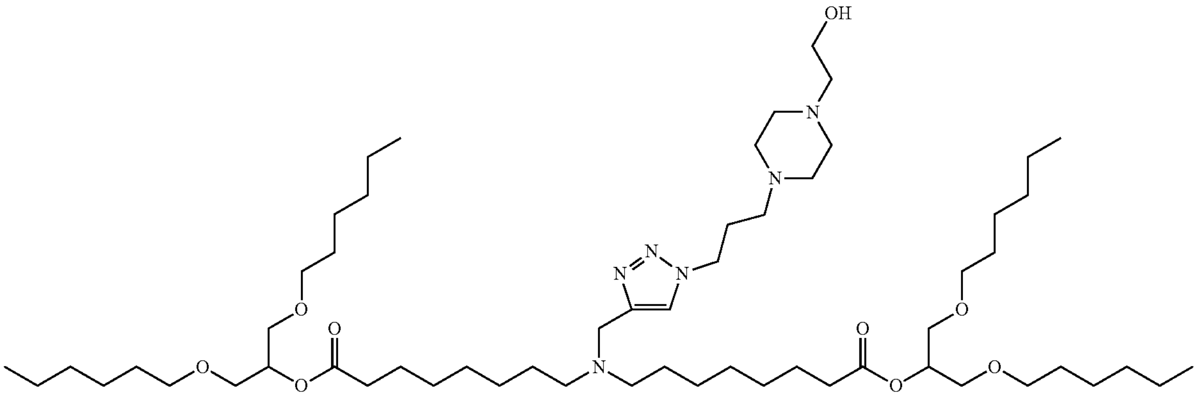
A38
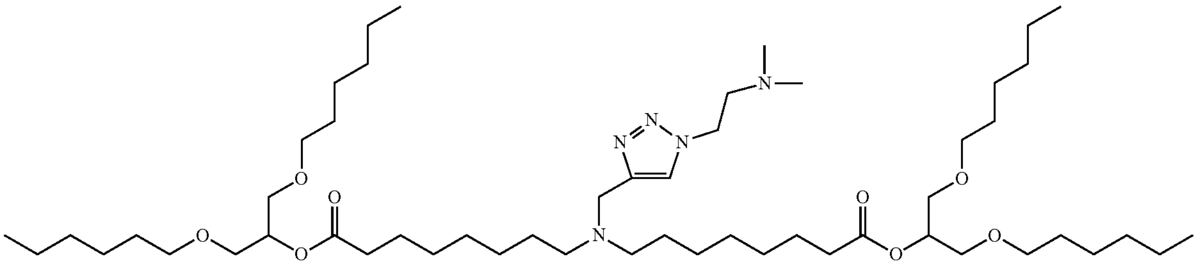

-continued
A39
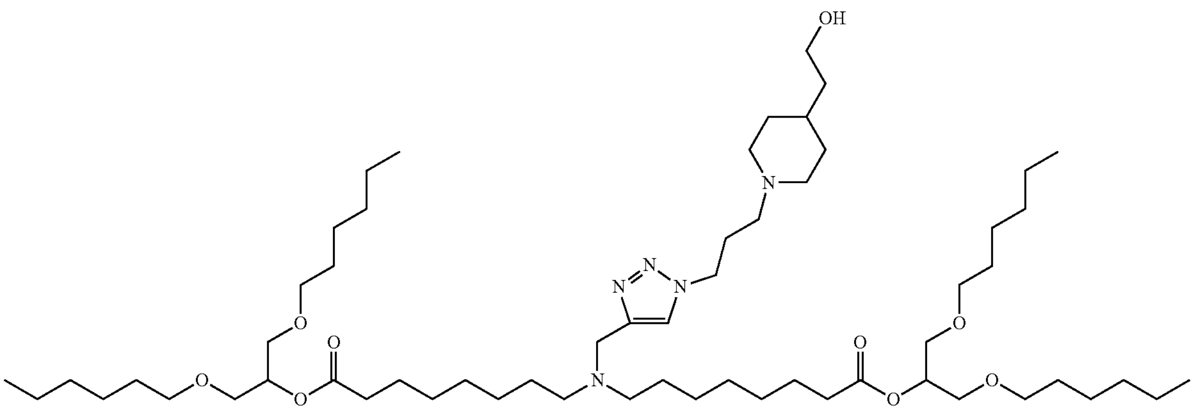
A40
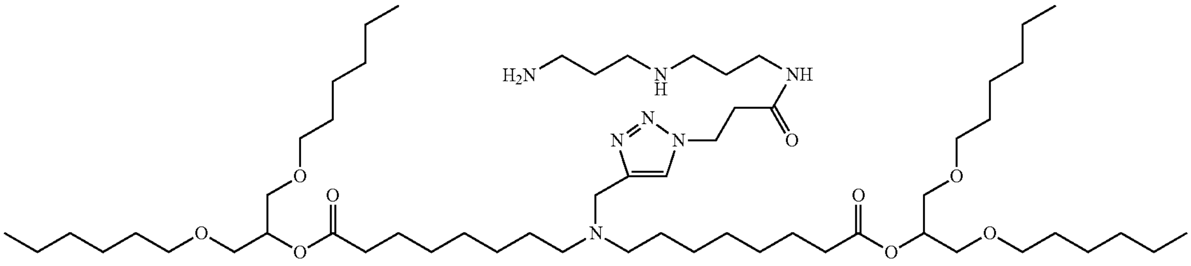
A42
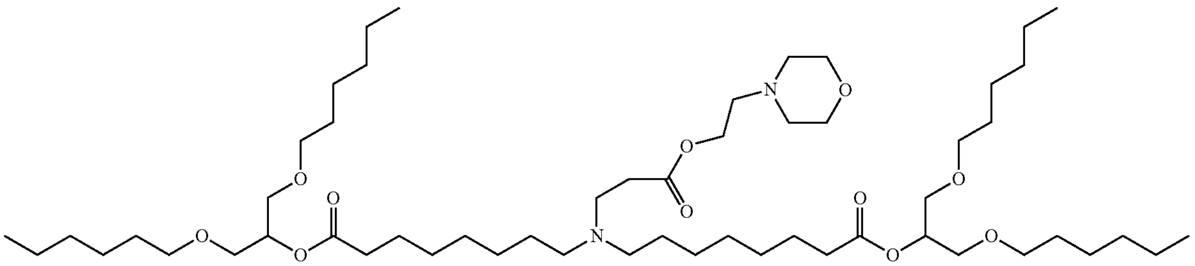
A43
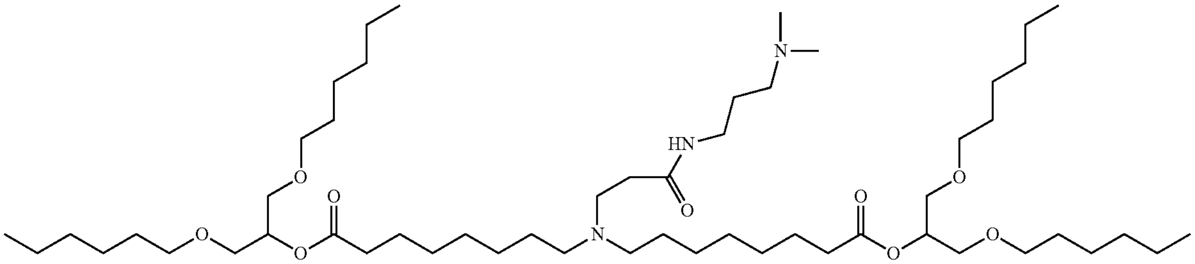
A44
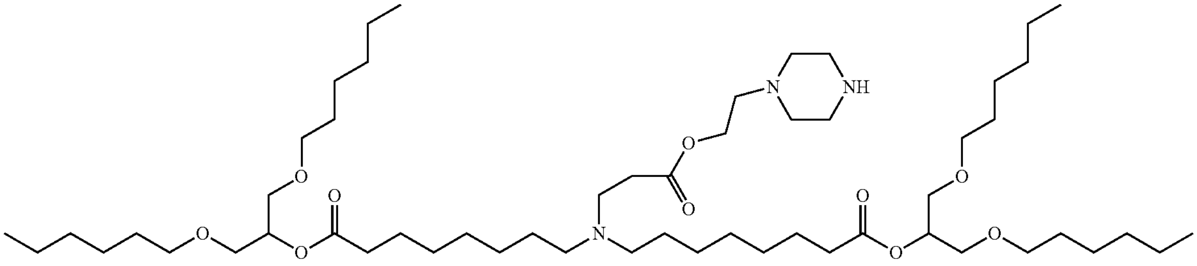

-continued

A45

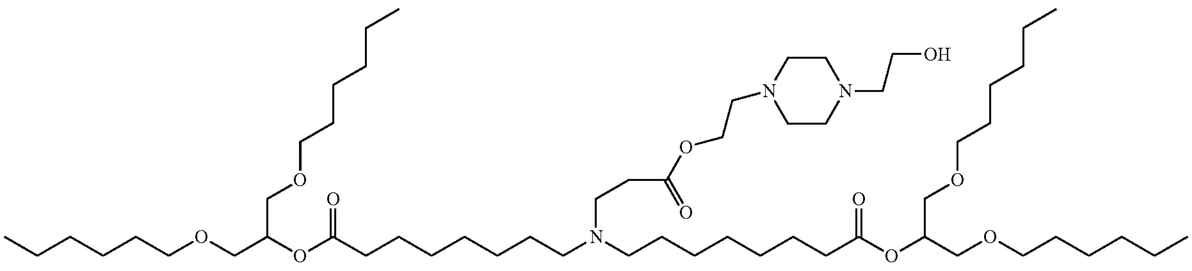

A46

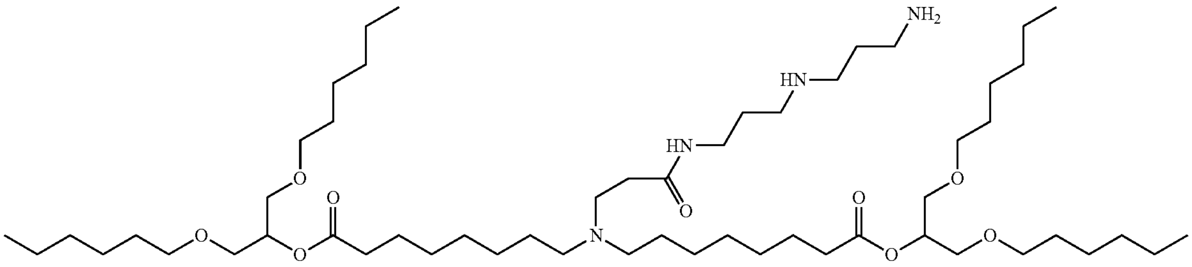

A47

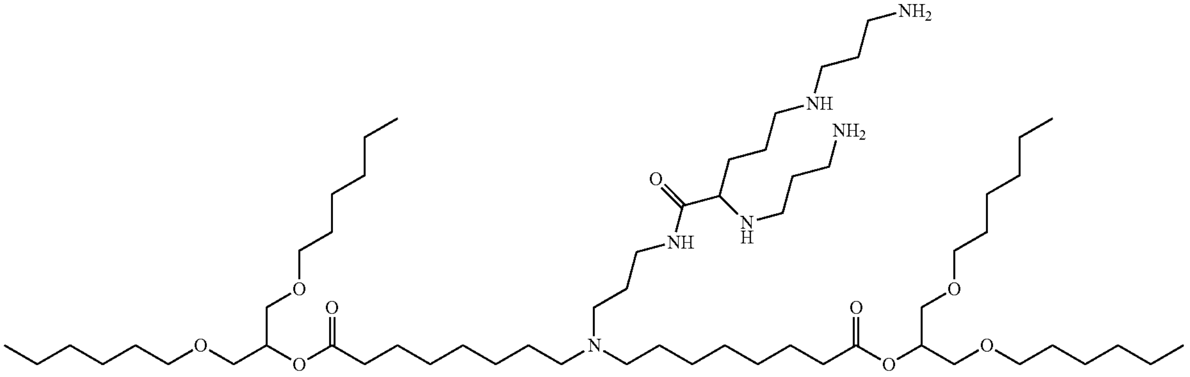

A48

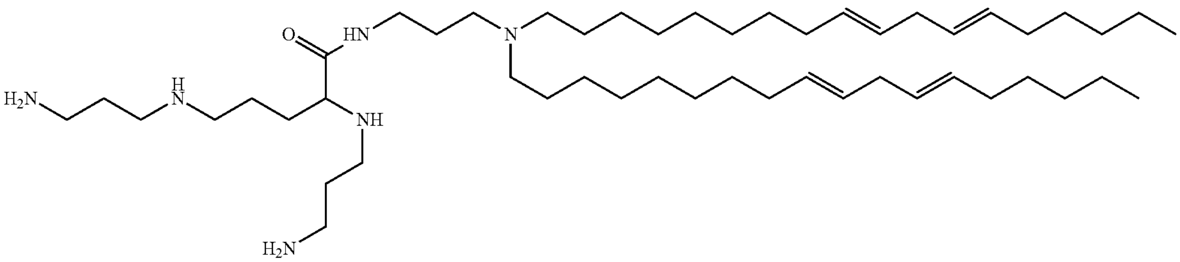

Compared with the prior art, such as PCT/US2016/052352 (published as WO2017/049245), and PCT/US2010/038224 (published as WO2010/144740), the ionizable lipids of the present disclosure differ from ionizable lipids disclosed in these documents in one or more of the following ways:

1. Different chemical structure: the 1 or 2 aliphatic chains that are connected to nitrogen (N) of tertiary amine contain an ester group formed with another saturated or unsaturated aliphatic chain having glycerol structure to become novel aliphatic chain with ether groups, the outcome shows that this transfection efficiency is higher than ionizable lipid having aliphatic chains lacking ether groups;

2. Different metabolites: the aliphatic chain of ionizable lipids of the disclosure consists of ester group, glycerol and short aliphatic chains. The metabolites of such molecules are small molecule compounds, such as short fatty acids, fatty alcohols or ethers, which are capable of being metabolized and extracted more easily and hard to accumulate in vivo, as well as lower toxicity.

3. Novel alkynyl intermediate structure: the alkynyl intermediate is formed by propargylamine and brominated aliphatic chain, which can click react with many azido compounds to generate a series of novel ionizable aliphatic compounds.

4. Ionizable lipids of the disclosure are easy to synthesize and easy to obtain the raw materials: the original raw materials are glycerol, short fatty alcohols and fatty acids, which are relatively inexpensive and easy to synthesize.

Definition

When the numeric range is listed, it includes each value and the subrange within the said range. For example, "$C_{1-6}$ alkyl" includes $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

The term "alkyl" refers to straight or branched saturated alkyl containing one or several carbon atoms (such as, 1, 2, 3, 4, 5, 6, 7, 8, 9, 10, 11, 12, 13, 14, 15, 16, 17, 18, 19, 20 or more carbon atoms). Specifically, "$C_{1-10}$ alkyl" refers to straight or branched saturated alkyl containing 1-10 carbon atoms. "$C_{2-18}$ alkyl" refers to randomly substituted straight or branched saturated alkyl containing 2-18 carbon atoms. Unless otherwise specified, the said alkyl in this specification refers to unsubstituted and substituted alkyl.

The term "alkenyl" refers to straight or branched alkyl containing two or more carbon atoms and at least one carbon-carbon double bond (such as, 2, 3, 4, 5, 6, 7, 8, 9, 10, 11, 12, 13, 14, 15, 16, 17, 18, 19, 20 or more carbon atoms). The alkenyl can include one, two, three, four or more carbon-carbon double bond. Specifically, "$C_{3-12}$ alkenyl" refers to straight or branched saturated alkenyl containing 3-12 carbon atoms and at least one carbon-carbon double bond. Specifically, "$C_{4-18}$ alkenyl" refers to straight or branched saturated alkenyl containing 4-18 carbon atoms and at least one carbon-carbon double bond. Unless otherwise specified, the said alkenyl in this specification refers to unsubstituted and substituted alkenyl.

The term "halogen" refers to fluorine (F), chlorine (Cl), bromine (Br) and iodine (I).

The term "$C_{1-6}$ alkyl halide" refers to the above mentioned "$C_{1-6}$ alkyl" is substituted by one or more halogen groups. Exemplary said alkyl halide includes but not limited to $—CF_3$, $—CH_2F$, $—CHF_2$, $—CHFCH_2F$, $—CH_2CHF_2$, $—CF_2CF_3$, $—CCl_3$, $—CH_2C_1$, $—CHCl_2$, and 2,2,2-trifluoro-1,1-dimethyl-ethyl.

The term "$C_{3-7}$cycloalkyl" refers to non-aromatic cyclic hydrocarbon group containing 3-7 cyclocarbon atoms and 0 heteroatom. Exemplary cycloalkyl groups include but are not limited to: cyclopropyl (C3), cyclopropenyl (C3), cyclobutyl (C4), cyclobutenyl (C4), cyclopentyl (C5), cyclopentenyl (C5), cyclohexyl (C6), cyclohexenyl (C6), cyclohexadienyl (C6), cycloheptyl (C7), cycloheptenyl (C7), cycloheptadienyl (C7), cycloheptatrienyl (C7), etc. The cycloalkyl group can be optionally substituted by one or more substituents, for example, it is substituted by 1-5 substituents, 1-3 substituents or 1 substituent.

The term "4-10 membered heterocyclyl" refers to 4-10 membered non-aromatic ring system containing ring carbon atom and 1-3 ring heteroatoms, wherein each heteroatom is independently selected from nitrogen, oxygen, sulfur, boron, phosphorus and silicon. Likewise, the term "4-7 membered heterocyclyl" and "5-10 membered heterocyclyl" are also have the same definition except that the total number of carbon atoms and heteroatoms varies for each grouping. In the heterocyclyl containing one or several nitrogen atoms, the point of attachment can be carbon or nitrogen atom as long as the valence allows. Exemplary 3 membered heterocyclyl groups containing one heteroatom include but are not limited to: aziridinyl, oxiranyl and thiorenyl. Exemplary 4 membered heterocyclyl groups containing one heteroatom include but are not limited to: azetidinyl, oxetanyl, and thietanyl. Exemplary 5 membered heterocyclyl groups containing one heteroatom include but are not limited to: tetrahydrofuranyl, dihydrofuryl, tetrahydrothienyl, dihydrothienyl, pyrrolidinyl, dihydropyrrolyl and pyrrolyl-2, 5-dione. Exemplary 5 membered heterocyclyl groups containing two heteroatoms include but are not limited to: dioxolanyl, oxasulfuranyl, disulfuranyl, and oxazolidin-2-ketone. Exemplary 5 membered heterocyclyl groups containing three heteroatoms include but are not limited to: triazolinyl, oxadiazolinyl and thiadiazolinyl. Exemplary 6 membered heterocyclyl groups containing one heteroatom include but are not limited to: piperidinyl, tetrahydropyranyl, dihydropyridyl and thianyl. Exemplary 6 membered heterocyclyl groups containing two heteroatoms include but are not limited to: piperazinyl, morpholinyl, dithianyl, dioxanyl. Exemplary 6 membered heterocyclyl groups containing three heteroatoms include but are not limited to: hexahydrotriazinyl. Exemplary 7 membered heterocyclyl groups containing one heteroatom include but are not limited to: azepanyl, oxepanyl and thiepanyl.

The term "$C_{6-10}$ aryl" refers to monocyclic or polycyclic (e.g., bicyclic) 4n+2 aromatic ring system (e.g., including 6 or 10 π electrons shared in a cyclic array) containing 6-10 ring carbon atoms and 0 heteroatom. In some embodiments, the aryl has six ring carbon atoms ("$C_6$ aryl"; e.g., phenyl). In some embodiments, the aryl has ten ring carbon atoms ("$C_{10}$ aryl"; e.g., naphthyl, e.g., 1-naphthyl and 2-naphthyl).

The term "5-10 membered heteroaryl" refers to 5-10 membered monocyclic or bicyclic 4n+2 aromatic ring system (e.g., including 6 or 10 π electrons shared in a cyclic array) containing ring carbon atom and 1-4 heteroatoms, wherein each heteroatom is independently selected from nitrogen, oxygen and sulfur. In the heteroaryl containing one or more nitrogen atoms, the point of attachment could be carbon or nitrogen atom, as valence permits. The heteroaryl bicyclic system in one or two rings can include one or more heteroatoms. The heteroaryl also includes ring system fused by the above mentioned heteroaryl ring and one or more cycloalkyl or heterocyclyl wherein the point of attachment located on the said heteroaryl ring, and the number of carbon atoms still continue to represent the number of carbon atoms in the heteroaryl ring system. Exemplary 5 membered heteroaryl groups containing one heteroatom include but are not limited to: pyrrolyl, furanyl and thiophenyl. Exemplary 5 membered heteroaryl groups containing two heteroatoms include but are not limited to: imidazolyl, pyrazolyl, oxazolyl, isoxazolyl, thiazolyl and isothiazolyl. Exemplary 5 membered heteroaryl groups containing three heteroatoms include but are not limited to: triazolyl, oxadiazolyl (e.g., 1,2,4-oxadiazolyl) and thiadiazolyl. Exemplary 5 membered heteroaryl groups containing four heteroatoms include but are not limited to: tetrazolyl. Exemplary 6 membered heteroaryl groups containing one heteroatom include but are not limited to: pyridinyl. Exemplary 6 membered heteroaryl groups containing two heteroatoms include but are not limited to: pyridazinyl, pyrimidinyl and pyrazinyl. Exemplary 6 membered heteroaryl groups containing three or four heteroatoms include but are not limited to: triazinyl and tetrazinyl. Exemplary 7 membered heteroaryl groups containing one heteroatom include but are not limited to: azepinyl, oxepinyl and thiepinyl. Exemplary 5, 6-bicyclic heteroaryl groups include but are not limited to: indolyl, isoindolyl, indazolyl, benzotriazolyl, benzothienyl, isobenzothienyl, benzofuranyl, benzoisofuranyl, benzimidazolyl, benzoxazolyl, benzisoxazolyl, benzoxadiazolyl, benzothiazolyl, benzisothiazolyl, benzothiadiazolyl, indolizinyl and purinyl. Exemplary 6, 6 bicyclic heteroaryl groups include but are not limited to: naphthyridinyl, pteridinyl, quinolinyl, isoquinolinyl, cinnolinyl, quinoxalinyl, phthalazinyl and quinazolinyl.

The term "isomer" refers to different compounds with the same molecular formula. The disclosure especially relates to stereoisomers, the term "stereoisomer" refers to isomers that are only different in the atom space arrangement.

In some situations, the invention's compounds can form into salts, which are also in the scope of the invention. The term "salt (one or more)" refers to acidic and/or basic salts formed by inorganic and/or organic acids and bases. The salts of compounds of the invention are preferably the pharmaceutically acceptable salts.

The term "pharmaceutically acceptable salts" refers to those carboxylate salts, amino acid addition salts of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N, N'-dibenzylethylenediamine, chloroprocaine, choline, diethanolamine, ethylenediamine, N-methylglucamine, and procaine.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

Salts may be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts may also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts may include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. (See, for example, Berge S. M. et al., "Pharmaceutical Salts," *J. Pharm. Sci.,* 1977; 66:1-19 which is incorporated herein by reference.)

Examples of pharmaceutically acceptable, non-toxic esters of the compounds of this invention include $C_1$-$C_6$ alkyl esters wherein the alkyl group is a straight or branched chain. Acceptable esters also include $C_5$-$C_7$ cycloalkyl esters as well as arylalkyl esters such as, but not limited to benzyl. $C_1$-$C_4$ alkyl esters are preferred. Esters of the compounds of the present invention may be prepared according to conventional methods "March's Advanced Organic Chemistry, 5th Edition". M. B. Smith & J. March, John Wiley & Sons, 2001.

Examples of pharmaceutically acceptable, non-toxic amides of the compounds of this invention include amides derived from ammonia, primary $C_1$-$C_6$ alkyl amines and secondary $C_1$-$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$-$C_3$ alkyl primary amines and $C_1$-$C_2$ dialkyl secondary amines are preferred. Amides of the compounds of the invention may be prepared according to conventional methods such as "March's Advanced Organic Chemistry, 5th Edition". M. B. Smith & J. March, John Wiley & Sons, 2001.

The term "acceptable carrier" refers to suitable carrier using current materials for the purpose of the invention, without undue toxicity, irritation, allergic response, and the like, commensurate with a reasonable benefit/risk ratio.

EXAMPLES

To make the purpose, technological protocol and benefit of the invention clearer, the present invention is illustrated in further details by the following examples, as well as drawings.

Example 1—Synthesis of A1

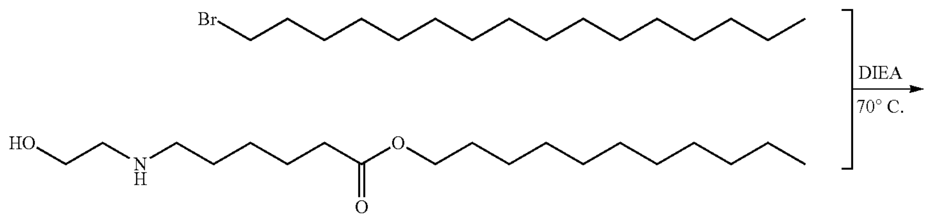

-continued

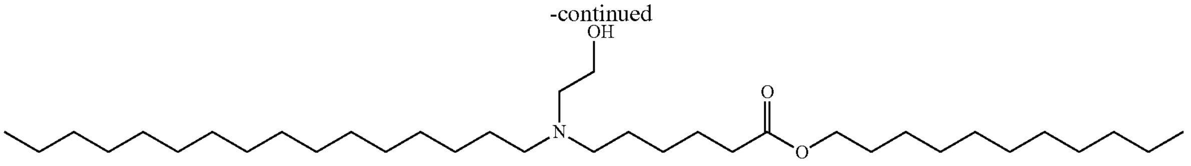

Hexadecane bromide (2.22 g, 7.28 mmol) was soluted in 50 mL absolute ethanol, N,N-diisopropylethylamine (DIEA, 1.17 g, 9.10 mmol) and alkanolamine compound (2 g, 6.07 mmol) were added, reacted at 80° C. for 18 h. After the reaction was completed, the solvent was removed by concentrating, the reaction was diluted with 200 mL ethyl acetate (EA), washed once with 200 mL water, extracted, the organic layer was dried over, concentrated, and passed through a silica gel column for purification (DCM: MeOH=3%-5%), 1.2 g oily product was obtained. MS(ES): m/z $(M+H)^+$ 553.54. $^1$HNMR (CDCl3) δ:ppm: 2H), 3.57 (t, 2H), 2.62 (bs, 2H), 2.50 (br, 4H), 2.29 (m, 2H), 1.68-1.25 (m, 52H), 0.88 (m, 6H).

The synthetic routes for the following examples and synthesis of A5-A7, A9-A13, A15-A32 were designed based on this example, most were as follows: a substitution reaction occurs through a brominated compound or a ketene compound and a primary/secondary amine compound (e.g., alkanolamine compound).

Example 2—Synthesis of A5

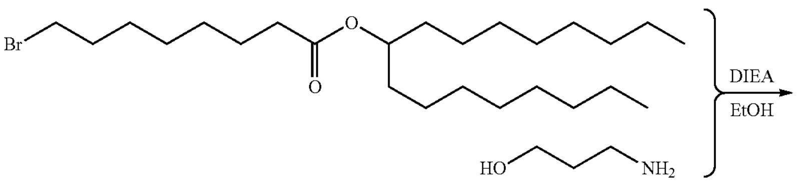

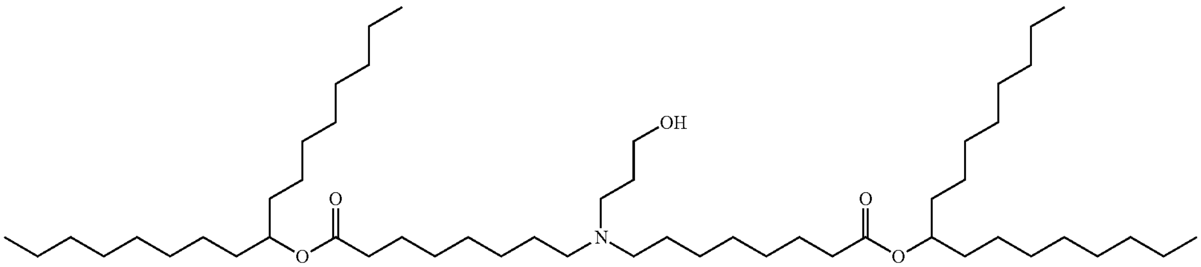

A5 was synthesized employing reaction steps similar to Example 1, 0.75 g oily product was obtained. MS(ES): m/z $(M+H)^+$ 835.80. $^1$HNMR ($CDCl_3$) δ:ppm: 4.87 (m, 2H), 3.79 (t, 2H), 2.67 (br, 2H), 2.45 (br, 4H), 2.27 (t, 4H), 1.70-1.25 (m, 78H), 0.90 (m, 12H).

Example 3—Synthesis of A6
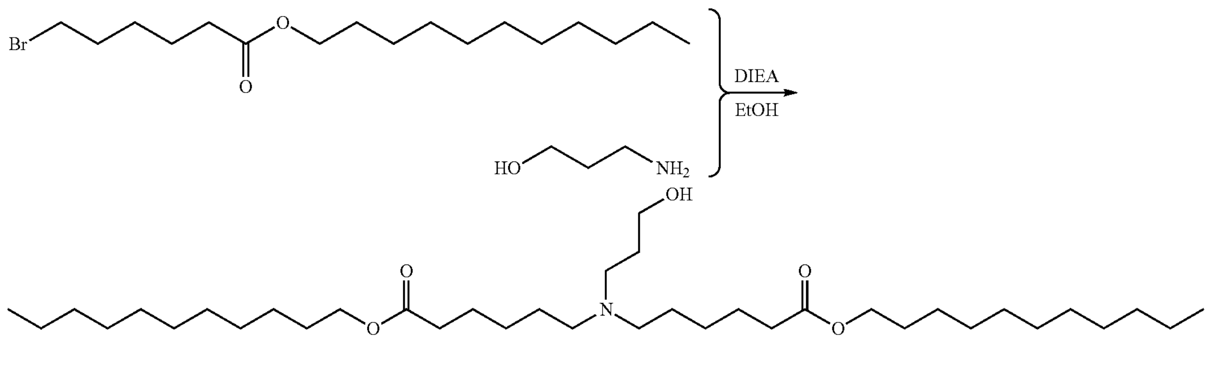
A6 was synthesized employing reaction steps similar to Example 1, 0.51 g oily product was obtained. MS(ES): m/z $(M+H)^+$ 611.55. $^1$HNMR ($CDCl_3$) δ:ppm: 4.05 (t, 4H), 3.78 (m, 2H), 2.65 (t, 2H), 2.43 (br, 4H), 2.29 (m, 4H), 1.69-1.31 (m, 50H), 0.90 (m, 6H).
Example 4—Synthesis of A7

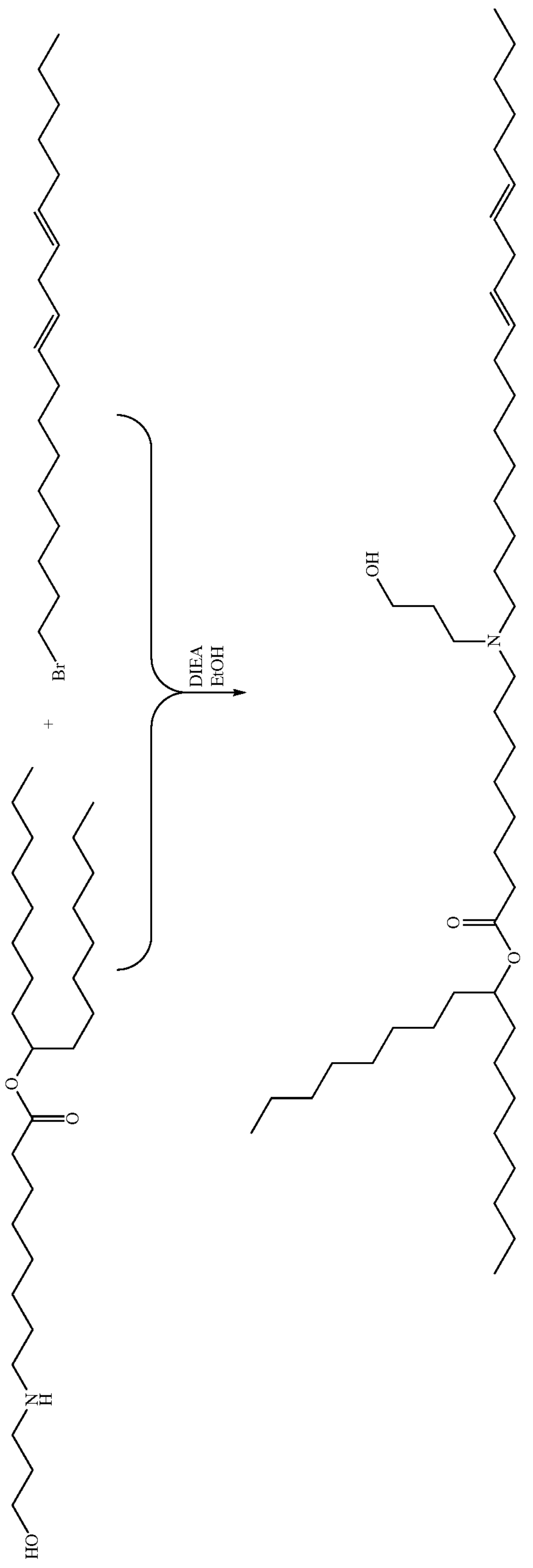
DIEA
EtOH

A7 was synthesized employing reaction steps similar to Example 1, 2.45 g oily product was obtained. MS(ES): m/z $(M+H)^+$ 703.68. $^1$HNMR ($CDCl_3$) δ:ppm: 5.38-5.31 (m, 4H), 4.86 (m, 1H), 3.79 (t, 2H), 2.77 (m, 2H), 2.67 (br, 2H), 2.45 (br, 4H), 2.27 (m, 2H), 2.04 (m, 4H), 1.70-1.25 (m, 58H), 0.90 (m, 9H).

Example 5—Synthesis of A9

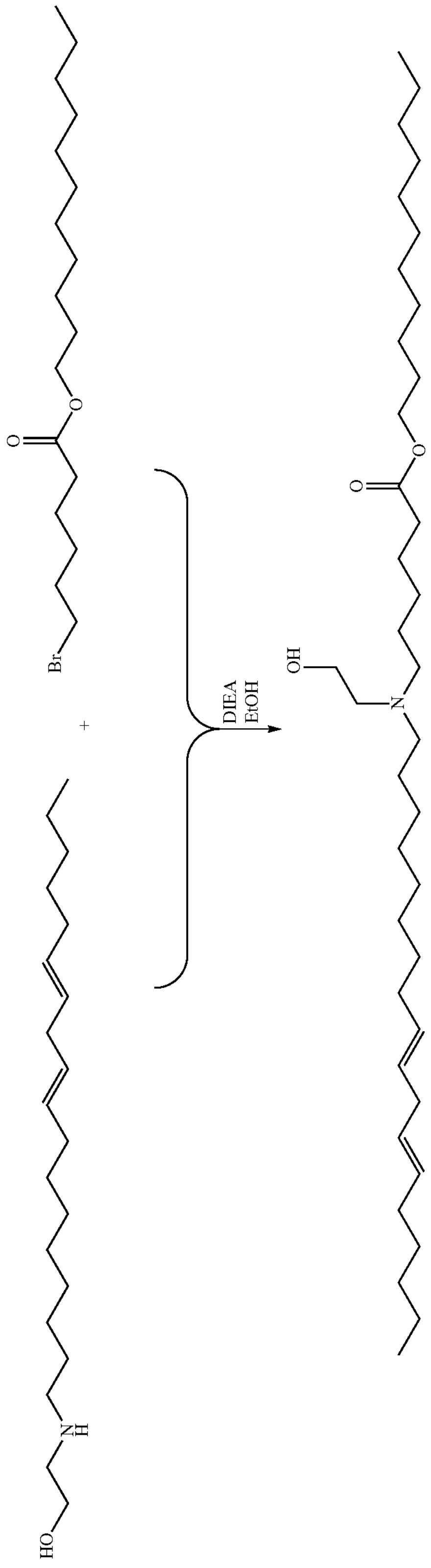
DIEA
EtOH

A9 was synthesized employing reaction steps similar to Example 1, 1.6 g oily product was obtained. MS(ES): m/z $(M+H)^+$ 577.54. $^1$HNMR ($CDCl_3$) δ:ppm: 5.38-5.33 (m, 4H), 4.06 (t, 2H), 3.60 (t, 2H), 2.77 (t, 2H), 2.66 (m, 2H), 2.54 (bs, 4H), 2.30 (m, 2H), 2.05 (m, 4H), 1.68-1.25 (m, 42H), 0.88 (m, 6H).

Example 6—Synthesis of A10

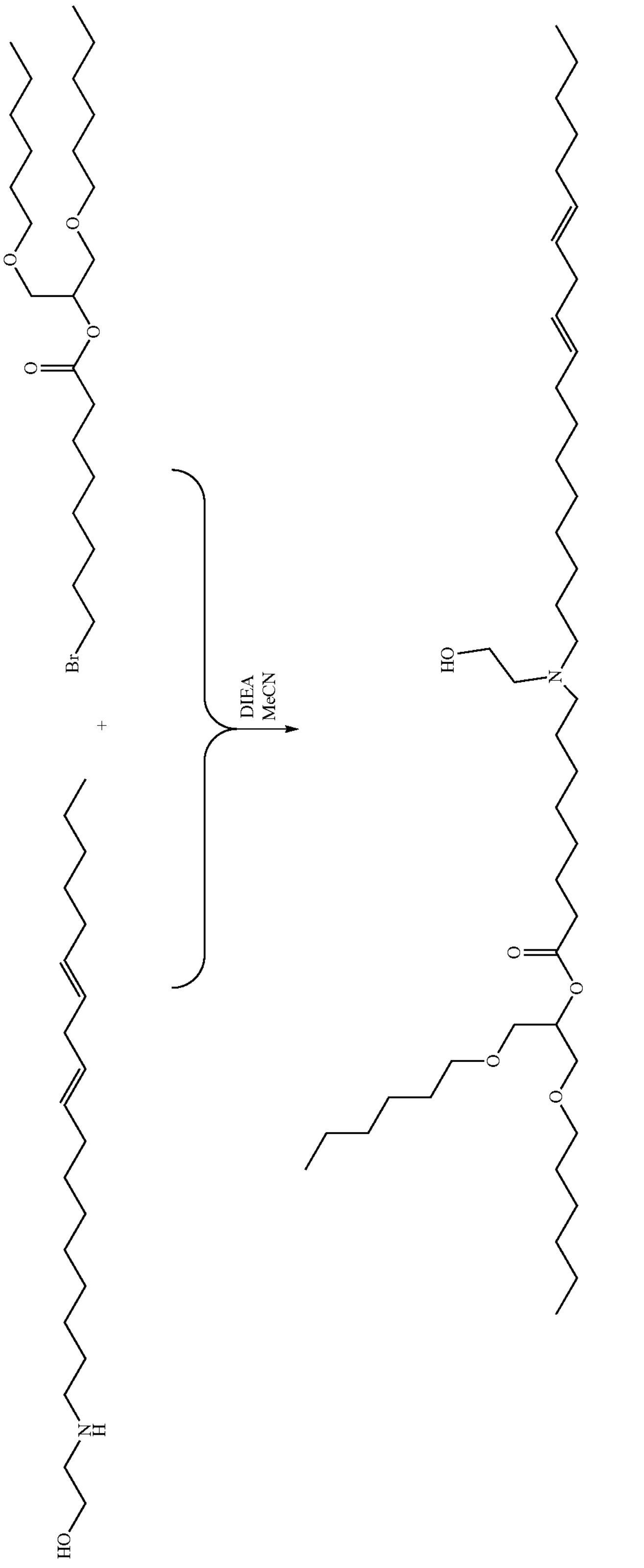
DIEA
MeCN

A10 was synthesized employing reaction steps similar to Example 1, 0.4 g oily product was obtained. MS(ES): m/z $(M+H)^+$ 693.63. $^1$HNMR ($CDCl_3$) δ:ppm: 5.36 (m, 4H), 5.10 (m, 1H), 3.56 (t, 4H), 3.46-3.40 (br, 4H), 2.76 (t, 2H), 2.64 (br, 4H), 2.51 (bs, 4H), 2.32 (m, 2H), 2.05 (m, 6H), 1.67-1.25 (m, 44H), 0.88 (m, 9H).

Example 7—Synthesis of A11

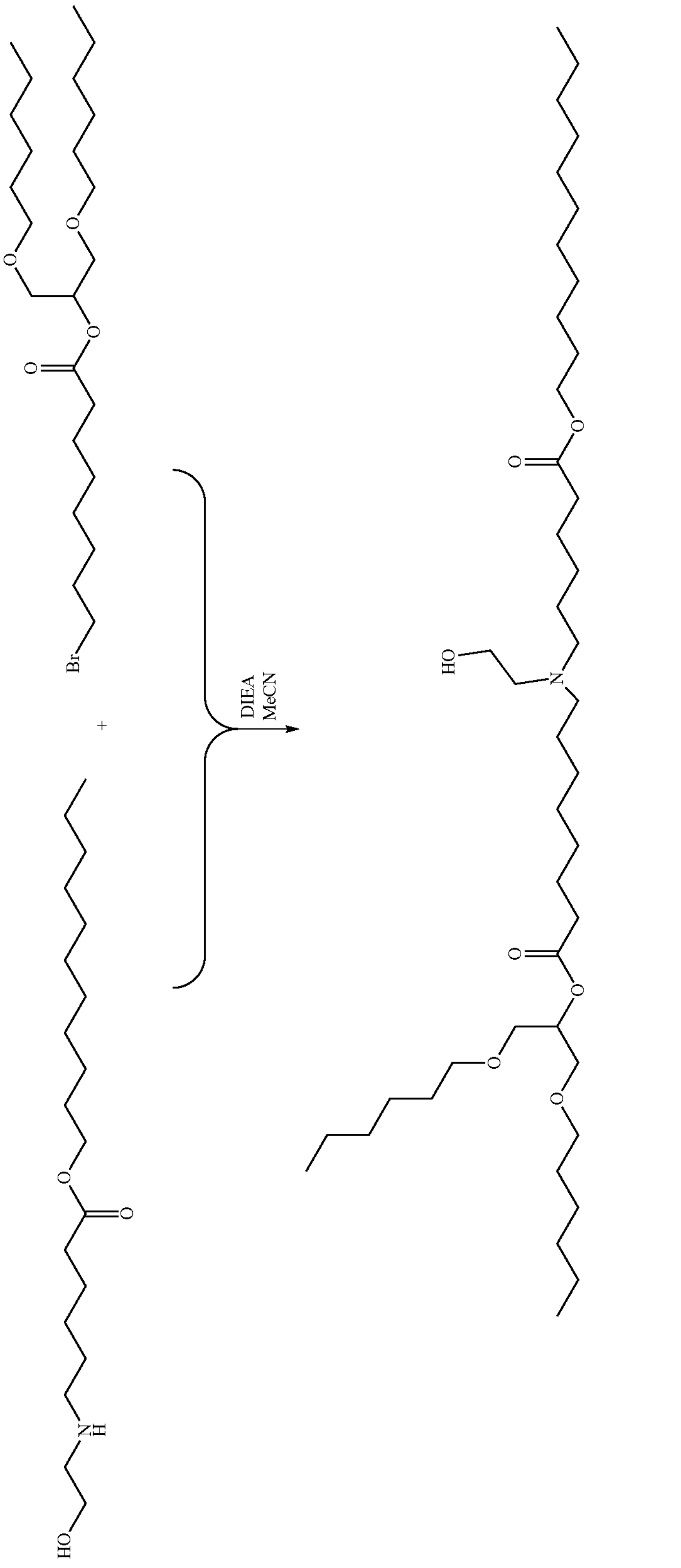
DIEA
MeCN

A11 was synthesized employing reaction steps similar to Example 1, 0.5 g oily product was obtained. MS(ES): m/z $(M+H)^+$ 713.62. $^1$HNMR ($CDCl_3$) δ:ppm: 5.10 (m, 1H), 4.05 (d, 4H), 4.03 (t, 4H), 3.54 (m, 2H), 3.43 (s, 2H), 3.16 (t, 2H), 3.10 (br, 4H), 2.32 (t, 4H), 1.66-1.27 (m, 50H), 0.88 (m, 9H).

Example 8—Synthesis of A12

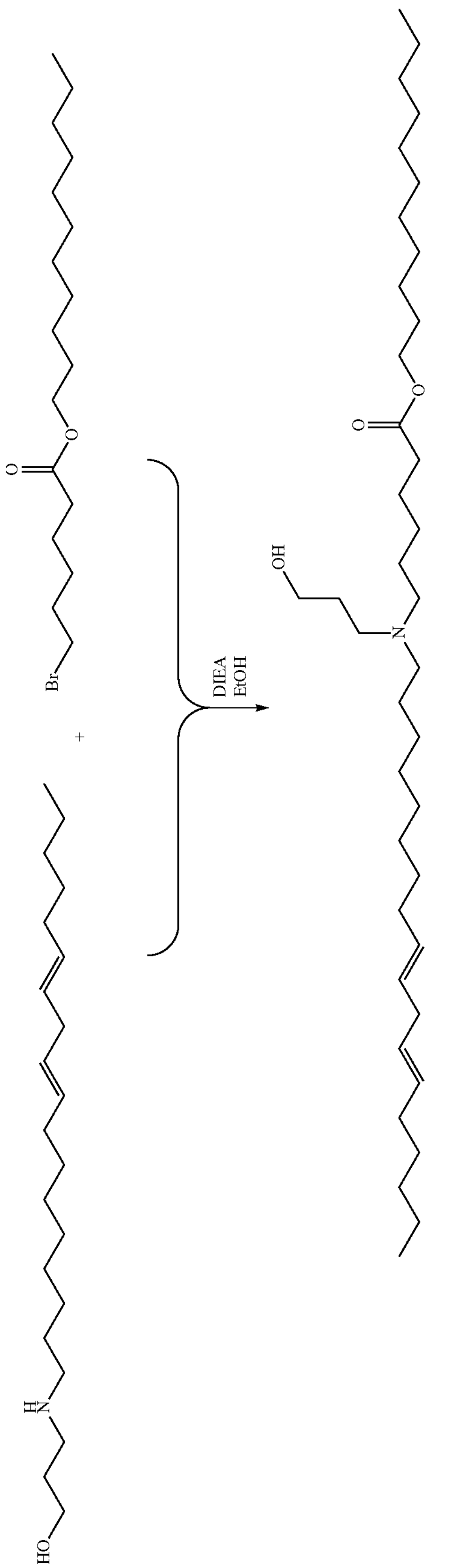
DIEA
EtOH

A12 was synthesized employing reaction steps similar to Example 1, 2.68 g oily product was obtained. MS(ES): m/z $(M+H)^+$ 591.56, $^1$HNMR ($CDCl_3$) δ:ppm: 5.37-5.35 (m, 4H), 4.05 (t, 2H), 3.78 (t, 2H), 2.77 (t, 2H), 2.64 (m, 2H), 2.41 (bs, 4H), 2.31 (m, 2H), 2.03 (m, 4H), 1.68-1.25 (m, 44H), 0.88 (m, 6H).

Example 9—Synthesis of A13

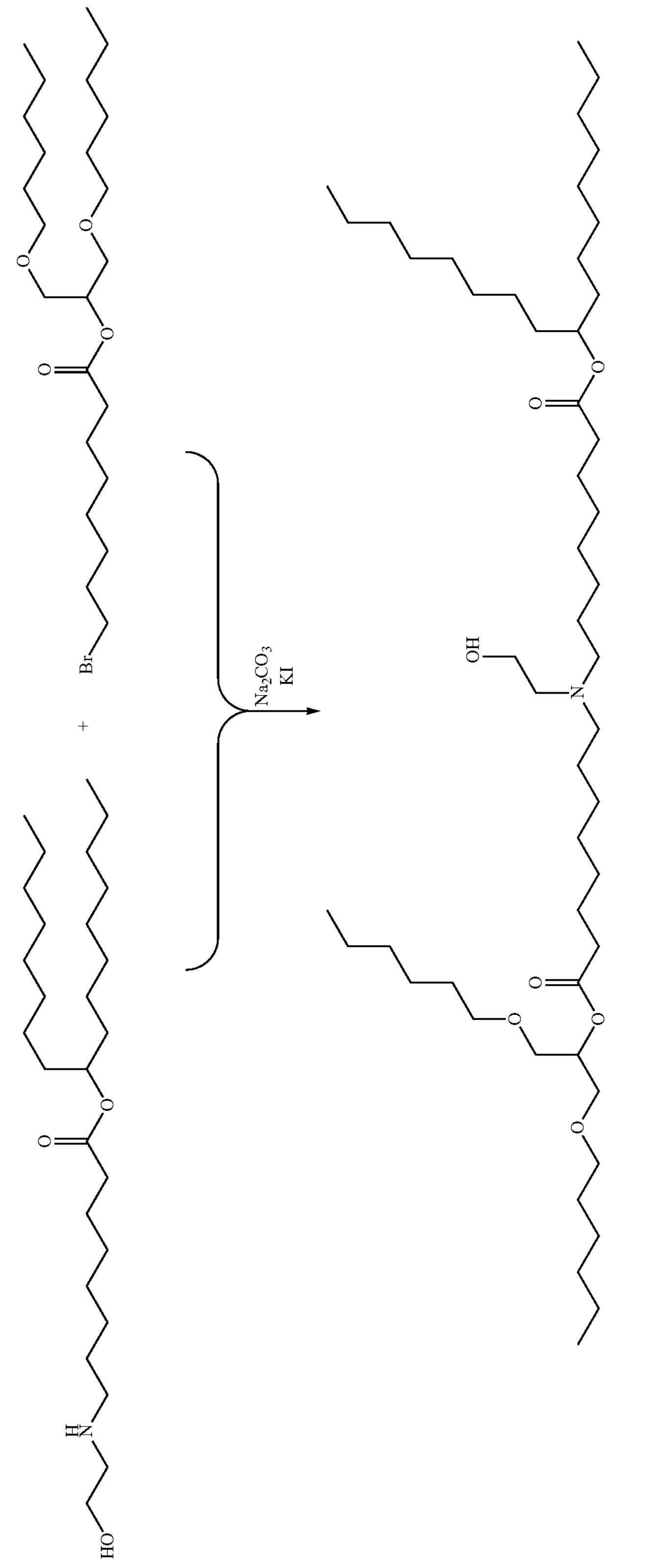
$Na_2CO_3$
KI

A13 was synthesized employing reaction steps similar to Example 1, 1.2 g oily product was obtained. MS(ES): m/z $(M+H)^+$ 825.74; $^1$HNMR ($CDCl_3$) δ:ppm: 5.12 (m, 1H), 4.86 (m, 1H), 3.65-3.40 (m, 10H), 2.72 (br, 2H), 2.60 (br, 4H), 2.34-2.26 (m, 4H), 1.62-1.25 (m, 64H), 0.88 (m, 12H).

Example 10—Synthesis of A15

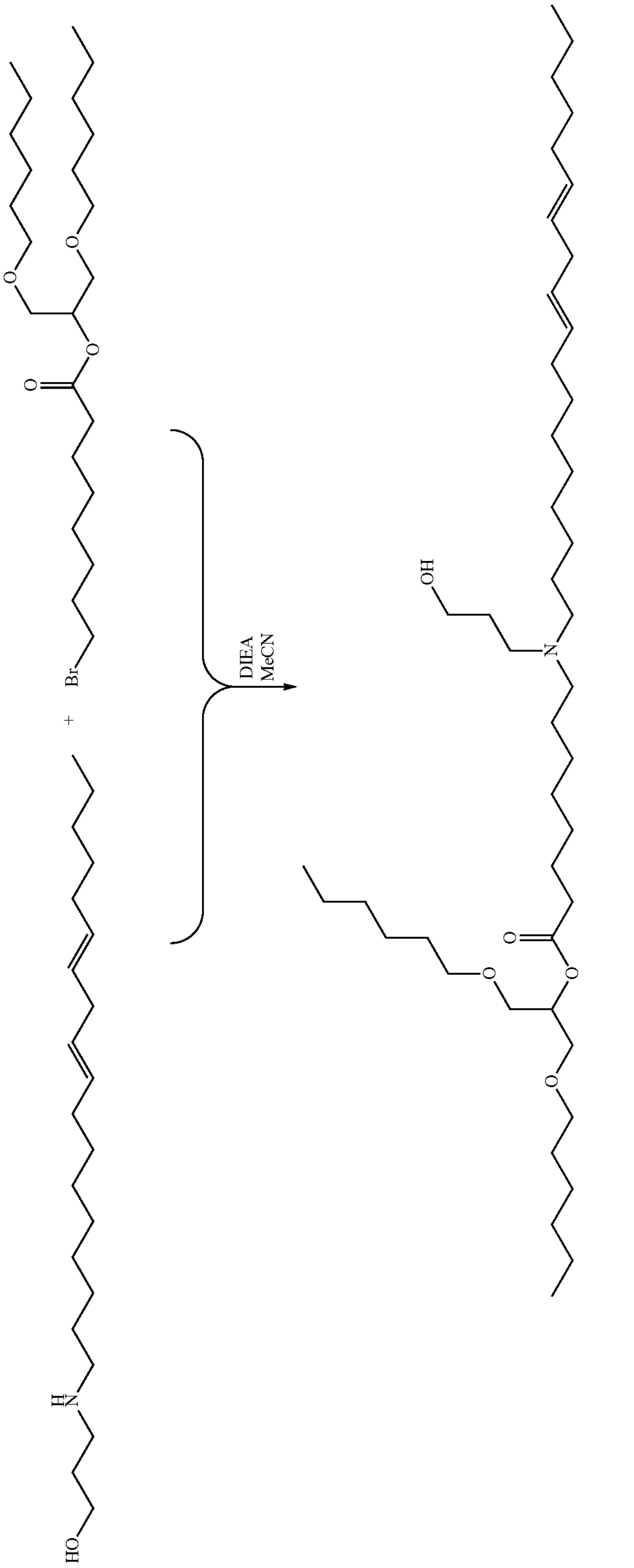
DIEA
MeCN

A15 was synthesized employing reaction steps similar to Example 1, 0.4 g oily product was obtained. MS(ES): m/z $(M+H)^+$ 707.64. $^1$HNMR ($CDCl_3$) δ:ppm: 5.34 (m, 4H), 5.10 (m, 1H), 3.79 (t, 2H), 3.56-3.41 (m, 8H), 2.80 (t, 2H), 2.77 (t, 2H), 2.46 (br, 4H), 2.32 (m, 2H), 2.05 (m, 4H), 1.67-1.25 (m, 46H), 0.88 (m, 9H).

Example 11—Synthesis of A16

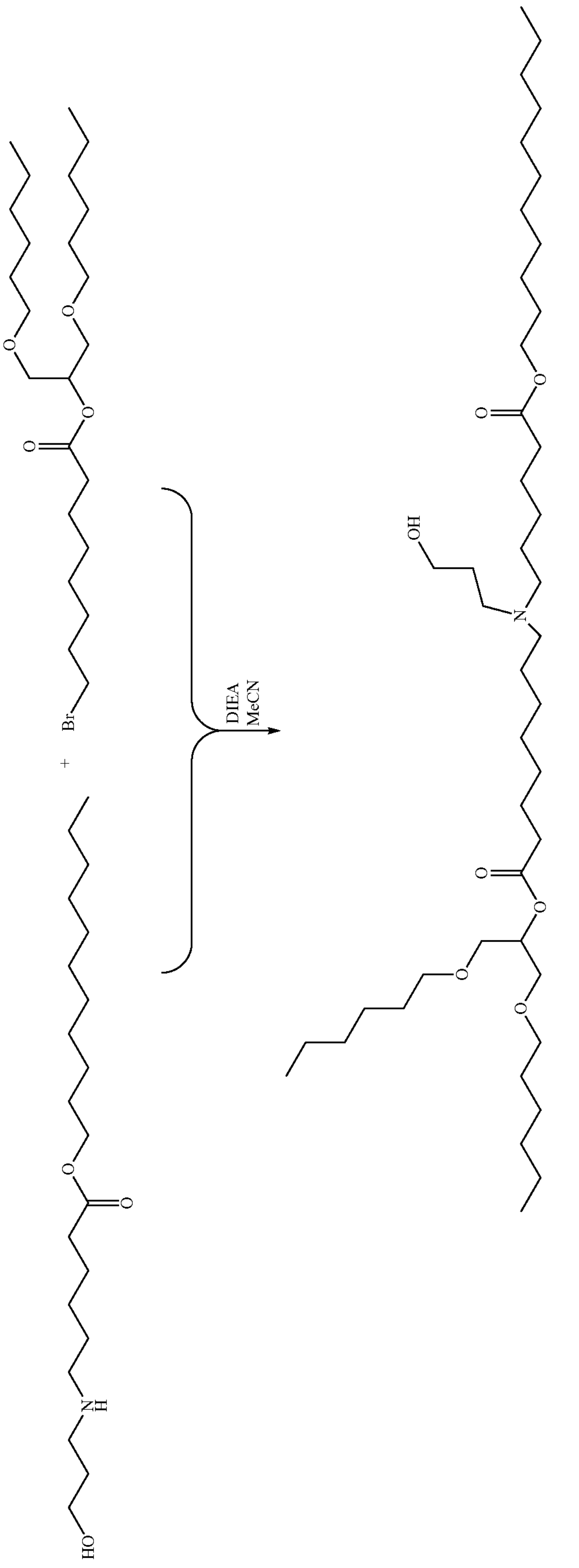
DIEA
MeCN

A16 was synthesized employing reaction steps similar to Example 1, 0.59 g oily product was obtained. MS(ES): m/z $(M+H)^+$ 727.63. $^1$HNMR ($CDCl_3$) δ:ppm: 5.10 (m, 1H), 4.05 (dd, 2H), 3.77 (t, 2H), 3.54 (dd, 4H), 3.46-3.38 (m, 4H), 3.19 (t, 2H), 3.01 (br, 4H), 2.32 (t, 4H), 1.66-1.27 (m, 52H), 0.88 (m, 9H).

Example 12—Synthesis of A17

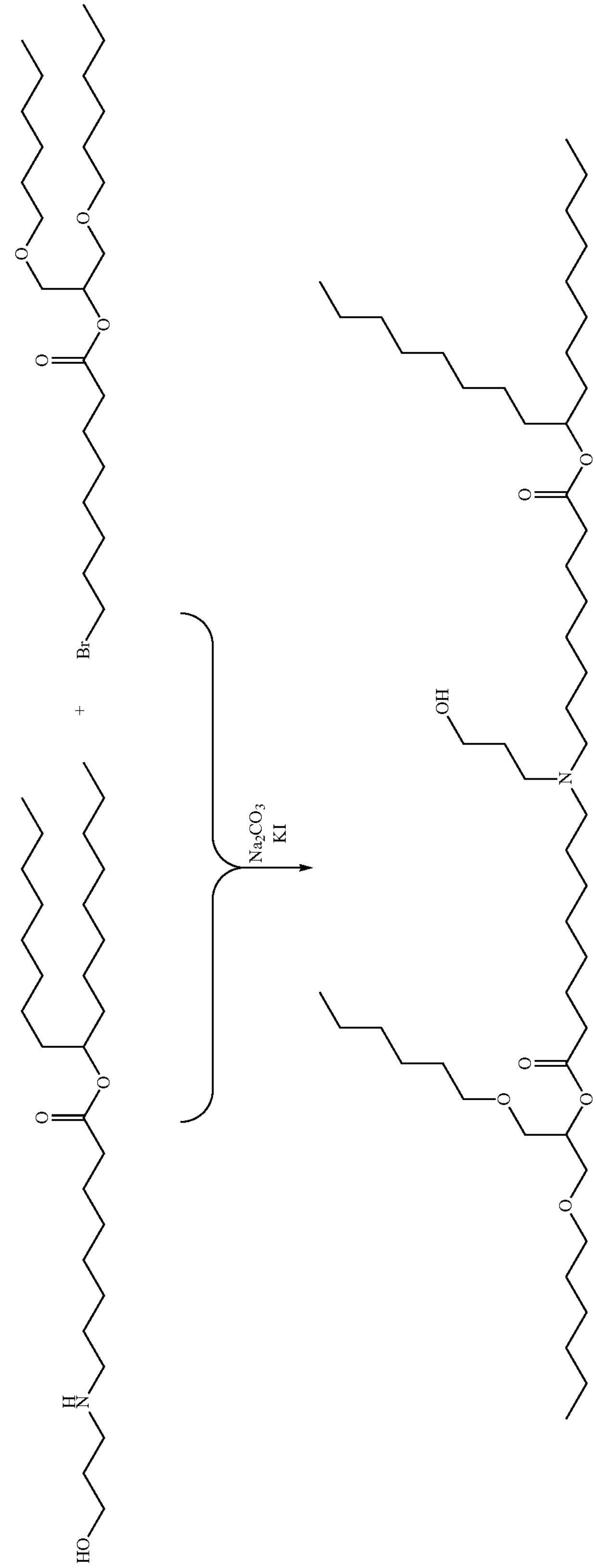
$Na_2CO_3$
KI

A17 was synthesized employing reaction steps similar to Example 1, 1.1 g oily product was obtained. MS(ES): m/z $(M+H)^+$ 839.76; $^1$HNMR ($CDCl_3$) δ:ppm: 5.12 (m, 1H), 4.86 (m, 1H), 3.79 (t, 2H), 3.55 (t, 4H), 3.41 (m, 4H), 2.67 (br, 2H), 2.44 (br, 4H), 2.32-2.26 (t, 4H), 1.62-1.25 (m, 66H), 0.88 (m, 12H).

Example 13—Synthesis of A18

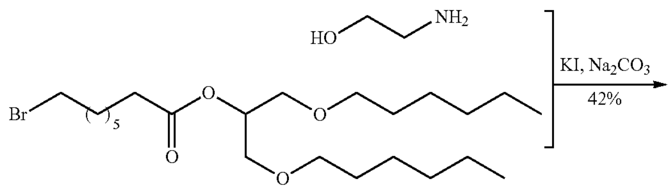

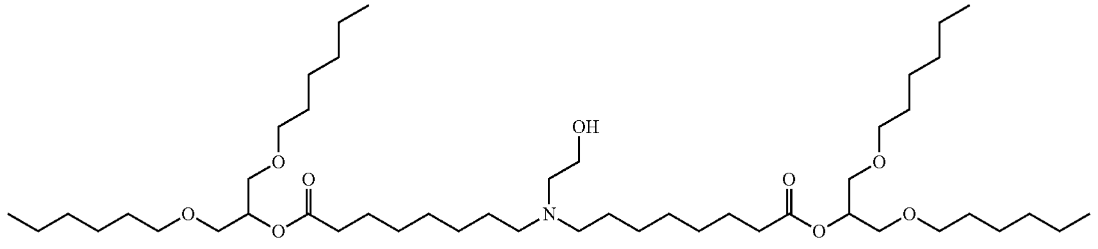

A18 was synthesized employing reaction steps similar to Example 1, 1.44 g oily product was obtained. $^1$HNMR ($CDCl_3$) δ: ppm. 5.11 (t, 2H), 3.57-3.37 (m, 18H), 2.57 (t, 2H), 2.44 (t, 4H), 2.32 (m, 4H), 1.62-1.27 (m, 52H), 0.88 (m, 12H), MS(ES): m/z $(M+H)^+$ 829.70.

Example 14—Synthesis of A19

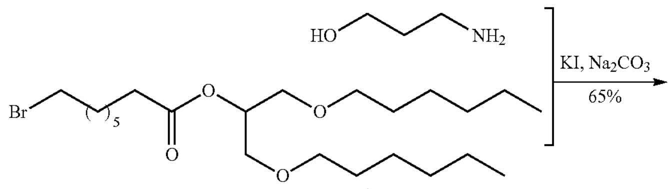

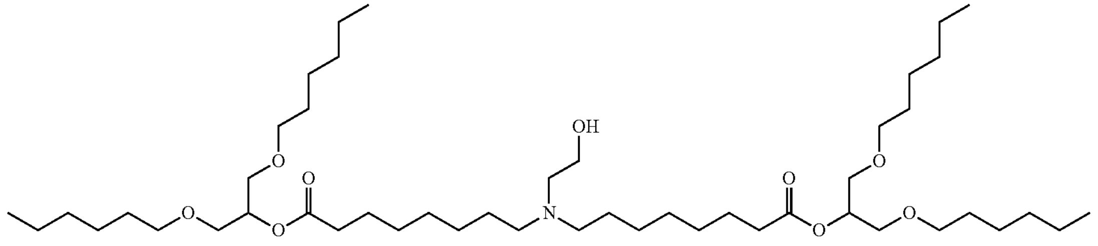

A19 was synthesized employing reaction steps similar to Example 1, 2.3 g oily product was obtained. $^1$HNMR ($CDCl_3$) δ: ppm. 5.06 (t, 2H), 3.72 (t, 2H), 3.50-3.33 (m, 16H), 2.27 (t, 2H), 2.25-2.24 (m, 8H), 1.56-1.19 (m, 52H), 0.88 (m, 12H), MS(ES): m/z $(M+H)^+$ 843.72.

Example 15—Synthesis of A20

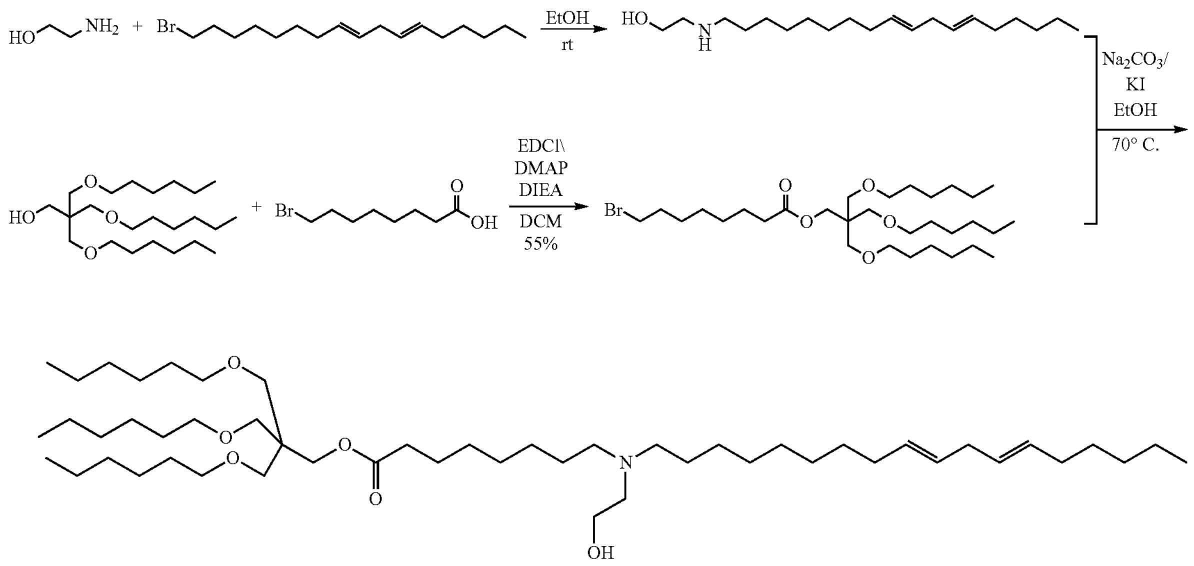

A20 was synthesized employing reaction steps similar to Example 1, 0.95 g oily product was obtained. MS (ES): m/z (MW) 821.75; $^1$H-NMR (400 MHz, $CDCl_3$) δ: ppm 5.29 (m, 4H), 4.03 (s, 2H), 3.51 (t, 2H), 3.30-3.27 (m, 12H), 2.70 (m, 2H), 2.57 (t, 2H), 2.46 (br, 4H), 2.21 (m, 2H), 1.30-1.19 (br. m, 52H), 0.89 (m, 12H).

Example 16—Synthesis of A21

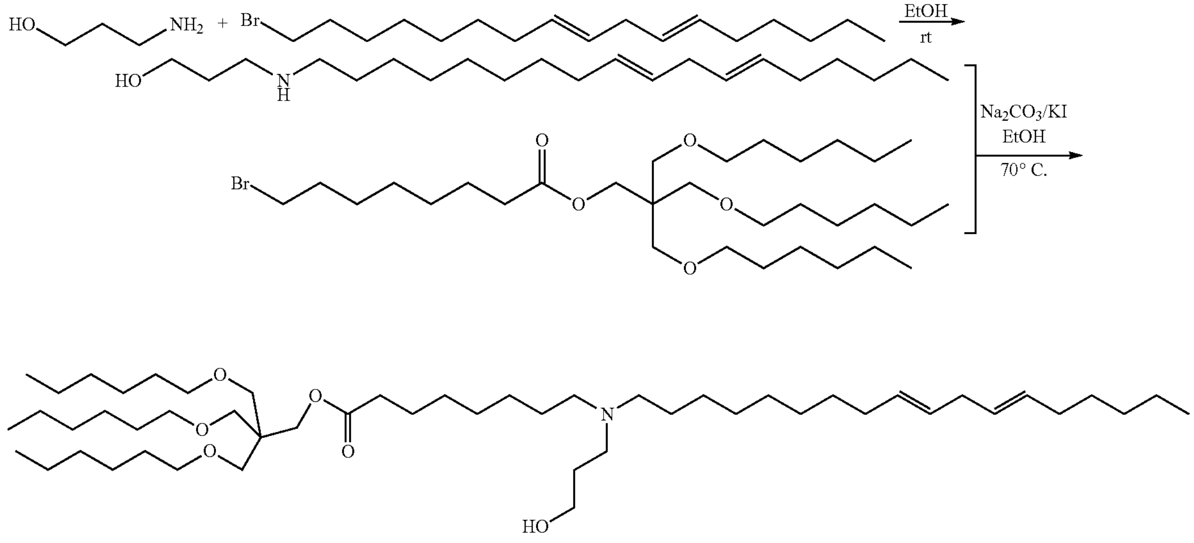

A21 was synthesized employing reaction steps similar to Example 1, 0.68 g oily product was obtained. MS (ES): m/z ($MH^+$) 835.76; $^1$H-NMR (400 MHz, $CDCl_3$) δ:ppm 5.35 (m, 4H), 4.10 (s, 2H), 3.79 (t, 2H), 3.30 (m, 12H), 2.76 (br, m, 4H), 2.50 (br, 4H), 2.28 (m, 2H), 2.05 (m, 4H), 1.61 (br, 4H), 1.57 (m, 4H), 1.54-1.24 (br. m, 54H), 0.88 (m, 12H).

Example 17—Synthesis of A22
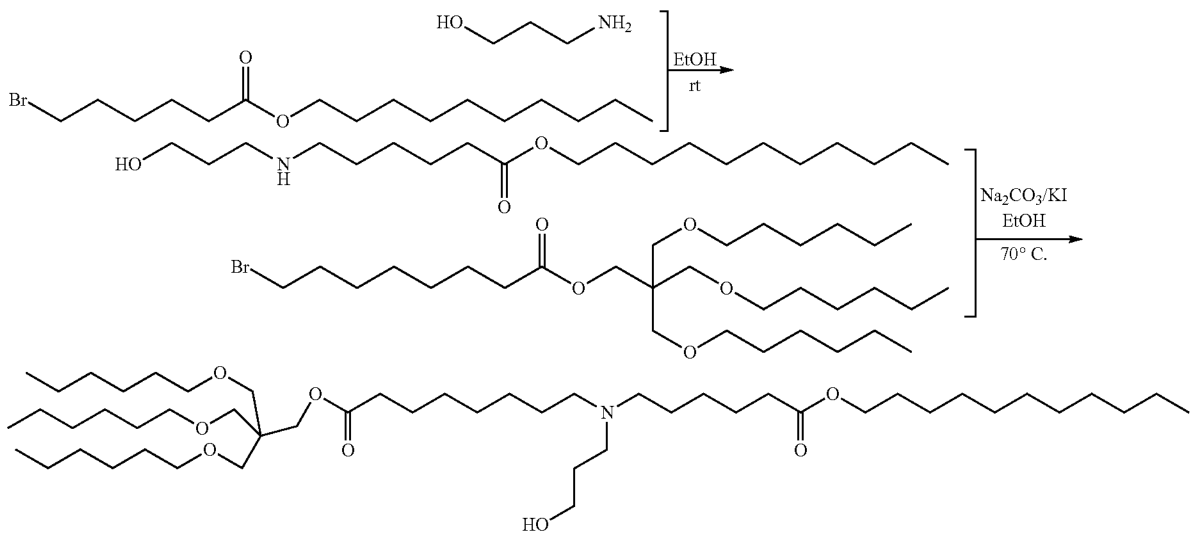
A22 was synthesized employing reaction steps similar to Example 1, 0.43 g oily product was obtained. $^1$HNMR (400 MHz, $CDCl_3$) δ:ppm. 4.03 (s, 2H), 3.98 (t, 2H), 3.72 (t, 2H), 3.28 (m, 12H), 2.65 (t, 2H), 2.45 (t, 4H), 2.25-2.20 (m, 4H), 1.66-1.19 (m, 60H), 0.83 (m, 12H), MS(ES): m/z $(M+H)^+$ 855.75.
Example 18—Synthesis of A23
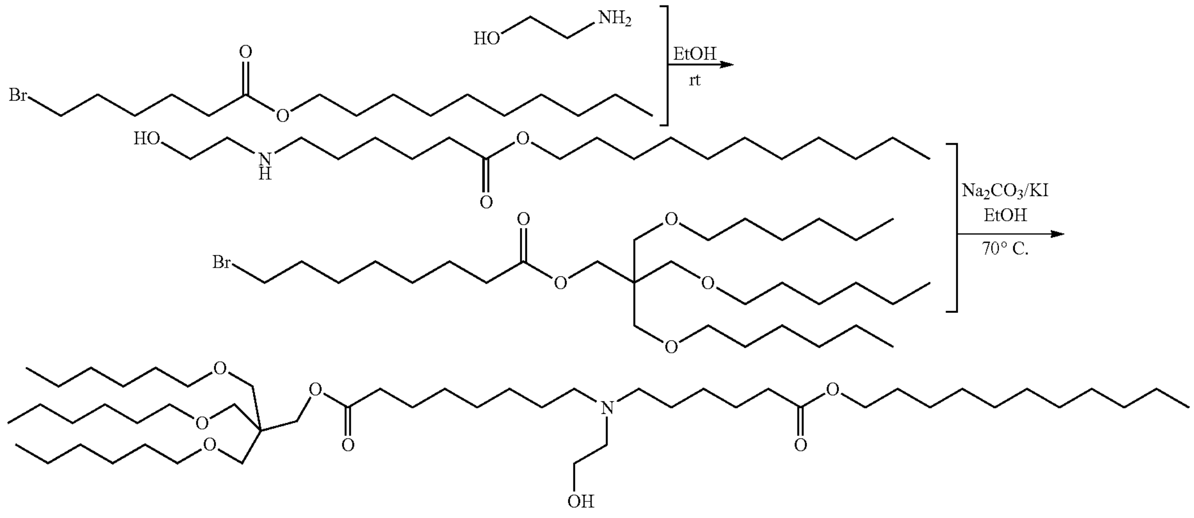
A23 was synthesized employing reaction steps similar to Example 1, 1.8 g oily product was obtained. $^1$HNMR (400 MHz, $CDCl_3$) δ: ppm. 4.10 (s, 2H), 4.06 (t, 2H), 3.56 (t, 2H), 3.36-3.34 (m, 12H), 2.61 (t, 2H), 2.49 (t, 4H), 2.30 (m, 4H), 1.67-1.26 (m, 58H), 0.88 (m, 12H), MS(ES): m/z $(M+H)^+$ 841.74.

Example 19—Synthesis of A24
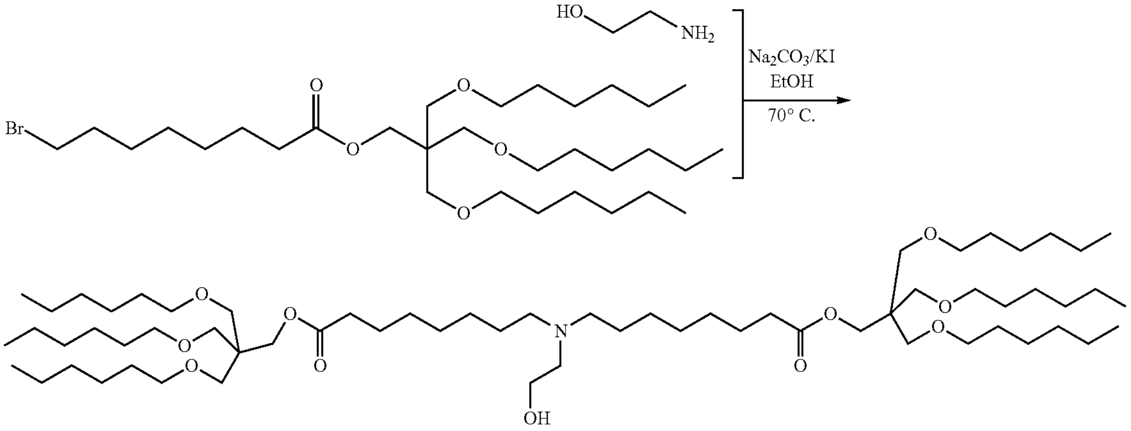
A24 was synthesized employing reaction steps similar to Example 1, 0.72 g oily product was obtained. $^1$HNMR (400 MHz, $CDCl_3$) δ: ppm. 4.10 (s, 4H), 3.67 (br, 2H), 3.35 (m, 24H), 2.80-2.50 (br, 6H), 2.28 (m, 4H), 1.67-1.23 (m, 68H), 0.89 (m, 18H), MS(ES): m/z $(M+H)^+$ 1085.94.
Example 20—Synthesis of A25

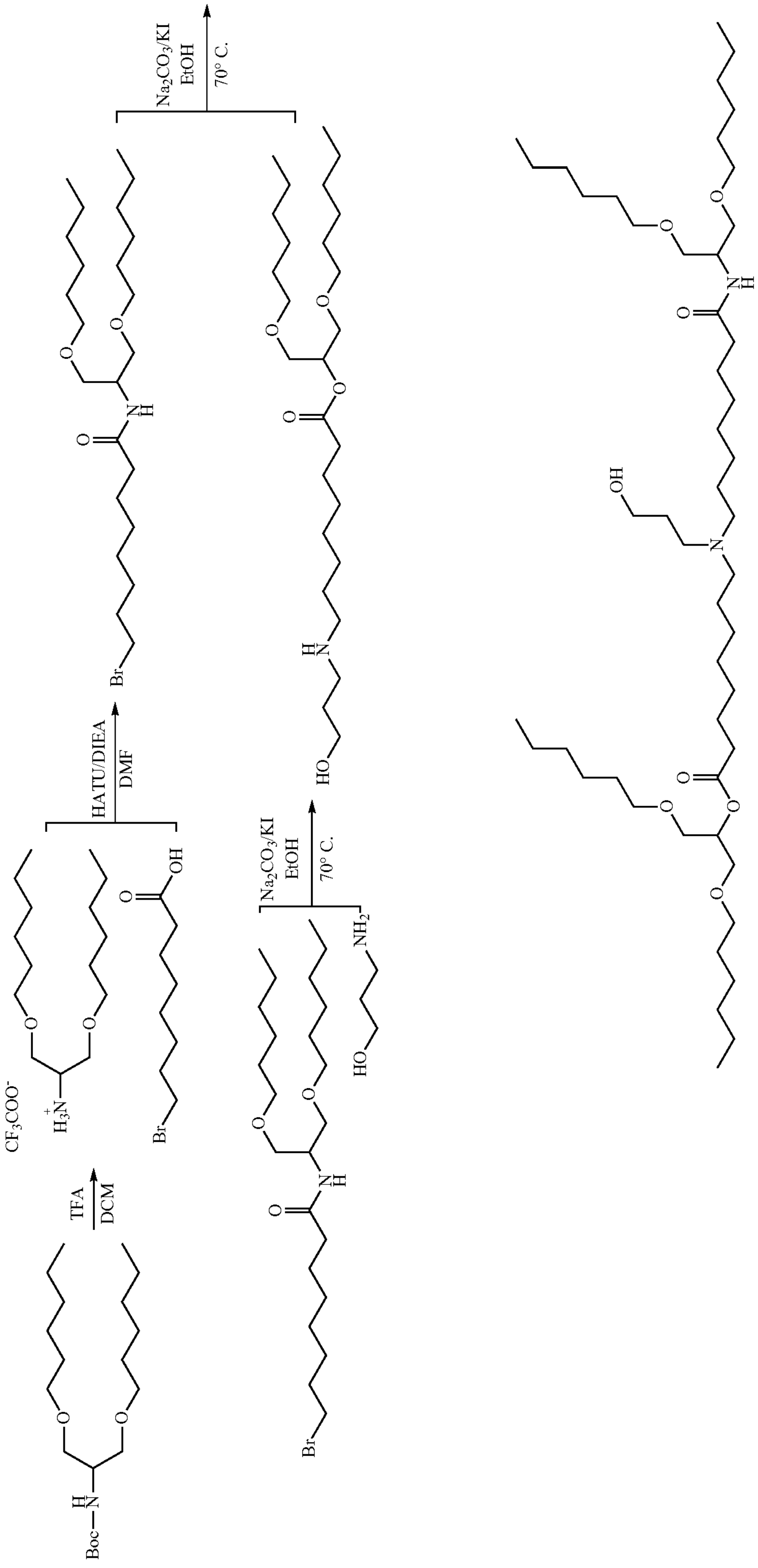
TFA
DCM
HATU/DIEA
DMF
$Na_2CO_3$/KI
EtOH
70° C.
$Na_2CO_3$/KI
EtOH
70° C.

A25 was synthesized employing reaction steps similar to Example 1, 0.3 g oily product was obtained. $^1$HNMR (400 MHz, $CDCl_3$) δ: ppm. 5.23 (m, 1H), 5.05 (t, 1H), 4.11 (br, 4H), 3.78 (t, 2H), 3.49-3.34 (br, m, 16H), 3.15 (t, 2H), 3.01 (t, 4H), 2.26 (m, 2H), 2.10 (m, 2H), 2.01 (m, 2H), 1.79-1.18 (br, m, 52H), 0.83 (br, m, 12H), MS(ES): m/z $(M+H)^+$ 842.73.

Example 21—Synthesis of A26

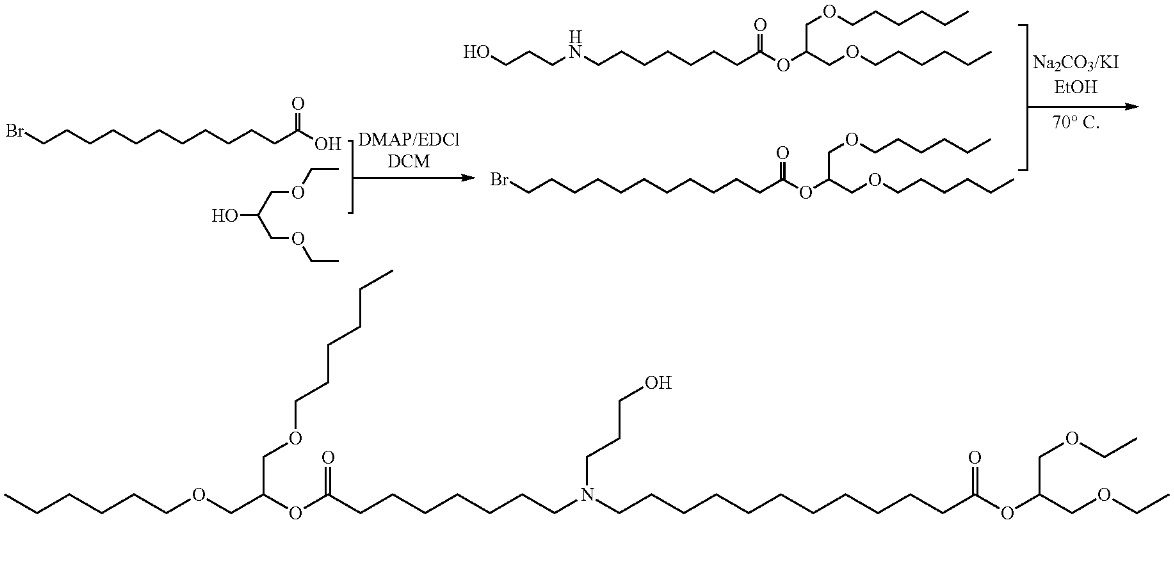

A26 was synthesized employing reaction steps similar to Example 1, 0.46 g oily product was obtained. $^1$HNMR (400 MHz, $CDCl_3$) δ:ppm. 5.03 (m, 2H), 3.75 (t, 2H), 3.48-3.34 (br, m, 16H), 2.91 (br, 2H), 2.72 (br, 4H), 2.27 (t, 4H), 1.85 (m, 2H), 1.58-1.10 (br, m, 48H), 0.81 (br, m, 6H), MS(ES): m/z $(M+H)^+$ 787.65.

Example 22—Synthesis of A27

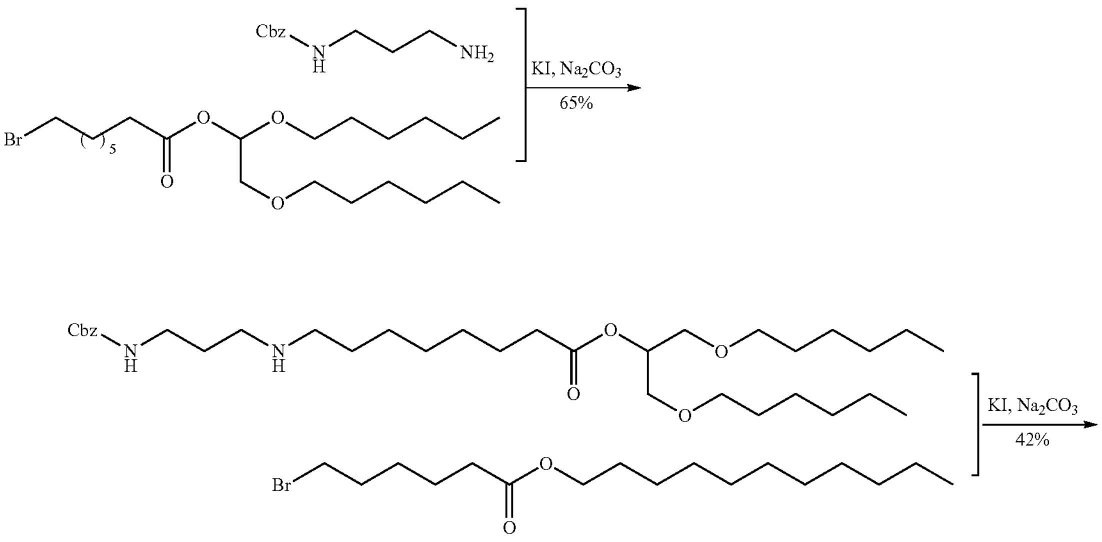

-continued

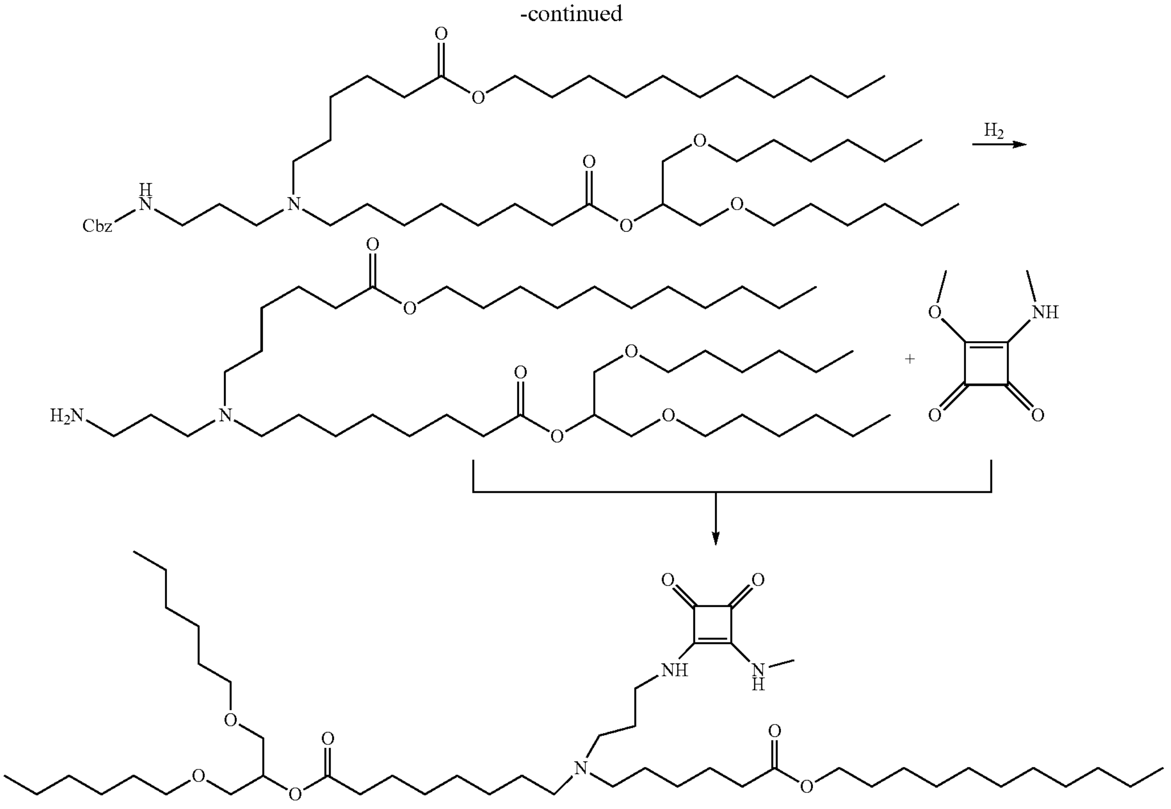

Cbz-1, 3-propylenediamineoctanoate was synthesized employing reaction steps similar to Example 1. Cbz-1, 3-propylenediamineoctanoate (3.5 g, 5.9 mmol), sodium carbonate anhydrous (0.94 g, 8.8 mmol), KI (0.19 g, 1.18 mmol) were soluted in 30 mL absolute ethanol and 30 mL absolute acetonitrile, then bromide was added and reacted together at 75° C. for 24 h. After the reaction was completed, the solvent was removed by concentrating, the reaction was diluted with 200 mL dichloromethane, washed with 200 mL water, extracted, the organic layer was dried over, concentrated, and passed through a silica gel column for purification (DCM:MeOH=3%-10%), oily Cbz-amine product was obtained. Cbz-amine (2.1 g, 2.43 mmol) was soluted in 20 mL absolute methanol and 20 mL ethyl acetate, then palladium (0.35 g, 10%) was added, after hydrogen was replaced for three times, hydrogenation occurred at room temperature for 20 h. After the reaction was completed, the palladium was removed by filtration, the solvent was concentrated and removed, extracted and the amine product was obtained. The obtained amine product (1.1 g, 1.51 mmol) was soluted in 20 mL absolute ethanol, Ketone-methylamine (0.22 g, 1.51 mmol) was added, solution was stirred and reacted at room temperature for 20 h. After the reaction was completed, the solvent was concentrated and removed, the filtrate was dried over, concentrated and passed through a silica gel column for purification (DCM:MeOH=3%-10%), A27 was obtained (0.6 g oily product). $^1$HNMR (d-DMSO) δ: ppm. 4.99 (p, 1H), 3.98 (t, 2H), 3.50-3.31 (m, 8H), 3.10 (d, 3H), 2.49 (dt, 8H), 2.26 (m, 4H), 1.52 (dd, 6H), 1.43 (m, 6H), 1.26 (m, 40H), 0.84 (m, 9H), MS(E S): m/z $(M+H)^+$ 835.66.

Example 23—Synthesis of A28

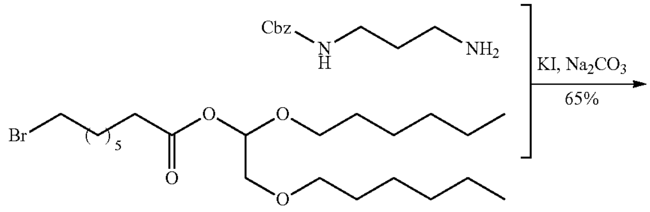

-continued
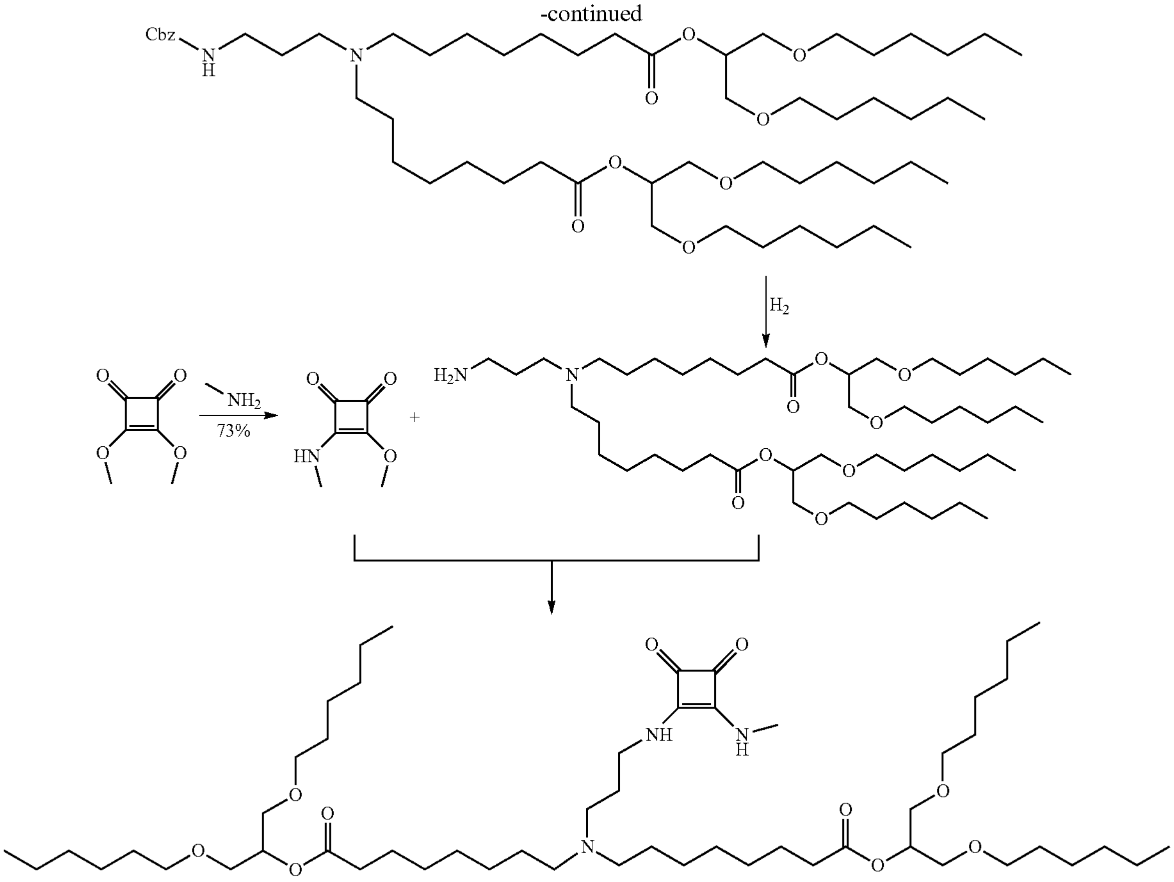
A28 was synthesized employing reaction steps similar to Example 22, 1.3 g oily product was obtained. $^1$HNMR ($CDCl_3$) δ:ppm. 5.04 (t, 2H), 3.61 (t, 2H), 3.50-3.31 (m, 16H), 3.21 (s, 3H), 2.71 (t, 2H), 2.55 (t, 4H), 2.28-2.24 (m, 4H), 1.86-1.19 (m, 54H), 0.82 (m, 12H), MS(ES): m/z $(M+H)^+$ 951.75.
Example 24—Synthesis of A29
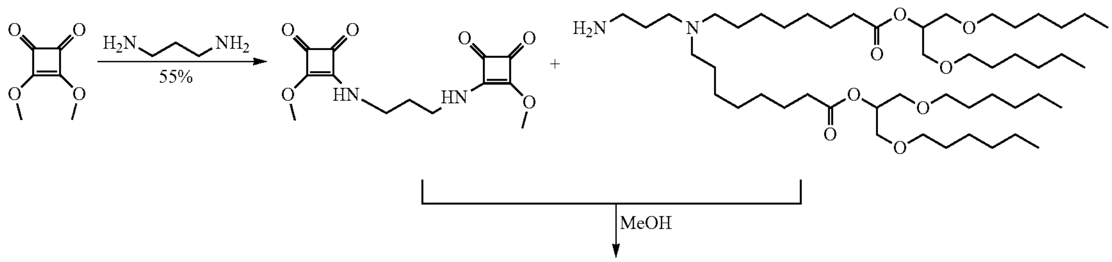

-continued
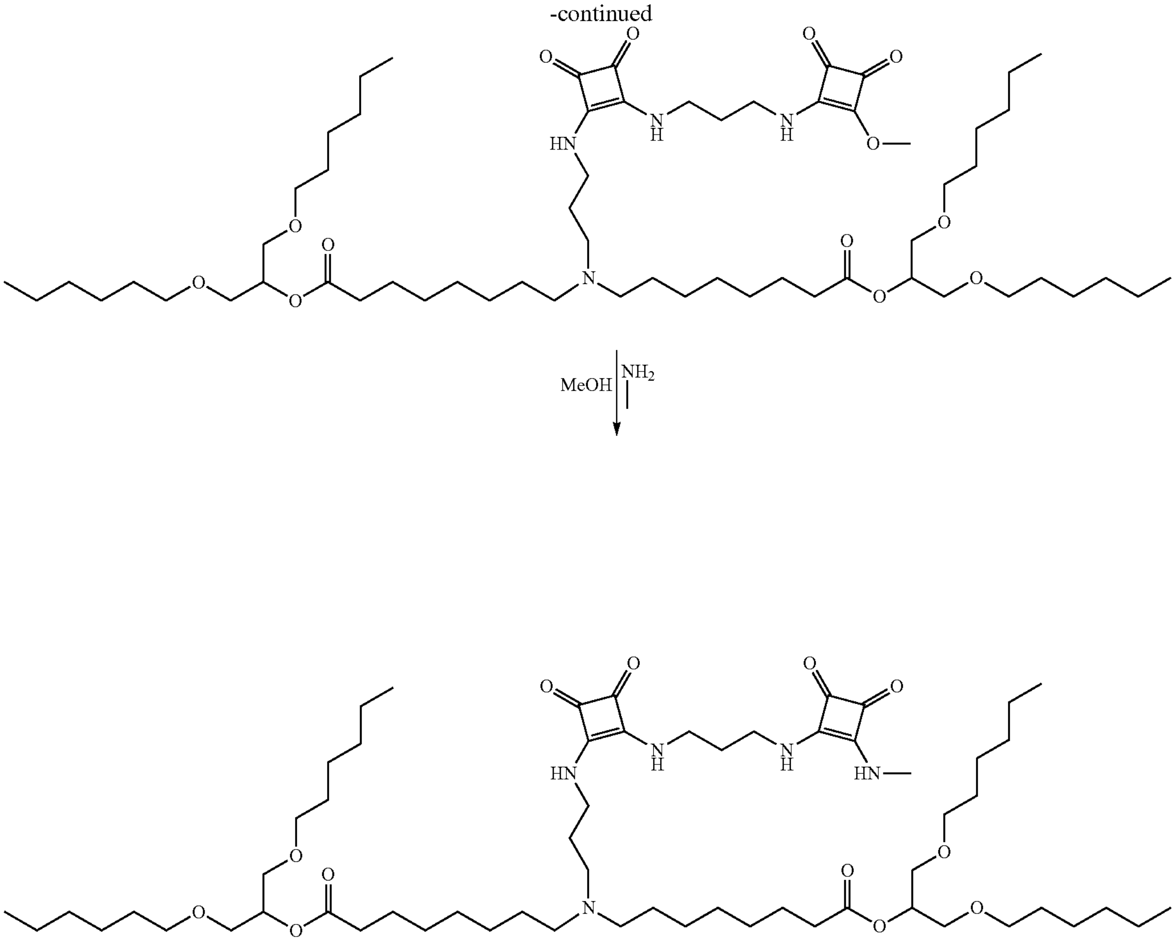
A29 was synthesized employing reaction steps similar to Example 22, 0.11 g oily product was obtained. $^1$HNMR (d-DMSO) δ:ppm. 5.00 (m, 2H), 3.60-3.30 (m, 16H), 3.11 (s, 3H), 2.63-2.49 (m, 10H), 2.36 (m, 2H), 2.26 (m, 4H), 1.80 (m, 2H), 1.46-1.26 (m, 54H), 0.85 (t, 12H), MS(ES): m/z $(M+H)^+$ 1103.81.
Example 25—Synthesis of A30
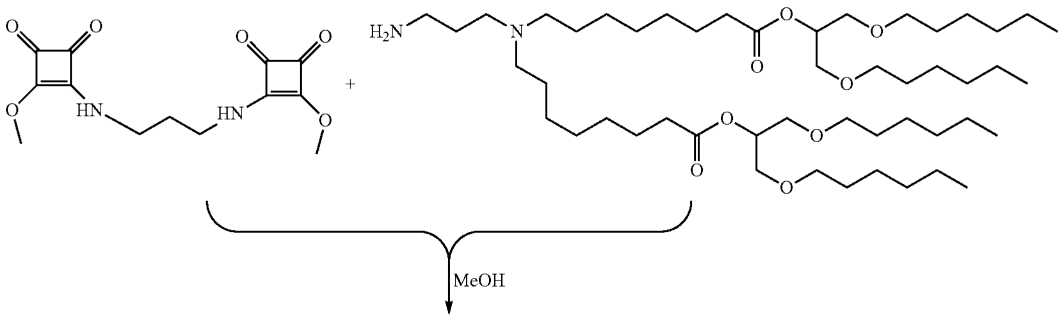

-continued
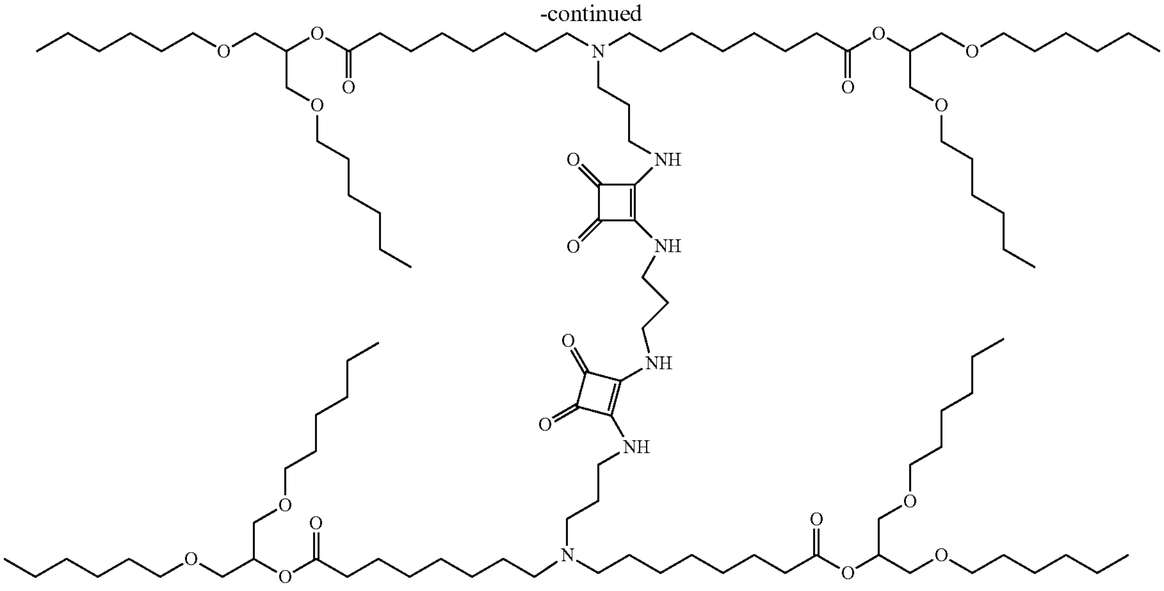
A30 was synthesized employing reaction steps similar to Example 22, 0.34 g oily product was obtained. $^1$HNMR (d-DMSO) δ:ppm. 4.99 (m, 4H), 3.60-3.30 (m, 32H), 2.63-2.40 (m, 20H), 2.25 (m, 8H), 1.80-1.20 (m, 110H), 0.81 (m, 24H), MS(ES): m/z $(M+H)^+$1915.5.
Example 26—Synthesis of A31
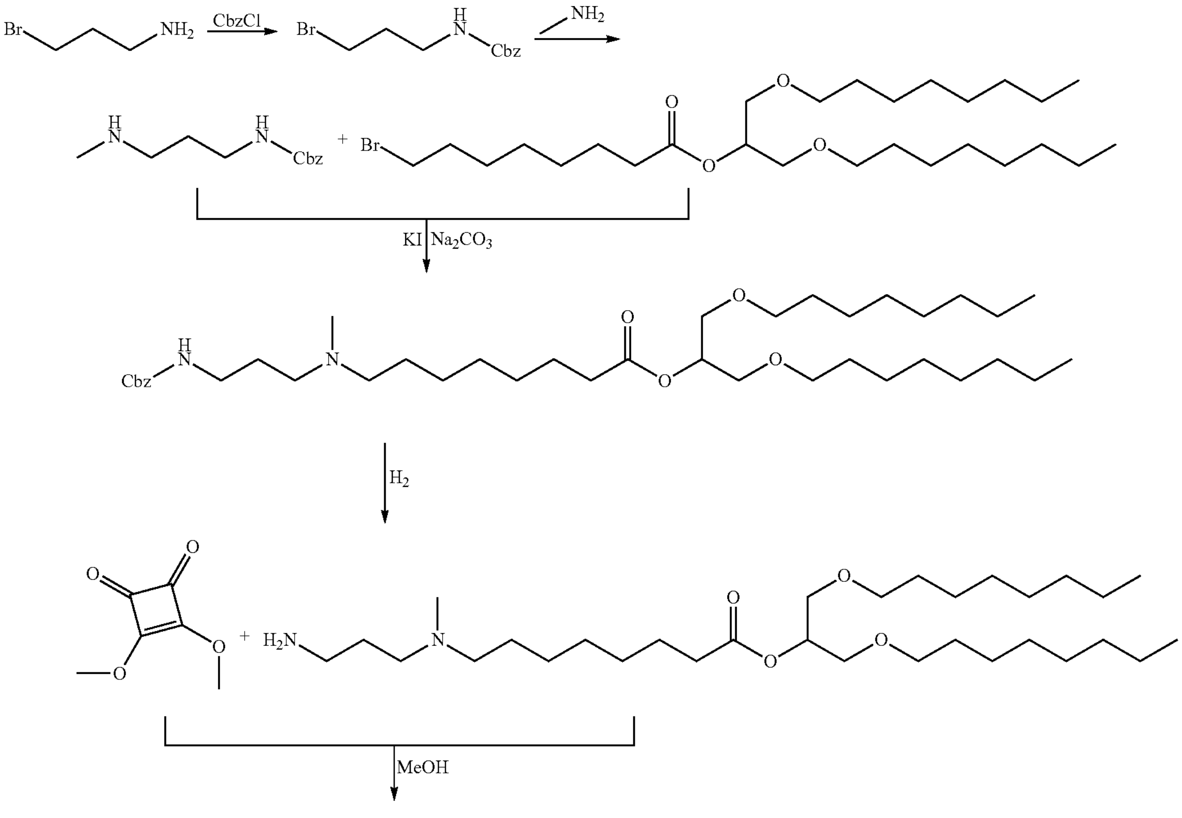

-continued
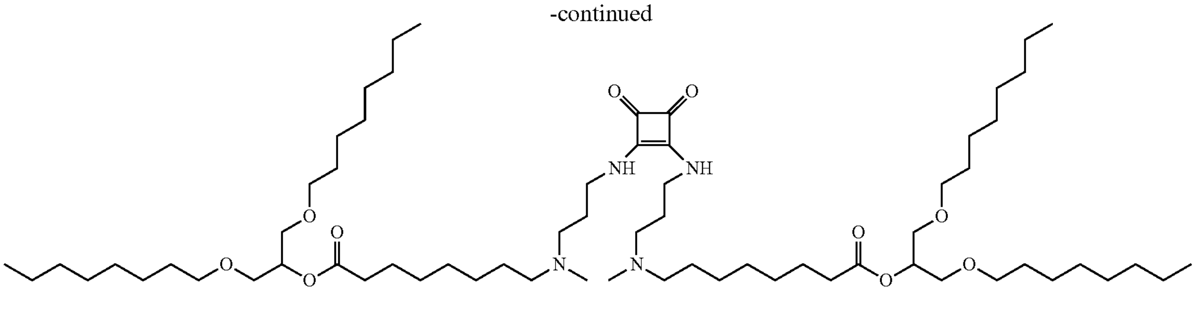
A31 was synthesized employing reaction steps similar to Example 22, 0.7 g oily product was obtained. $^1$HNMR (d-DMSO) δ: ppm. 5.05 (m, 2H), 3.60-3.30 (m, 20H), 2.63-2.40 (m, 12H), 2.2 (m, 6H), 1.80-1.20 (m, 64H), 0.85 (m, 12H), MS(ES): m/z $(M+H)^+$1134.95.
Example 27—Synthesis of A32
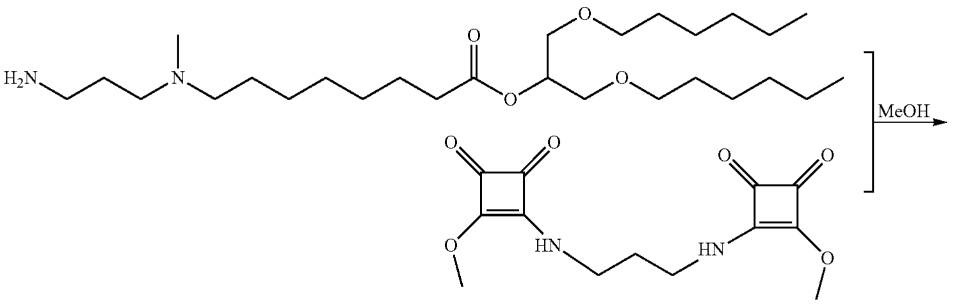
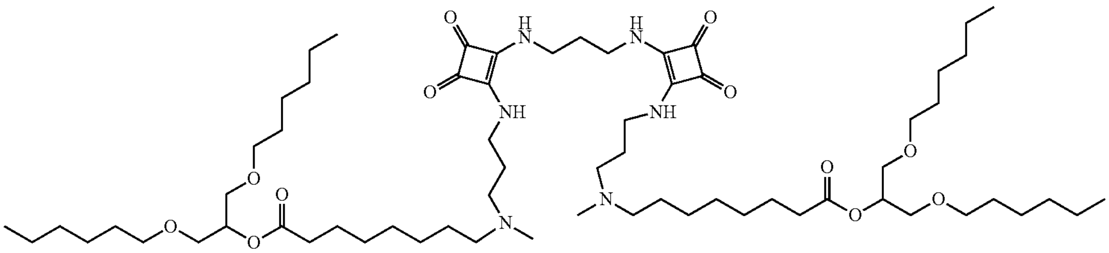
A32 was synthesized employing reaction steps similar to Example 22, 1.5 g oily product was obtained. $^1$HNMR (d-DMSO) δ: ppm. 5.1 (m, 2H), 3.60-3.30 (m, 24H), 2.5 (m, 4H), 2.4 (m, 4H), 2.3 (m, 4H), 2.2 (m, 6H), 1.95 (m, 2H), 1.8 (m, 2H), 1.5-1.6 (m, 8H), 1.2-1.4 (m, 48H), 0.9 (m, 8H), MS(ES): m/z $(M+H)^+$ 1174.88.
Example 28—Synthesis of A34
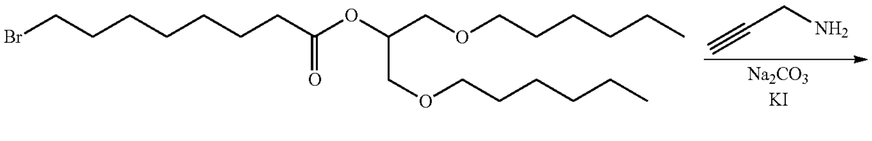

-continued

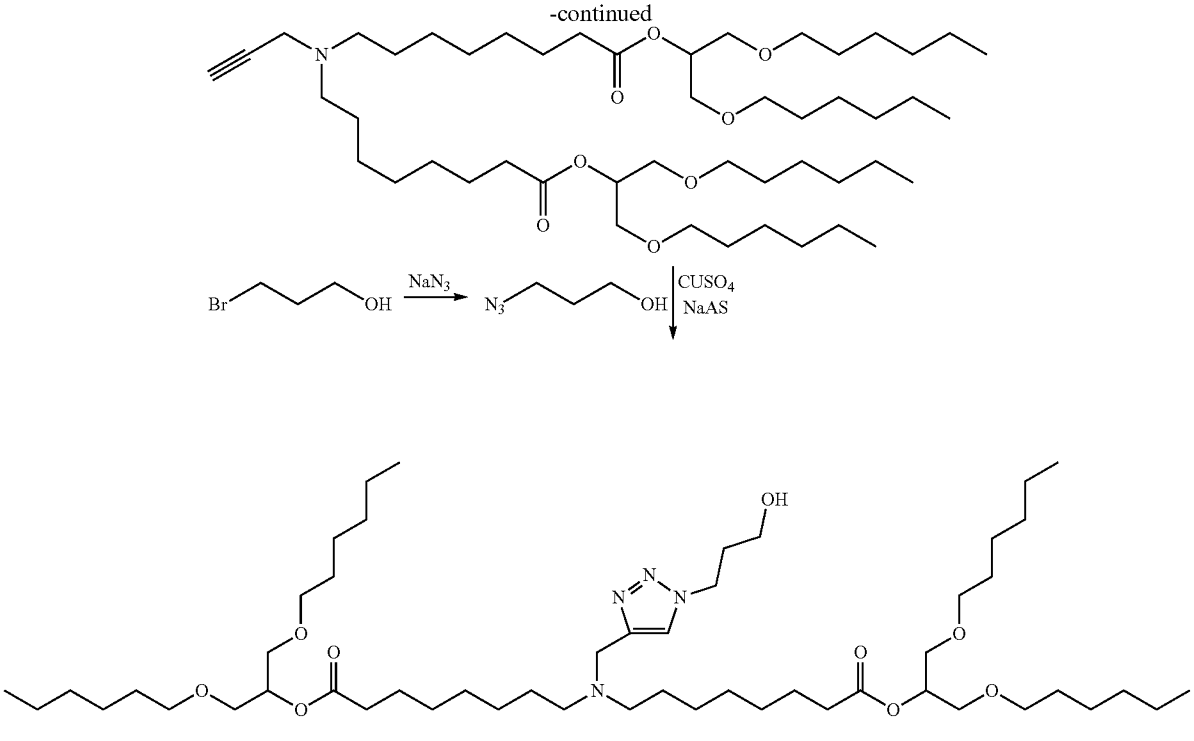

Alkynyl lipid intermediate was synthesized employing reaction steps similar to Example 1. Bromooxy ether ester (11 g), sodium carbonate (2.5 g), KI (0.4 g) were dissolved in 50 mL acetonitrile, alkylamine (0.65 g) was added. After the reaction was completed, it was concentrated to remove acetonitrile, stirred and extracted with 150 mL of ethyl acetate and water, the organic layer was dried over, concentrated, and passed through a silica gel column for purification (PE:EA=10:1-5:1), for obtaining the alkynyl lipid intermediate.

Steps to prepare A34: 3-azidopropanol-1 compound (0.5 g), anhydrous copper sulfate (0.15 g), sodium ascorbate (0.24 g) and alkynyl compound (0.08 g) were dissolved in 10 mL THF and 10 mL water, after the reaction occurred at room temperature, it was concentrated to remove THF, diluted with 100 mL dichloromethane, filtered to remove unsolved material, filtrate was stirred and extracted with water, the organic layer was dried over, concentrated, and passed through a silica gel column for purification (DCM: MeOH=1%-2%), 0.39 g A34 was obtained. $^1$HNMR ($CDCl_3$) δ: ppm. 7.56 (s, 1H), 5.12 (p, 2H), 4.50 (m, 2H), 3.77 (s, 2H), 3.62-3.43 (m, 18H), 2.44 (s, 4H), 2.32 (t, 4H), 2.13 (tt, 2H), 1.70-1.50 (m, 16H), 1.26 (m, 36H), 0.87 (m, 12H); MS(ES): m/z $(M+H)^+$ 925.37.

Example 29—Synthesis of A35

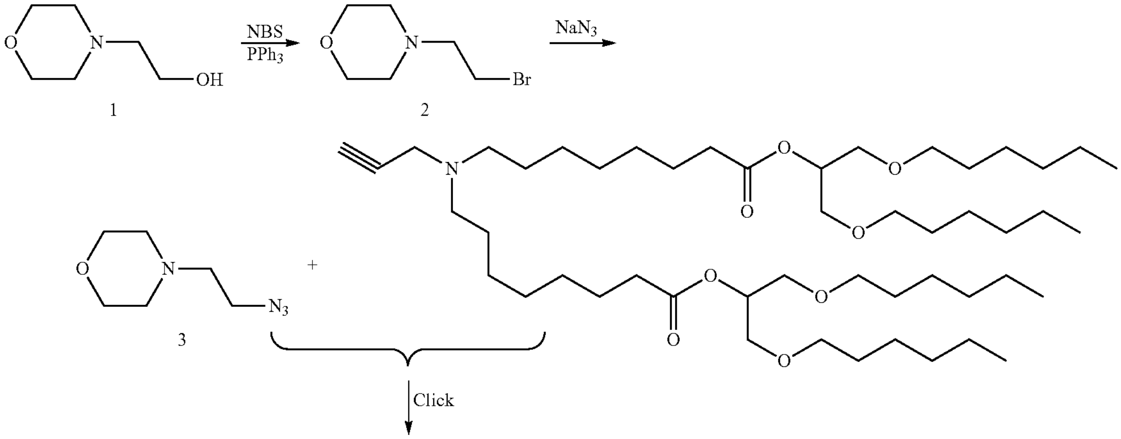

1

2

3

-continued
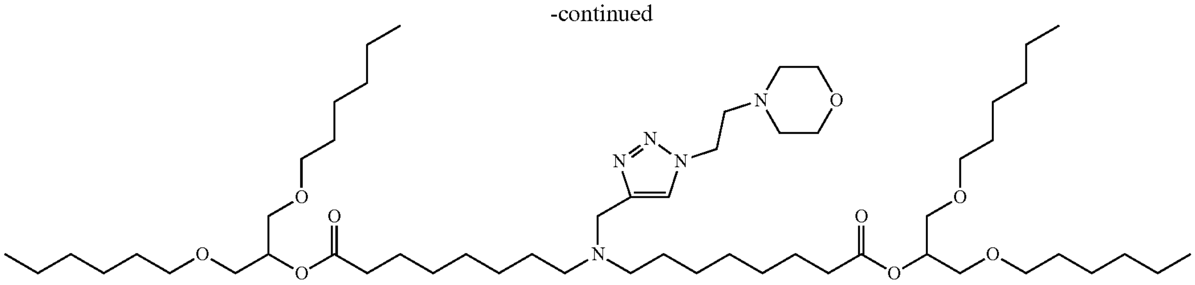
A35 was synthesized employing reaction steps similar to Example 28, 2.2 g product was obtained. $^1$HNMR ($CDCl_3$) δ:ppm. 7.50 (d, 1H), 5.11 (p, 2H), 4.45 (t, 2H), 3.77 (s, 2H), 3.68-3.43 (m, 20H), 2.82 (t, 2H), 2.49 (m, 4H), 2.41 (s, 4H), 2.32 (t, 4H), 1.70-1.50 (m, 20H), 1.26 (m, 32H), 0.88 (m, 12H); MS(ES): m/z $(M+H)^+$ 980.45.
Example 30—Synthesis of A36

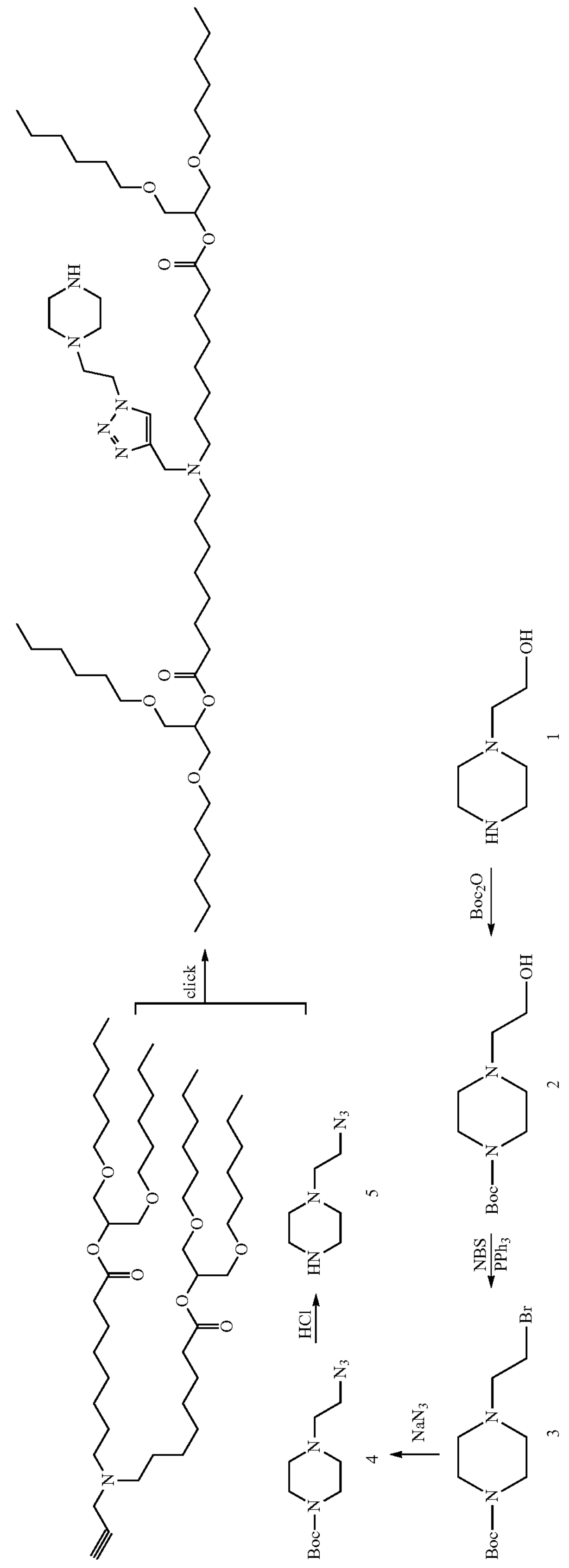
click
$Boc_2O$
NBS
$PPh_3$
$NaN_3$
HCl
1
2
3
4
5

A36 was synthesized employing reaction steps similar to Example 28, 2.4 g product was obtained. $^{1}H$ NMR (500 MHz, DMSO) δ: ppm 7.86 (s, 1H), 5.00 (p, J=5.2 Hz, 2H), 4.41 (t, J=6.3 Hz, 2H), 3.62 (s, 2H), 3.55-3.41 (m, 10H), 3.42-3.35 (m, 8H), 2.68 (d, J=5.9 Hz, 4H), 2.36 (s, 4H), 2.32-2.27 (m, 4H), 2.25 (t, J=7.3 Hz, 4H), 1.55-1.48 (m, 4H), 1.46-1.43 (m, 6H), 1.41-1.36 (m, 4H), 1.25 (dd, J=16.2, 4.5 Hz, 38H), 1.10 (s, 1H), 0.84 (t, J=6.9 Hz, 12H)$_o$ MS(ES): m/z $(M+H)^+$ 979.47.

Example 31—Synthesis of A37

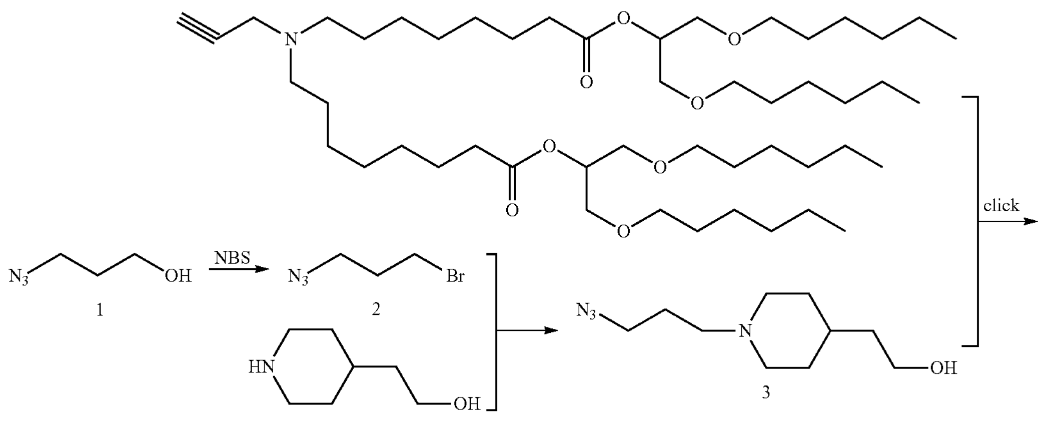

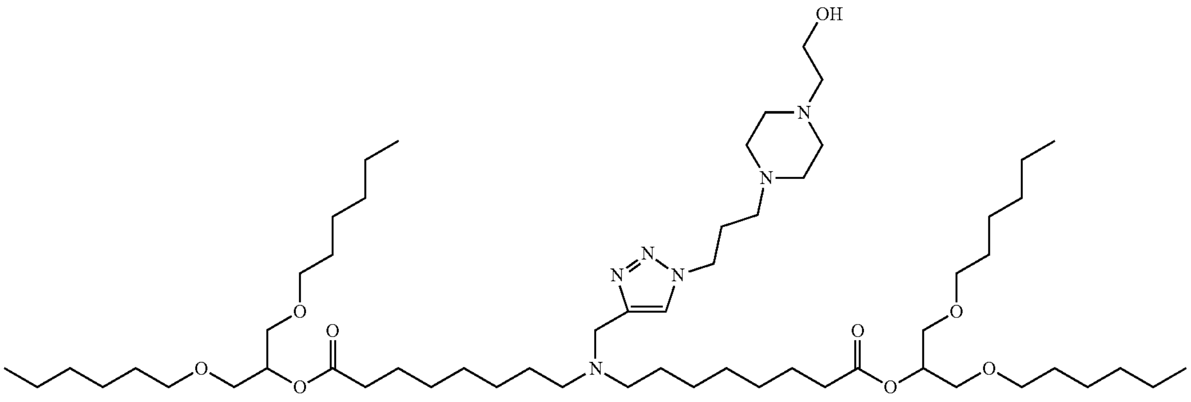

A37 was synthesized employing reaction steps similar to Example 28, 1.7 g product was obtained. $^{1}HNMR$ ($CDCl_3$) δ:ppm. 7.59 (d, 1H), 5.10 (p, 2H), 4.46 (t, 2H), 3.75 (s, 2H), 3.75-3.43 (m, 20H), 2.94-2.87 (t, 4H), 2.69-2.43 (m, 4H), 2.41 (s, 4H), 2.33 (t, 4H), 1.70-1.50 (m, 22H), 1.26 (m, 32H), 0.88 (m, 12H); MS(ES): m/z $(M+H)^+$1037.54.

Example 32—Synthesis of A38
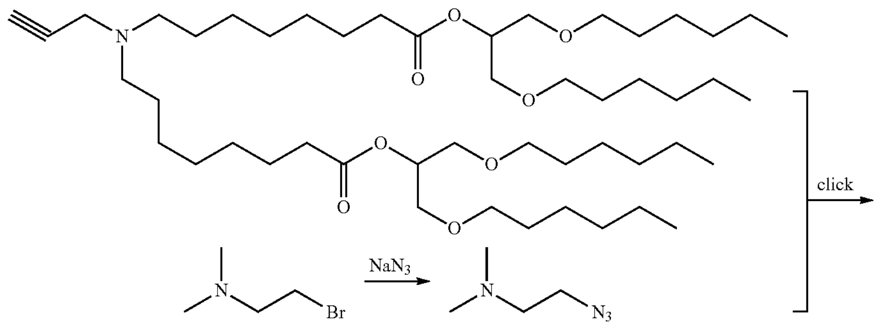
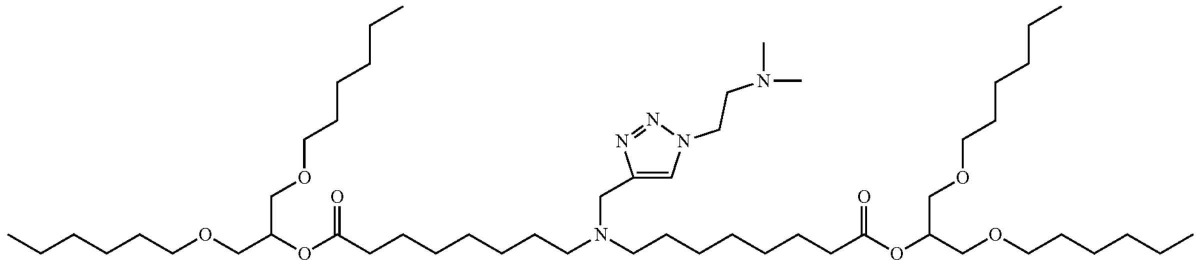
A38 was synthesized employing reaction steps similar to Example 28, 2.5 g product was obtained. $^{1}$HNMR ($CDCl_3$) δ:ppm. 7.53 (d, 1H), 5.11 (p, 2H), 4.42 (t, 2H), 3.76 (s, 2H), 3.68-3.41 (m, 20H), 2.83 (t, 2H), 2.49 (s, 6H), 2.32 (t, 4H), 1.70-1.50 (m, 20H), 1.26 (m, 32H), 0.87 (m, 12H); MS(ES): m/z $(M+H)^+$ 953.45.
Example 33—Synthesis of A39
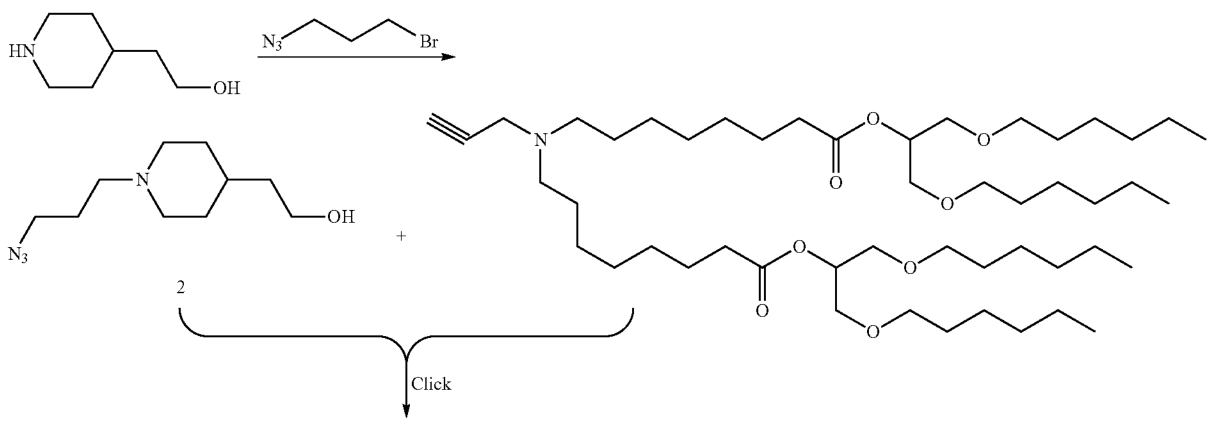

-continued
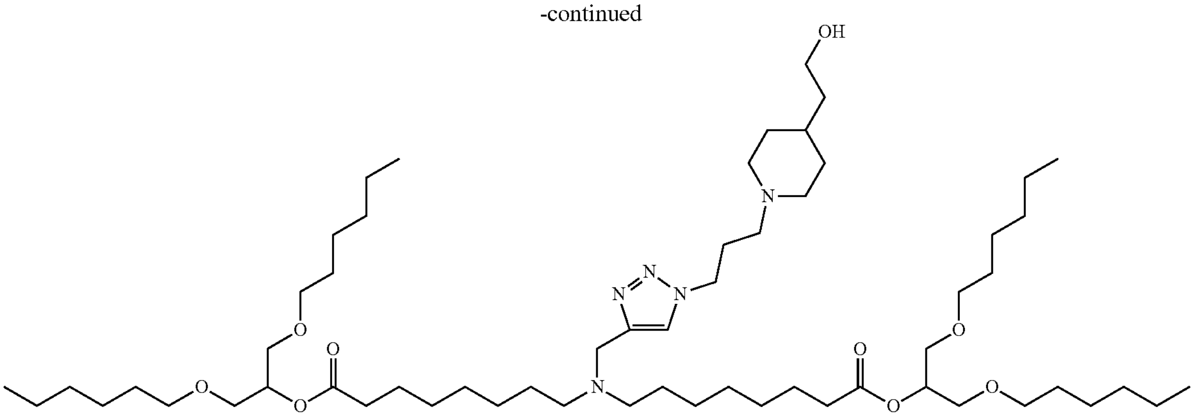
A39 was synthesized employing reaction steps similar to Example 28, 1.7 g product was obtained. $^1$HNMR ($CDCl_3$) δ:ppm. 7.59 (d, 1H), 5.11 (p, 2H), 4.47 (t, 2H), 3.73 (s, 2H), 3.70-3.41 (m, 24H), 2.78 (t, 2H), 2.51 (4, 4H), 2.42 (m, 2H), 2.32 (t, 4H), 1.59-1.25 (m, 59H), 0.87 (m, 12H); MS(ES): m/z $(M+H)^+$ 1036.56.
Example 34—Synthesis of A40

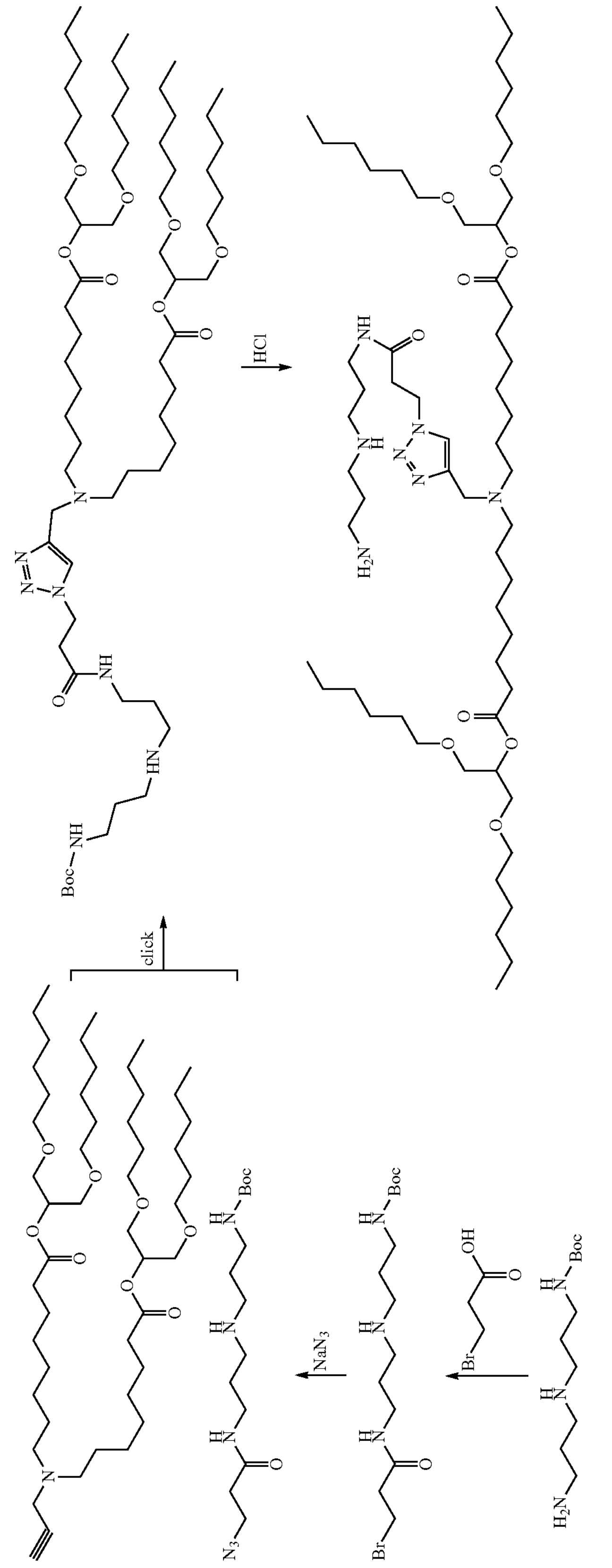
click
HCl
NaN3

A40 was synthesized employing reaction steps similar to Example 28, 1.4 g product was obtained. $^{1}$HNMR ($CDCl_3$) δ: ppm. 7.53 (d, 1H), 5.11 (p, 2H), 4.47 (t, 2H), 3.72 (s, 2H), 3.70-3.40 (m, 22H), 2.66 (t, 2H), 2.65-2.55 (m, 6H), 2.32 (t, 4H), 1.59-1.25 (m, 44H), 0.87 (m, 12H); MS(ES): m/z $(M+H)^+$ 1052.54.

Example 35—Synthesis of A42

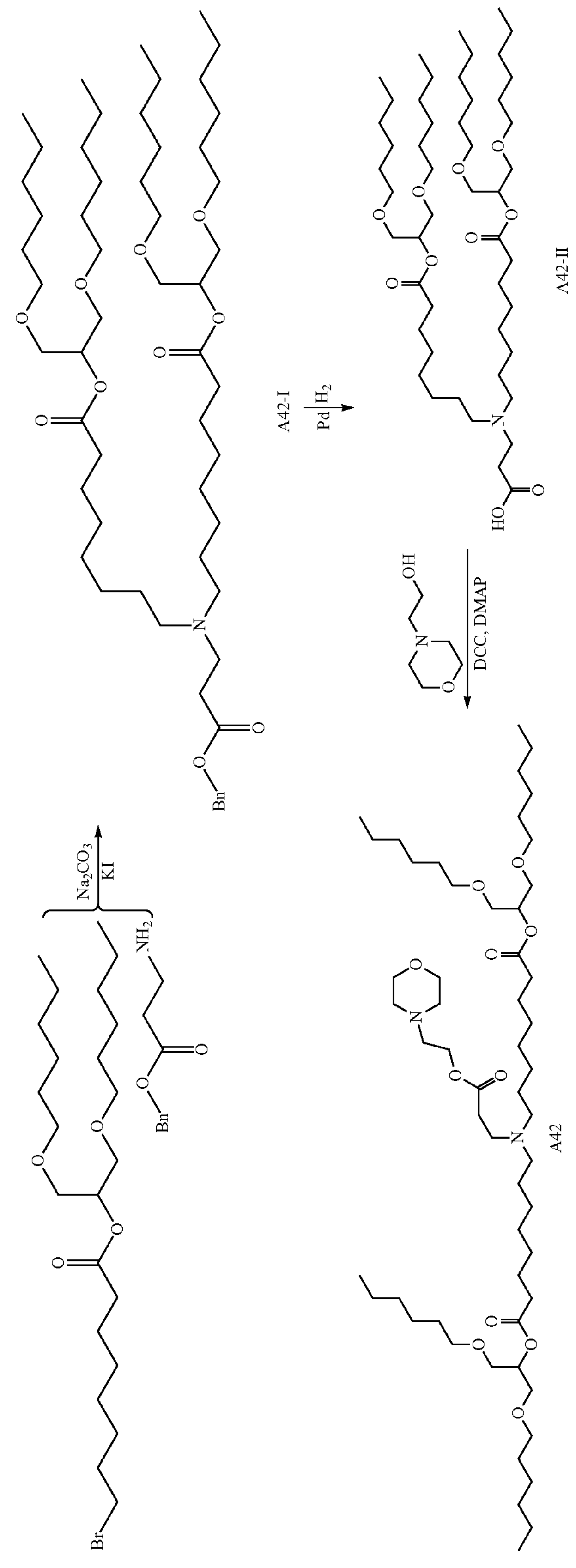
$Na_2CO_3$
KI
A42-I
Pd | $H_2$
A42-II
DCC, DMAP
A42

Alkynyl lipid intermediate was synthesized employing reaction steps similar to Example 1. Bromooxy ether ester (10.6 g), sodium carbonate (2.42 g), KI (0.4 g) were dissolved in 50 mL acetonitrile, benzyl-alanine (2.04 g) was added, after reflux reaction was completed, it was concentrated to remove acetonitrile, stirred and extracted with ethyl acetate and water, the organic layer was dried over, concentrated, and passed through a silica gel column for purification (DCM:MeOH=2%-3%), 7.5 g A42-I was obtained.

A42-I intermediate (2 g), palladium on carbon (0.5 g) were dissolved in 50 mL methanol, after the hydrogenation room temperature reaction was completed, it was filtered to remove the palladium on carbon, the filtrate was dried over, concentrated to obtain 1.7 g A42-II.

Steps to prepare A42: A42-II intermediate (1.5 g), DCC (0.54 g), DMAP (0.21 g) were dissolved in 50 mL dichloromethane, morpholine ethanol (0.23 g) was added, after room temperature reaction was completed, it was stirred and extracted with dichloromethane and water, the organic layer was dried over, concentrated, and passed through a silica gel column for purification (DCM:MeOH=1%-3%), 1.1 g A42 was obtained. $^1$HNMR ($CDCl_3$) δ: ppm. 5.12 (p, 2H), 4.41 (t, 2H), 3.76 (t, 2H), 3.55-3.40 (m, 20H), 3.01-2.76 (m, 10H), 2.49 (t, 6H), 2.32 (t, 4H), 1.59-1.25 (m, 52H), 0.87 (m, 12H); MS(ES): m/z $(M+H)^+$ 971.44.

Example 36—Synthesis of A43

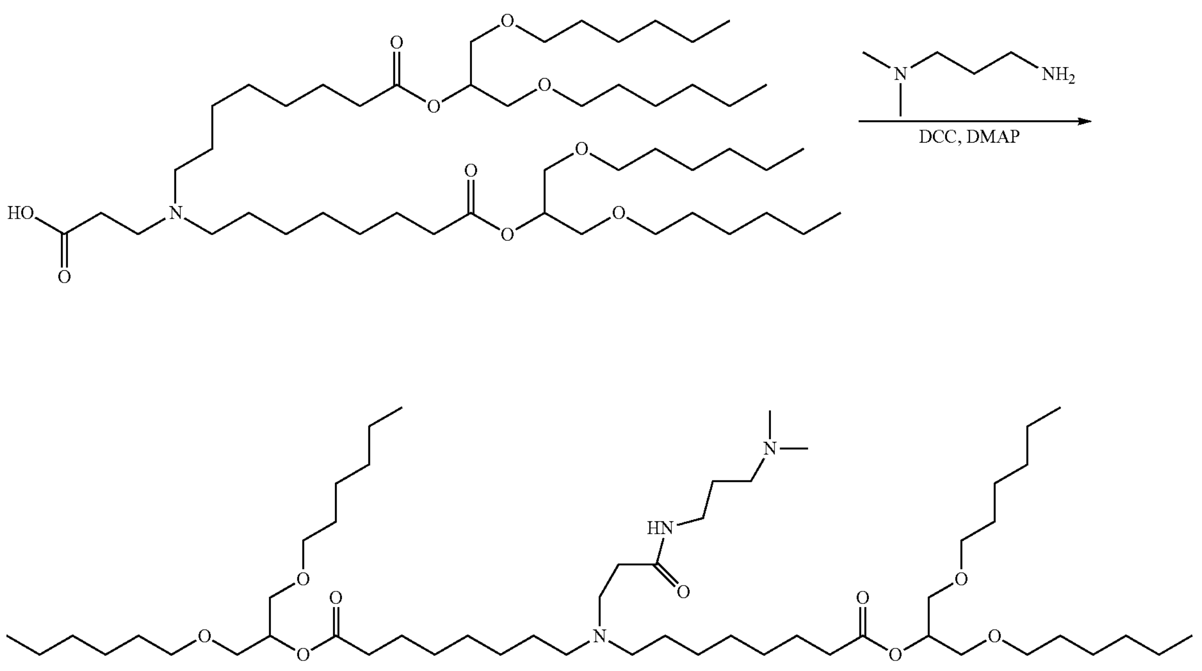

A43 was synthesized employing reaction steps similar to Example 35, 0.5 g product was obtained. $^1$HNMR ($CDCl_3$) δ: ppm. 5.12 (p, 2H), 4.41 (t, 2H), 3.76 (t, 2H), 3.55-3.40 (m, 20H), 3.01-2.76 (m, 10H), 2.49 (t, 2H), 2.32 (t, 4H), 1.59-1.25 (m, 54H), 0.87 (m, 12H); MS(ES): m/z $(M+H)^+$ 942.44.

Example 37—Synthesis of A44

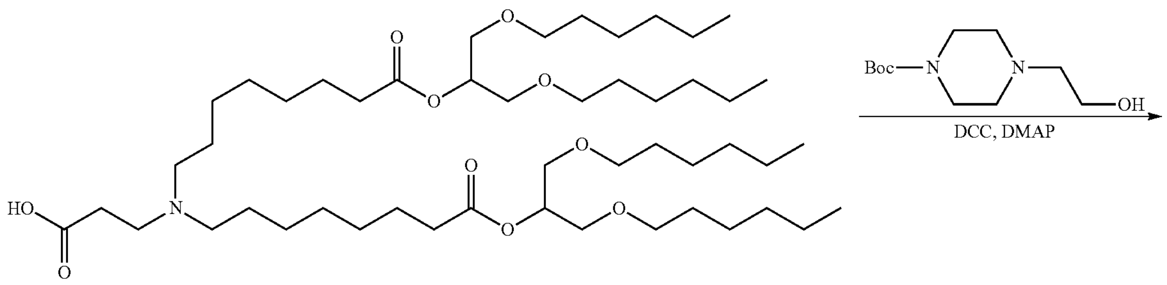

-continued

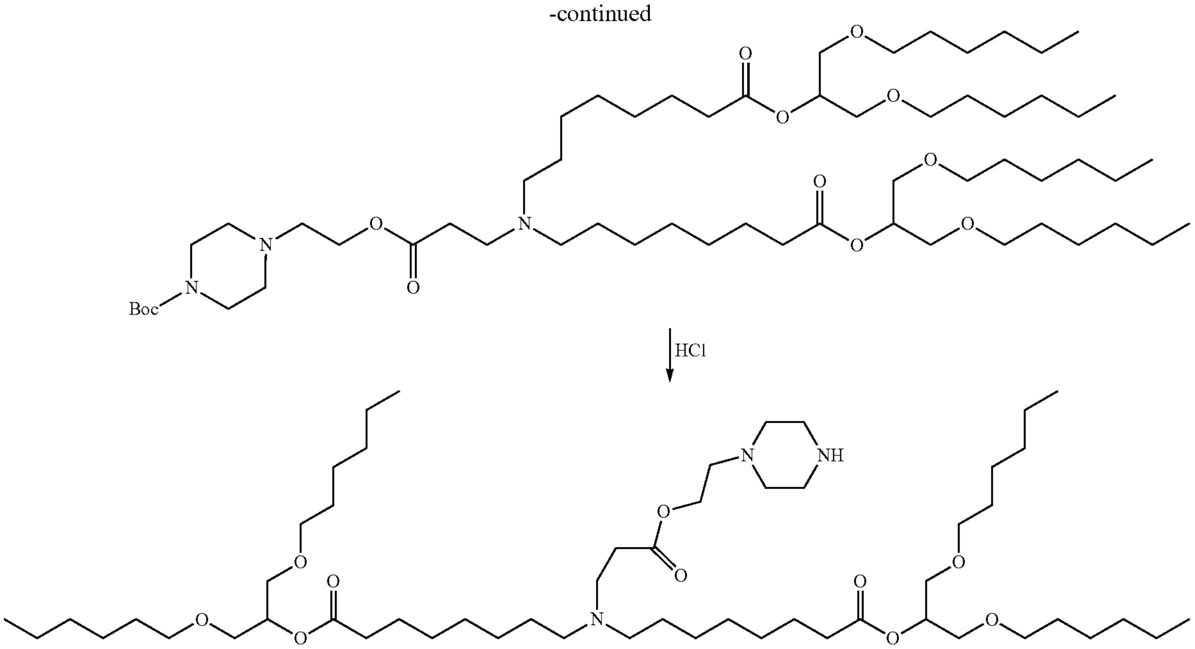

Boc protected piperazine ethanol ester intermediate was synthesized referred to Example 35.

Steps to prepare A44: Boc protected piperazine ethanol ester intermediate (1.1 g) was dissolved in 200 mL 2 mol/L hydrogen ethanol, after the room temperature reaction was completed, it was dried over, concentrated to obtain 0.8 g A44. $^1$HNMR ($CDCl_3$) δ: ppm. 5.10 (p, 2H), 4.35 (t, 2H), 3.60-3.40 (m, 18H), 3.01-2.85 (m, 6H), 2.65-2.50 (t, 10H), 2.32 (t, 4H), 1.59-1.25 (m, 52H), 0.87 (m, 12H); MS(ES): m/z $(M+H)^+$ 970.45.

Example 38—Synthesis of A45

A44 was synthesized employing reaction steps similar to Example 37.

Steps to prepare A45: A44 (1.6 g), sodium carbonate (0.17 g), KI (0.054 g) were dissolved in 50 mL acetonitrile, bromoethanol (0.2 g) was added, after reflux reaction was completed, it was concentrated to remove acetonitrile, stirred and extracted with ethyl acetate and water, the organic layer was dried over, concentrated, and passed through a silica gel column for purification (DCM: MeOH=3%-5%), 1.1 g A45 was obtained. $^1$HNMR ($CDCl_3$) δ: ppm. 5.10 (p, 2H), 4.35 (t, 2H), 3.60-3.40 (m, 18H), 3.32 (t, 2H), 3.01-2.90 (m, 6H), 2.53 (t, 2H), 2.49-2.35 (t, 10H), 2.32 (t, 4H), 1.59-1.25 (m, 52H), 0.87 (m, 12H); MS(ES): m/z $(M+H)^+$ 1014.50.

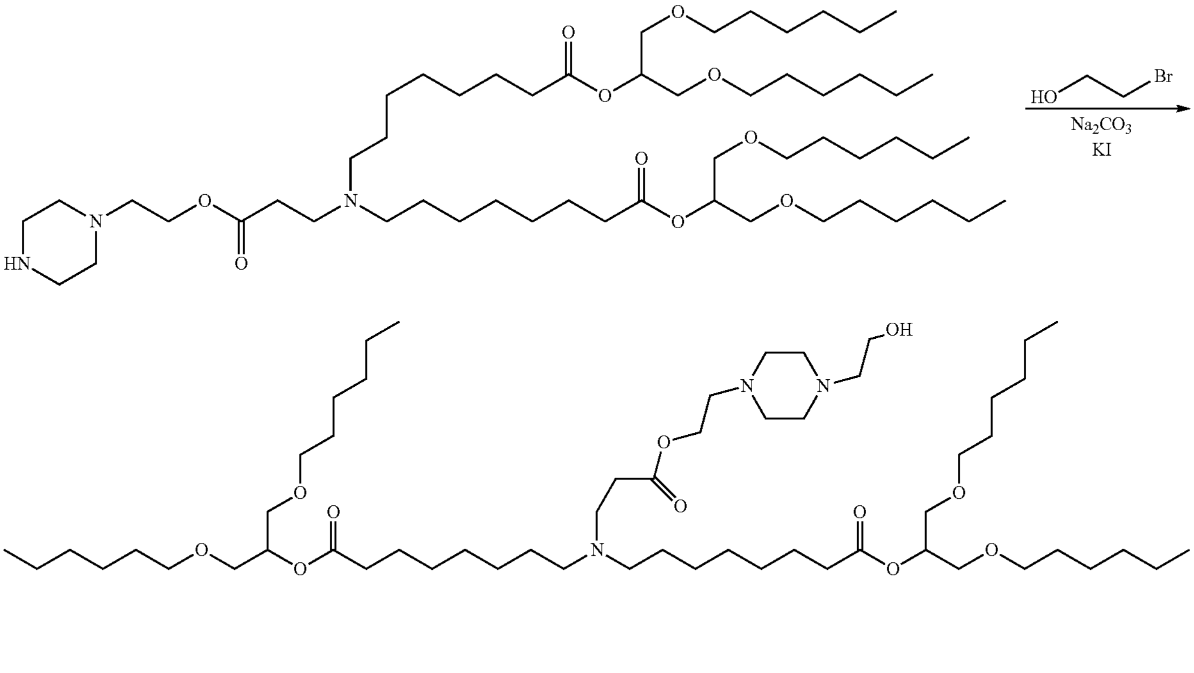

Example 39—Synthesis of A46

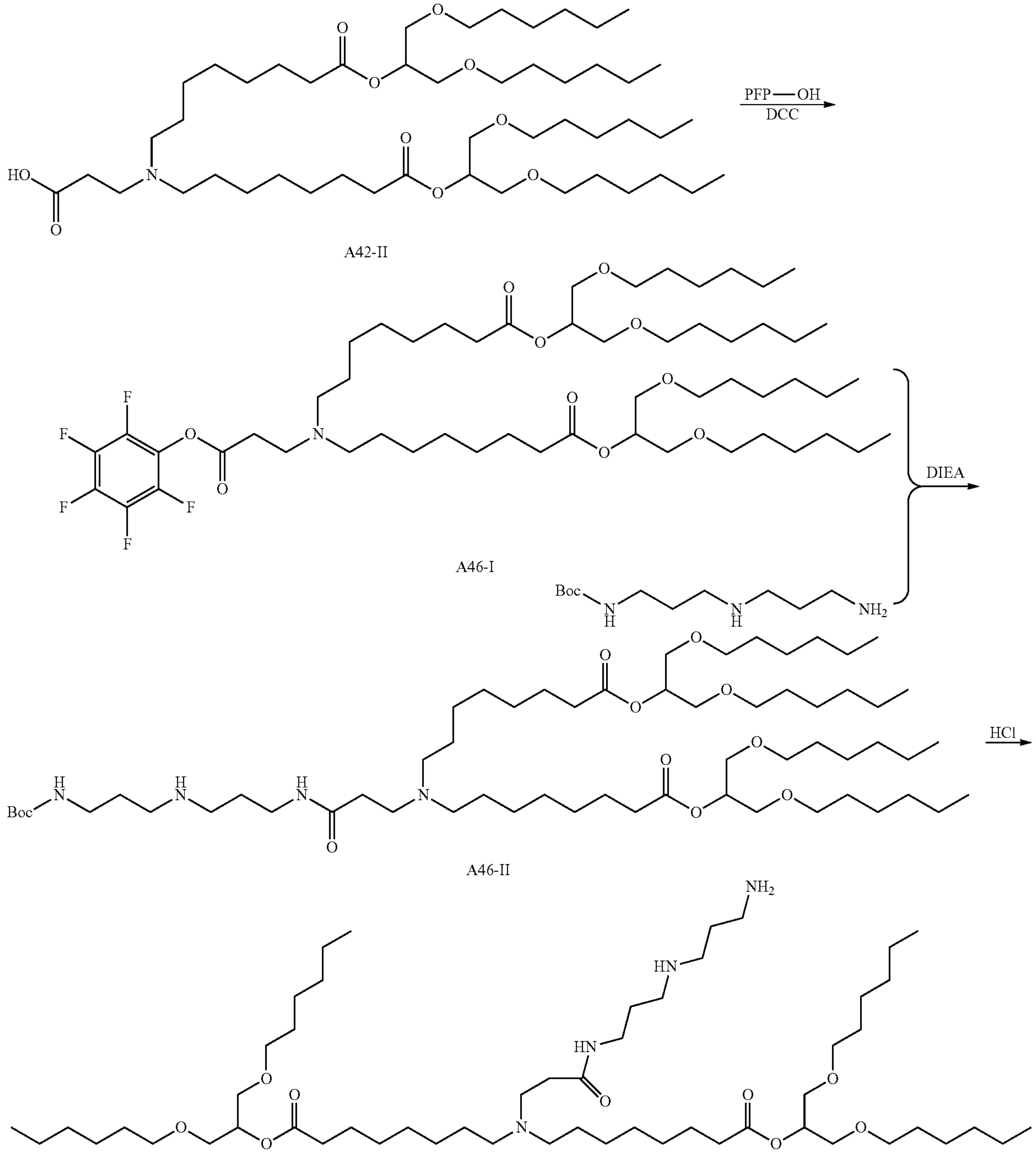

A42-II

A46-I

A46-II

A46

A42-II was synthesized employing reaction steps similar to Example 35.

Steps to prepare A46-I: A42-II (1.5 g), DCC (0.39 g), PFP—OH (0.35 g) were dissolved in 50 mL dichloromethane, after the room temperature reaction was completed, it was concentrated to remove DCM, diluted with ethyl acetate, filtered to remove white undissolved material, stirred and extracted with 10% sodium carbonate solution, the organic layer was dried over, concentrated, and passed through a silica gel column for purification (DCM: MeOH=1%-3%), 1.2 g A46-I was obtained.

Steps to prepare A46-II: mono Boc-diaminodipropylamine (0.23 g), DIEA (0.19 g), A46-I (1 g) were dissolved in 20 mL dichloromethane, after room temperature reaction was completed, dichloromethane and sodium carbonate solution were added to stir and extract, the organic layer was dried over, concentrated, and passed through a silica gel column for purification (DCM:MeOH=1%-3%), 0.8 g A46-II was obtained.

Steps to prepare A46: A46 was synthesized referred to steps to prepare A44 in Example 37. $^{1}$HNMR ($CDCl_3$) δ: ppm. 5.10 (p, 2H), 3.60-3.40 (m, 18H), 3.37 (t, 2H), 2.70-2.55 (m, 10H), 0.2.50 (t, 2H), 2.32 (t, 4H), 1.72 (m, 4H), 1.59-1.25 (m, 52H), 0.87 (m, 12H); MS(ES): m/z $(M+H)^+$ 971.48.

Example 40—Synthesis of A47

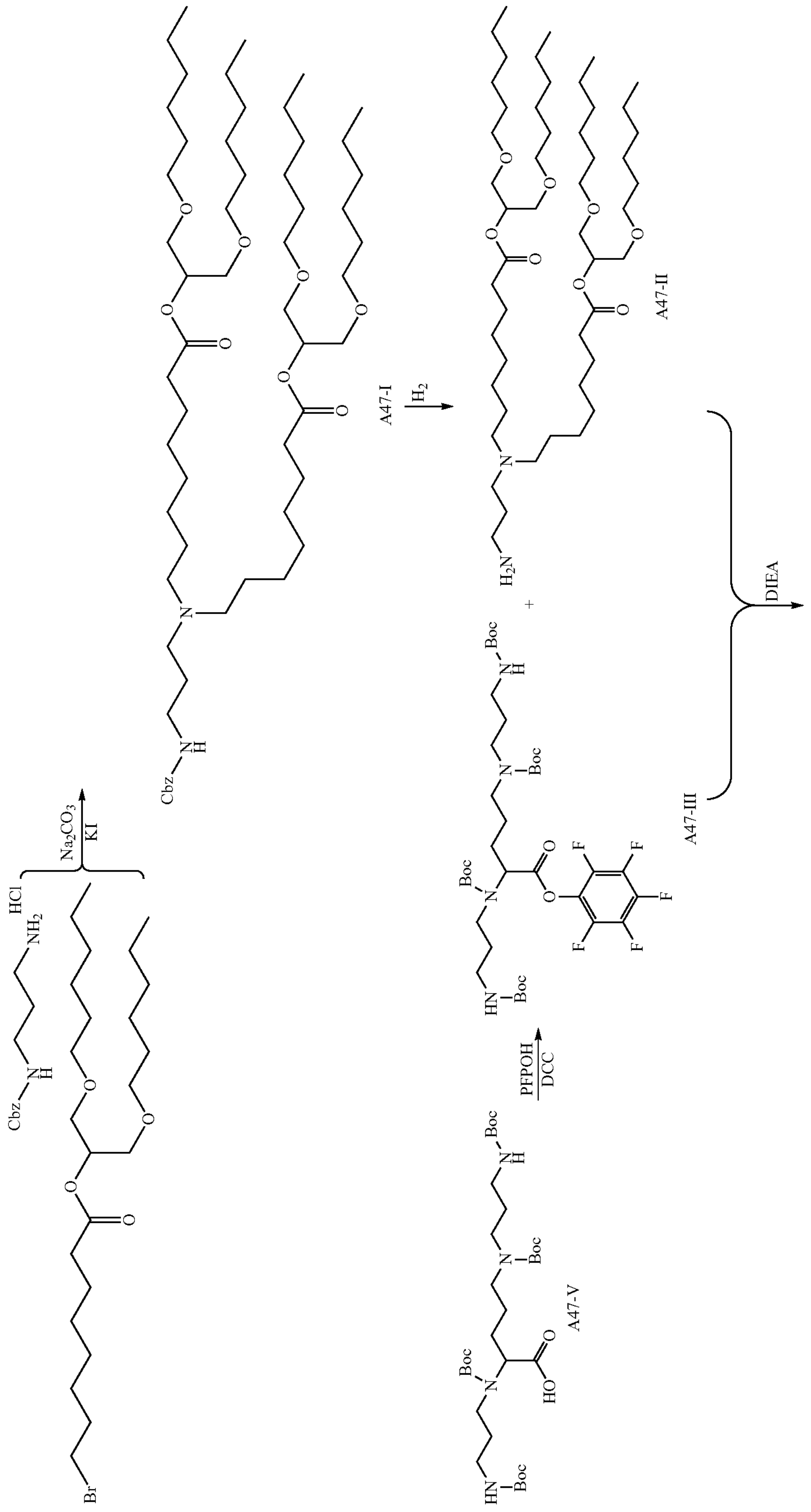
A47-I
A47-II
A47-III
A47-V

-continued
A47-IV
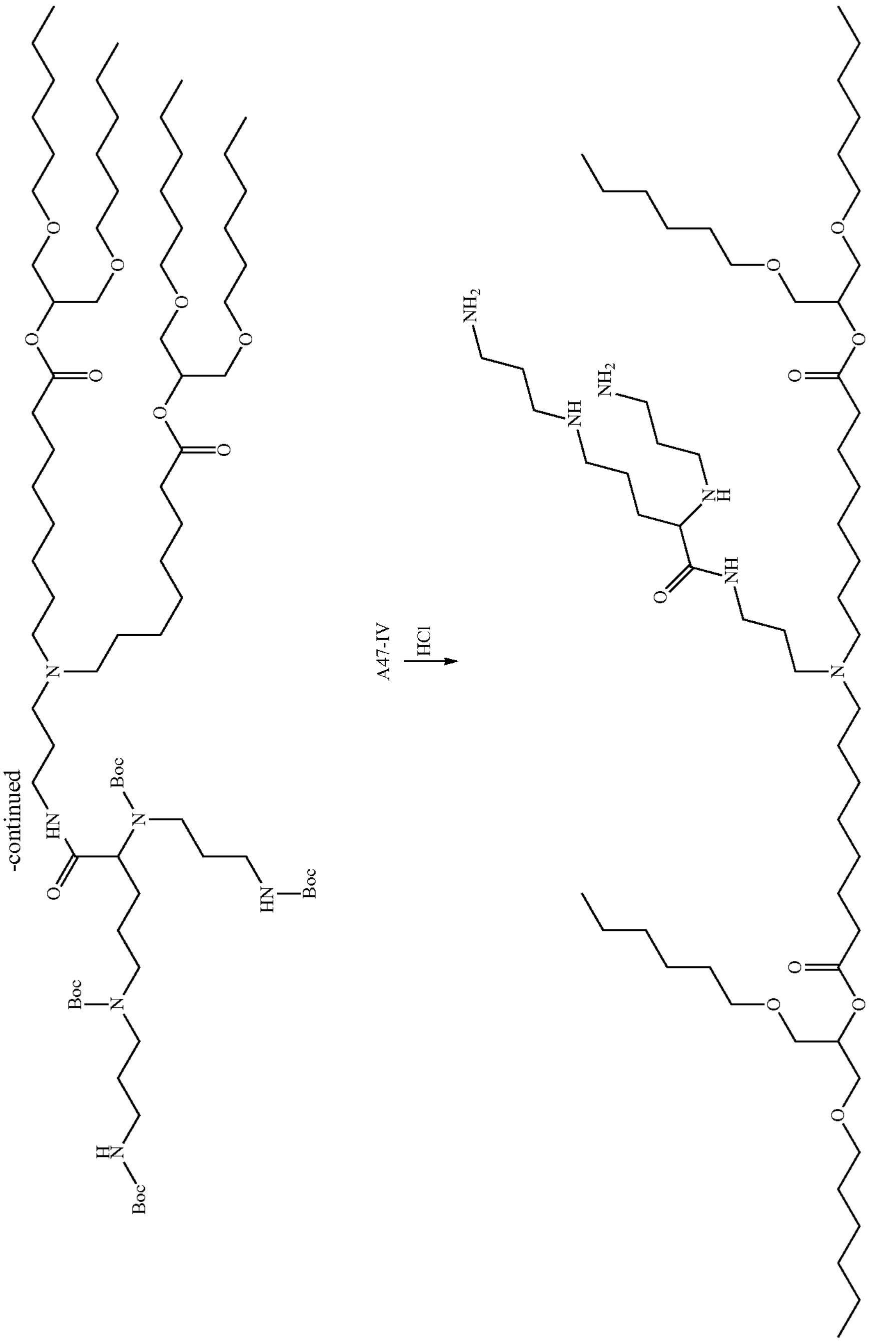
A47

Steps to prepare A47-I: A47-I was synthesized according to steps used to prepare A42-I in Example 35.

Steps to prepare A47-II: A47-II was synthesized according to steps used to prepare A42-II in Example 35.

Steps to prepare A47-III: A47-III was synthesized according to steps used to prepare A46-I in Example 39.

Steps to prepare A47-IV: A47-IV was synthesized according to steps used to prepare A46-II in Example 39.

Steps to prepare A47: 1.1 g A47 was synthesized according to steps used to prepare A44 in Example 37. $^{1}$HNMR (400 MHz, $CD_3OD$) δ: ppm. 5.10 (m, 2H), 3.53 (m, 8H), 3.44 (m, 9H), 3.20-3.0 (m, 16H), 2.34 (t, 4H), 2.09 (m, 4H), 1.98 (dt, 4H), 1.84 (dd, 4H), 1.71 (s, 4H), 1.63 (dd, 4H), 1.53 (m, 8H), 1.40-1.20 (m, 40H), 0.88 (m, 12H); MS(ES): m/z $(M+H)^+$1071.65.

Example 41—Synthesis of A48

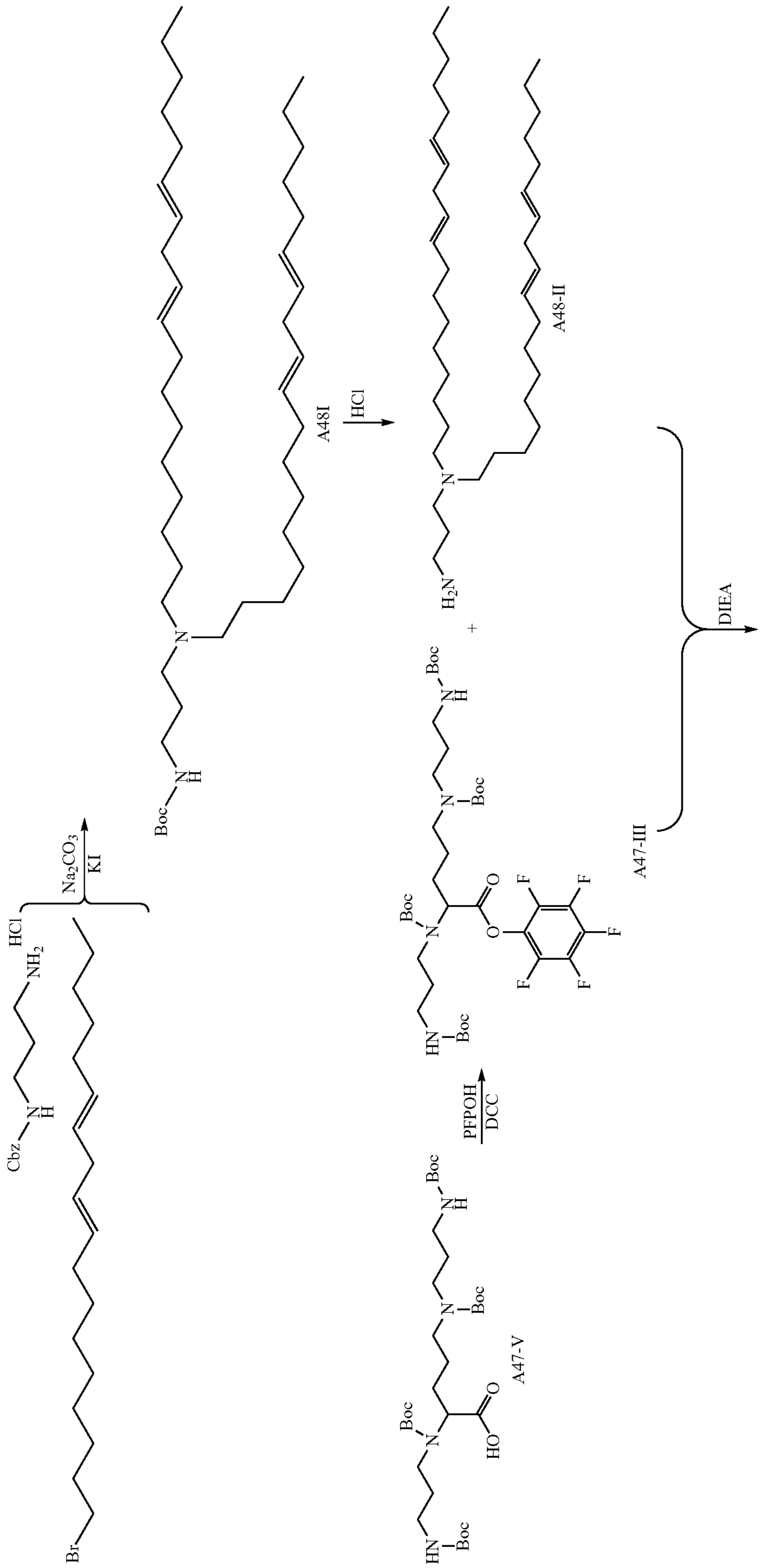
A48I
A48-II
A47-III
A47-V

-continued
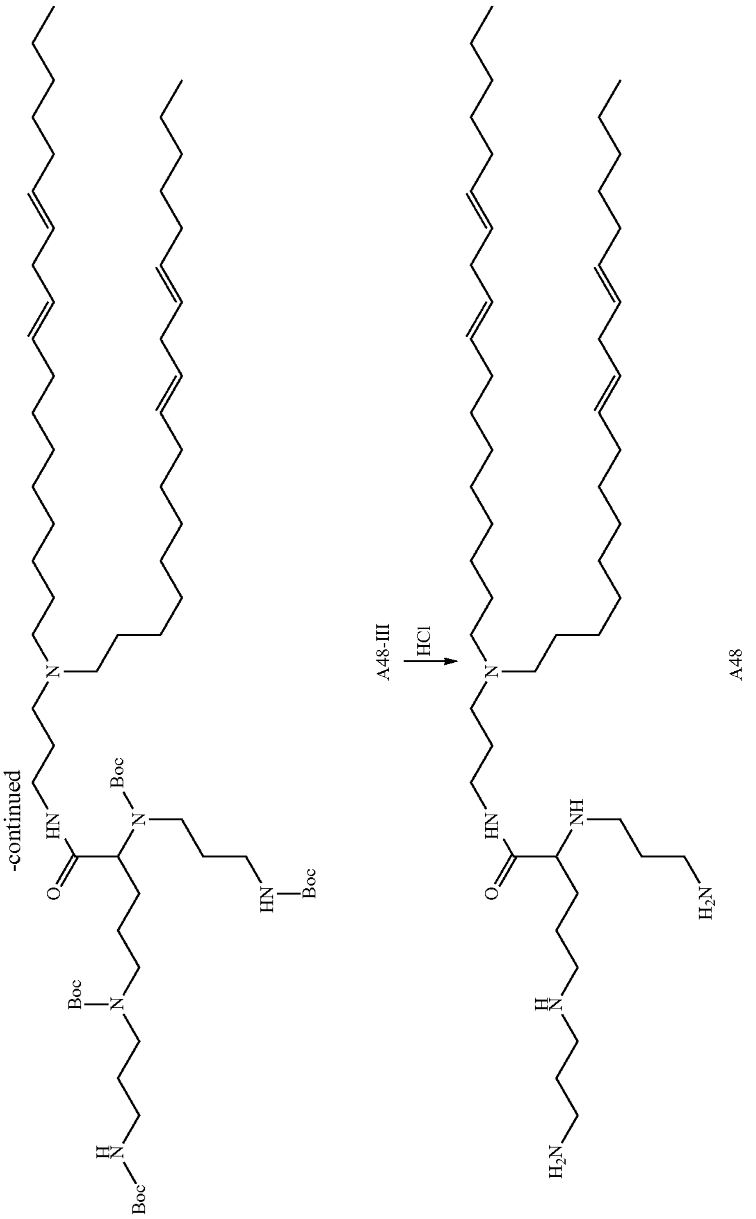
A48-III
A48

Steps to prepare A48-I: A48-I was synthesized according to steps used to prepare A42-I in Example 35.

Steps to prepare A48-II: A48-II was synthesized according to steps used to prepare A42-II in Example 35.

Steps to prepare A48-III: A48-III was synthesized according to steps used to prepare A46-II in Example 39.

Steps to prepare A48: 0.5 g A48 was synthesized according to steps used to prepare A44 in Example 37. $^1$HNMR (400 MHz, $CD_3OD$) δ: ppm. 7.78 (m, 7H), 5.08 (m, 8H), 3.87 (m, 1H), 3.0-2.91 (m, 2H), 2.71 (m, 4H), 2.50 (m, 12H), 1.84 (dd, 4H), 1.71 (m, 4H), 1.63-1.53 (m, 12H), 1.40-1.20 (m, 36H), 0.88 (m, 6H); MS(ES): m/z $(M+H)^+$ 799.35

Comparative Examples—MC3, A2, A3, A4, A8 and A33

MC3, A2, A3, A4, A8 and A33 are used for comparative example. Because MC3, A2, A3, A4, A8 and A33 are known cationic liposomes, their synthesis methods are not described specifically here. MC3, A2, A3, A4, A8 and A33 are shown as follows:

MC3

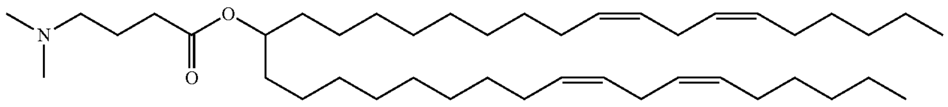

A2

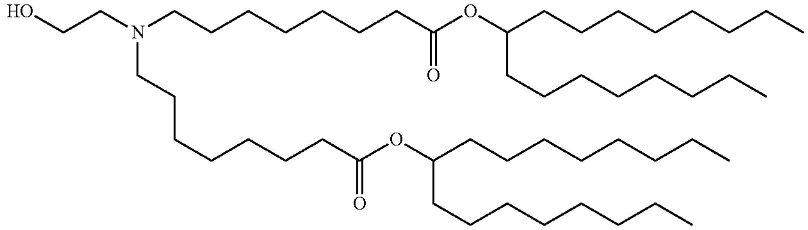

A3

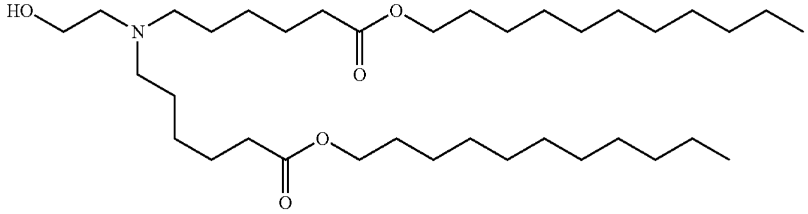

A4

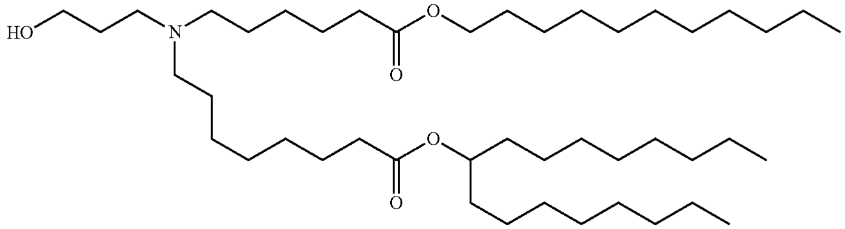

A8

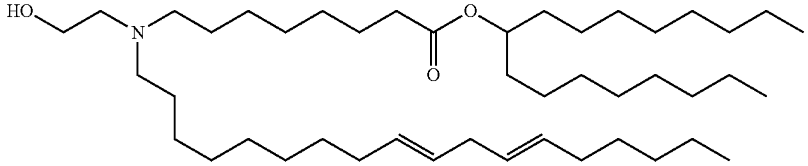

A33

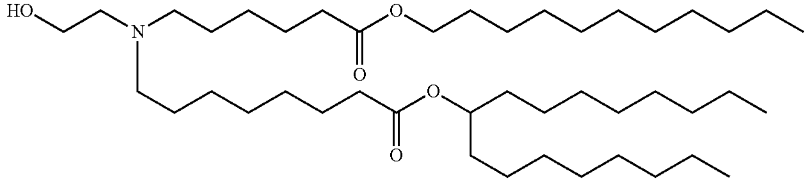

Example 42—Production of Lipid Nanoparticles

Lipid nanoparticles were prepared using the following ingredients: (1) an ionizable lipid compound which were commercially available or synthesized, e.g., MC3 (purchased from Avanti), A1-A33 were synthesized in-house; (2) phospholipid (e.g., DOPE or DSPC, purchased from Avanti); (3) PEG lipid (e.g., PEG-DMG, purchased from Avanti or synthesized in-house); (4) structural lipid (e.g., cholesterol, purchased from Sigma-Aldrich); (5) effective composition/active ingredient (e.g., Luciferase mRNA, siRNA, SARS-CoV-2 S protein mRNA, Cas 9 mRNA, etc.)

Preparation and encapsulation method: (1) ionizable lipid, phospholipid, pegylated lipid and structural lipid were dissolved and mixed in ethanol at 50%, 10%, 1.5%, and 38.5% successively and respectively; (2) a microfluidic chip or T-type mixer were employed to mix lipid mixture and active ingredient (mRNA) evenly at a ratio of 1:3 to obtain lipid nanoparticles.

Encapsulation percentage reflects the encapsulation extent of the encapsulated substance. The higher the encapsulation percentage, the decomposition possibility of the encapsulated substance is less during the delivery in vivo.

TABLE 1

Performance of ionizable lipid and its lipid nanoparticle

| Ionizable lipid | Size (nm) | PDI | Encapsulated percentage (%) |
|---|---|---|---|
| A1 | 127.7 | 0.090 | 88.79 |
| A2 | 145.5 | 0.100 | 87.86 |
| A3 | 140.6 | 0.120 | 81.47 |
| A4 | 131.1 | 0.110 | 79.24 |
| A5 | 135.0 | 0.090 | 90.11 |
| A6 | 171.5 | 0.190 | 87.09 |
| A7 | 105.1 | 0.175 | 94.63 |
| A8 | 142.2 | 0.120 | 76.10 |
| A9 | 129.4 | 0.120 | 93.35 |
| A10 | 121.6 | 0.104 | 82.65 |
| A12 | 119.3 | 0.083 | 86.53 |
| A13 | 96.87 | 0.146 | 95.51 |
| A17 | 109.5 | 0.1037 | 92.99 |
| A18 | 104.8 | 0.0835 | 93.58 |
| A19 | 110.1 | 0.0923 | 88.00 |
| A20 | 77.17 | 0.121 | 97.09 |
| A21 | 78.3 | 0.098 | 97.20 |
| A22 | 86.19 | 0.049 | 96.85 |
| A23 | 74.63 | 0.054 | 97.41 |
| A24 | 78.69 | 0.78 | 96.77 |
| A25 | 105.3 | 0.094 | 83.60 |
| A26 | 120.3 | 0.064 | 83.56 |
| A27 | 94.16 | 0.13 | 96.69 |
| A28 | 91.19 | 0.13 | 89.72 |
| A29 | 126.4 | 0.05 | 89.98 |
| A30 | 110.1 | 0.28 | 98.14 |
| A32 | 128.7 | 0.07 | 94.19 |
| MC3 | 86.7 | 0.10 | 92.00 |

Example 43—Experiments for Proving Transfection Efficiency

Encapsulated the nanoparticle of various cationic lipid compounds and luciferase mRNA according to the method in Example 42, tested the fluorescence intensity or total number of photons of luciferase mRNA encapsulated by different LNP.

Experimental animal: SPF grade BALB/c mice, female, 6-8 week old, body weight ranged 18-22 g, were purchased from Beijing Vital River Laboratory Animal Technology Co. Ltd, with production license no.: SXCK (JING) 2016-0006. All animals were kept in adaptive feeding for more than 7 days before experiments, free to uptake food and drink water during experimental period, illumination 12/12 h alternating light and dark, room temperature was 20-26° C., humidity was 40-70%.

Experimental method: female BALB/c mice, encapsulated luciferase mRNA with different LNP by four different administrations which included subcutaneous injection (under the armpit), tail vein injection, intraperitoneal injection, intramuscular injection (the tibialis anterior muscle of mouse hind leg); 3, 6, 24, 48 h after administration, applied in vivo fluorescence imaging system (brand: Bruker, model: XTREME) for bioluminescence detection, the specific steps were as follows: substrate preparation: took appropriate amount of substrate Luciferin (brand: Promega) and added saline to make a 10 mg/ml solution, avoided light, injected 100 μl solution into each mouse intraperitoneally. Mouse moved freely for 5-10 min after being administrated substrate, then put them into anesthesia box and used 2.5% isoflurane for anesthesia. Put the anesthetized mouse into machine, set the bioluminescence setting and took the photos, captured the photograph and then adjusted the upper and lower values of photograph, then collected data on the concentrated distribution of fluorescence (e.g., fluorescence intensity, average photons number, and total photons number) and processed data. Statistical analysis: the in vivo imaging outcome were shown in the fluorescence intensity or average of total photons number of different animal in the same tested group, which were used to judge whether the fluorescence intensity or total photon number of luciferase mRNA encapsulated by different LNP were high or low.

The fluorescence intensity and total photons number reflects the transfection efficiency of LNP, the value is higher, referring to the efficiency of delivering encapsulated substance into cell by LNP is higher.

TABLE 2

The expression of induced luciferase of A1-A9 ionizable lipid nanoparticle

| | Average fluorescence intensity | | | | | |
|---|---|---|---|---|---|---|
| | 3 h | | 6 h | | 24 h | |
| Cationic lipid | Leg (intramuscular injection) | Liver (tail vein injection) | Leg (intramuscular injection) | Liver (tail vein injection) | Leg (intramuscular injection) | Liver (tail vein injection) |
| A1 | 61.3 | 20.4 | 80.6 | 27.80 | 38.9 | 15.9 |
| A2 | 1146 | 5325.2 | 1208.2 | 5934.7 | 377.7 | 162.6 |

TABLE 2-continued

The expression of induced luciferase of A1-A9 ionizable lipid nanoparticle

| | Average fluorescence intensity | | | | | |
|---|---|---|---|---|---|---|
| | 3 h | | 6 h | | 24 h | |
| Cationic lipid | Leg (intramuscular injection) | Liver (tail vein injection) | Leg (intramuscular injection) | Liver (tail vein injection) | Leg (intramuscular injection) | Liver (tail vein injection) |
| A3 | 60.3 | 12.1 | 69.8 | 11.9 | 35.9 | 13.5 |
| A4 | 1847.5 | 7962.6 | 1956.2 | 7745.9 | 1009.7 | 326.4 |
| A5 | 675.7 | 2231.2 | 1566.4 | 3738.2 | 892.2 | 73.5 |
| A6 | 60.3 | 11.9 | 40.9 | 9.0 | 19.1 | 12.2 |
| A7 | 1683.2 | 21013.1 | 2990.1 | 21315.5 | 1436.4 | 444.2 |
| A8 | 1111 | 6850.3 | 2161.8 | 10174.4 | 1294.9 | 220.8 |
| A9 | 461.4 | 198.9 | 432.0 | 252.7 | 178.3 | 14.6 |
| A33 | 1065.5 | 2841.8 | 1117.9 | 3144.6 | 418.8 | 100.0 |

Note:
administration route: (1) intramuscular injection; (2) tail vein injection; dose: 10 μg/mice; detection time: 3, 6, and 24 h after administration.

TABLE 3

The expression of induced luciferase of A18-A33 ionizable lipid nanoparticle

| | Total photons number | | |
|---|---|---|---|
| Cationic lipid | 3 h Leg | 6 h Leg | 24 h Leg |
| A10 | NA | 3.17E+09 | NA |
| A11 | NA | 1.33E+09 | NA |
| A12 | NA | 6.91E+08 | NA |
| A13 | NA | 3.66E+09 | NA |
| A15 | NA | 8.78E+08 | NA |
| A18 | 3.91E+09 | 4.16E+09 | 2.90E+08 |
| A19 | 3.69E+09 | 4.77E+09 | 7.33E+08 |
| A27 | 1.34E+09 | 1.04E+09 | 3.41E+08 |
| A28 | 6.50E+08 | 4.26E+08 | 1.83E+08 |
| A31 | 1.58E+08 | 2.65E+08 | 8.43E+07 |
| A33 | 1.41E+08 | 2.35E+08 | 5.84E+07 |
| MC3 | 3.43E+08 | 7.41E+08 | 2.86E+08 |

Note:
administration route: intramuscular injection; dose: 1 μg/ mice; detection time: 3, 6, and 24 h after administration.

TABLE 4

The expression of induced luciferase of A20-A25, A33 ionizable lipid nanoparticle

| | Total photons number | | |
|---|---|---|---|
| Cationic lipid | 3h Leg | 6h Leg | 24 h Leg |
| A20 | 5.99E+08 | 5.65E+08 | 2.03E+08 |
| A21 | 9.07E+08 | 7.11E+08 | 1.62E+08 |
| A22 | 4.16E+09 | 5.74E+09 | 1.24E+09 |
| A23 | 4.39E+09 | 2.68E+09 | 8.00E+08 |
| A24 | 1.94E+08 | 1.56E+08 | 6.31E+07 |
| A25 | 4.23E+08 | 2.49E+08 | 9.50E+07 |
| A33 | 5.20E+08 | 4.62E+08 | 1.63E+08 |

Note:
administration route: intramuscular injection; dose: 5 μg/mice; detection time: 3, 6, and 24 h after administration.

Example 44—Evaluate the Safety of LNP

Wistar rats including 4 males and 4 females, with a weight difference of no more than 10%, were selected and randomly divided into two groups: solvent control group and tested substance group. Alb was used in the tested substance group, and the LNP preparation's encapsulation condition and size were shown in table 5. The concentration used in the measurement was 2 mg/mL. Each animal was administered 3 times a day with the volume of each injection as 250 μl. The administration interval was 4 hours. Alternate administration to the left and right legs were performed. The total dosage level was 1.50 mg per rat, which was equivalent to 1200 times the maximum unit weight dosage level for human (assuming the maximum dosage level for human is 0.25 mg). Clinical observation was recorded as follows. Within 24 hours after administration, clinical observation was carried out every hour. Within 24-72 hours after administration, clinical observation was carried out once every 6 hours. Within 4-14 days after administration, clinical observation was carried out once a day. The symptoms of toxicity, the time when the symptoms appeared and disappeared, and the time of death (if occurred) were recorded. Body weight was recorded once a day after administration, and food intake was recorded every 2 days after administration. 14 days after the administration, all the remaining animals were weighed, then euthanized, and major organs were obtained by anatomy. Heart, liver, spleen, lung, kidney, thymus, lymph node, were weighted and relative organ weight (the organ weight/the subject weight×100%; also known as organ coefficient) was calculated. After anatomy, the heart, liver, spleen, lung, kidney, intestine, thymus, lymph node, muscle tissue at the injection site and other organs with pathological changes observed were stored in a fixation solution, and the pathology of each organ was examined by H&E staining. Lesion severity scores were given according to the table below.

TABLE 5

The LNP preparation's encapsulation condition and size

| | Ionizable lipid | Size (nm) | PDI |
|---|---|---|---|
| Solvent control group | — | — | — |
| Tested substance group (LNP empty vector control group) | A18 | 147 | 0.088 |

Figure 2:
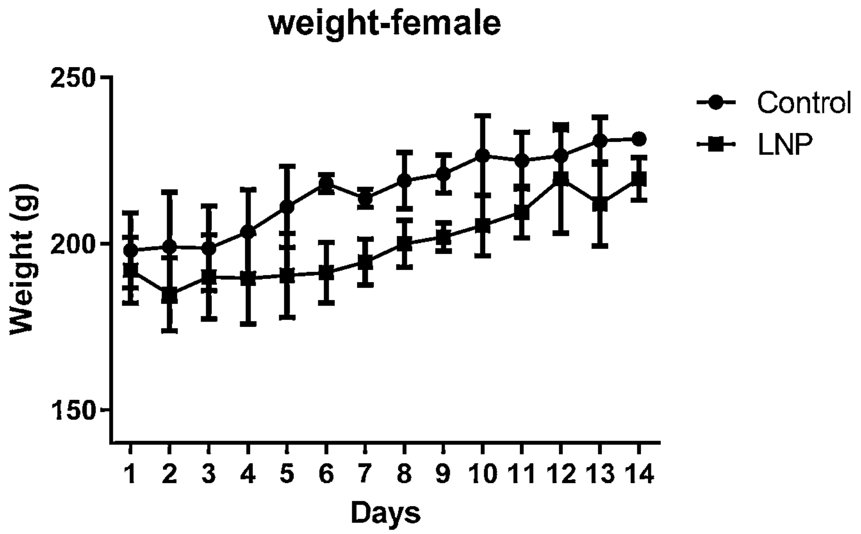
FIG. 2 depicts the weight change of female rat in LNP safety evaluation.
Figure 3:
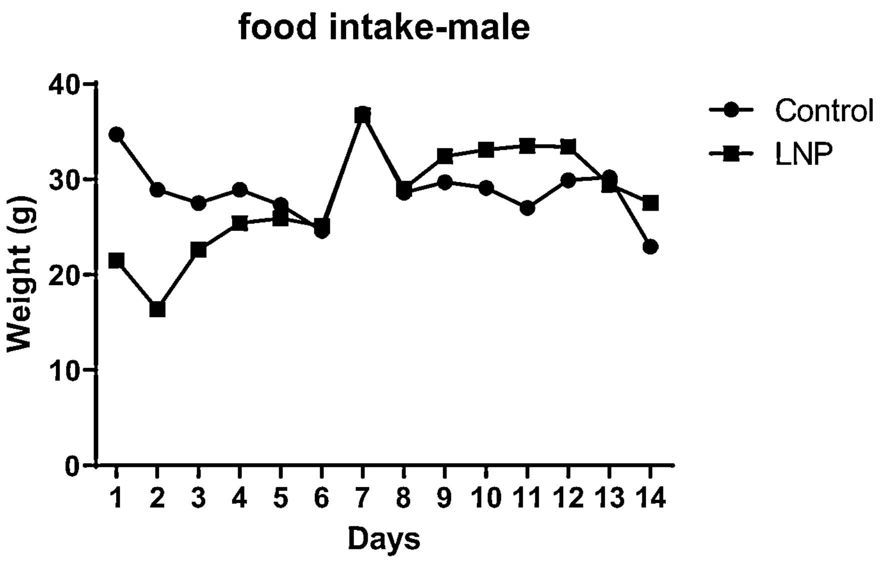
FIG. 3 depicts the food uptake change of male rat in LNP safety evaluation.
Figure 4:
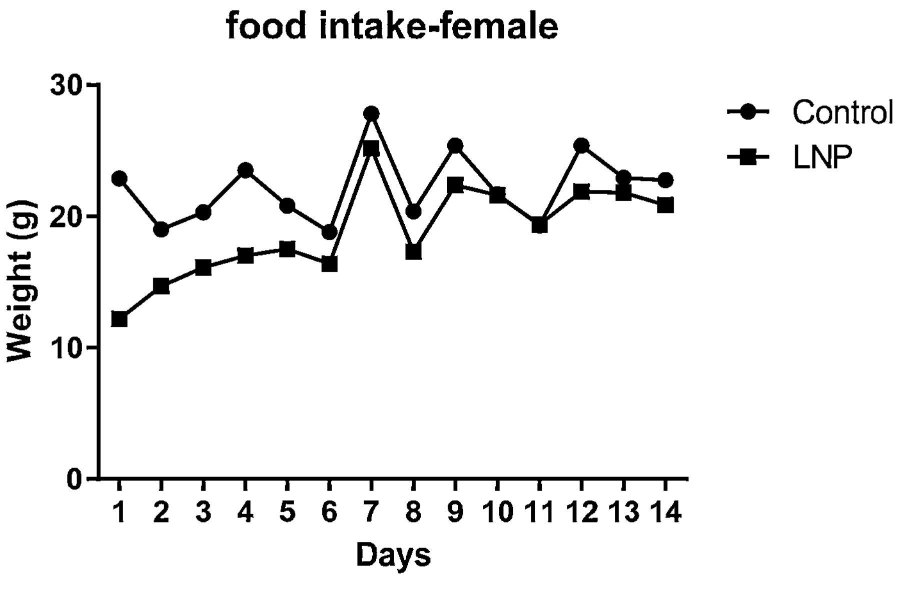
FIG. 4 depicts the food uptake change of female rat in LNP safety evaluation.

The weight change results are shown in FIGS. 1-2. Specifically, the body weight of male rats in the solvent control group continued to increase. The body weight of rats in the tested substance group dropped initially, then recovered to the pre-administration level on Day 4-Day 6, and continued to increase subsequently. The results of changes in food intake are shown in FIGS. 3-4. The food intake per rat in the solvent control group within 24 hours was stable, within a range of 18-35 grams. The initial food intake of the rats in the tested substance group decreased initially, and returned to normal levels on Day 4-Day 7. The relative organ weight results are shown in Table 6. Compared with the solvent control group, the heart, liver, kidney, spleen, thymus and lymph node coefficients of rats in the tested substance group did not show significant difference. The results of histological changes are shown in Table 8. Compared with the rats in the solvent control group (one male and one female), the heart, liver, kidney, spleen, thymus, and lymph nodes of the rats in the tested substance group had no pathological changes. For the tested substance group, there were no other abnormal pathological changes except for the proliferation of partial interstitial cells in the lung and a small amount of inflammatory cell infiltration in the muscle tissue. Based on the above results, the rats showed only slight pathological changes in the lungs and legs after the 1200 times higher dosage level of the LNP injection.

TABLE 6

Acute toxicity test of LNP in rat (relative organ weight)

| | | Heart | Liver | Spleen | Lung | Kidney left | Kidney right | Thymus | Lymph nodes | Brain |
|---|---|---|---|---|---|---|---|---|---|---|
| Solvent control group | Total | 0.302 ± 0.004 | 4.188 ± 0.144 | 0.257 ± 0.045 | 0.376 ± 0.029 | 0.373 ± 0.010 | 0.391 ± 0.006 | 0.186 ± 0.038 | 0.005 ± 0.001 | 0.700 ± 0.127 |
| Tested substance group | Total | 0.308 ± 0.013 | 3.773 ± 0.212 | 0.250 ± 0.029 | 0.413 ± 0.048 | 0.351 ± 0.015 | 0.356 ± 0.025 | 0.149 ± 0.024 | 0.006 ± 0.006 | 0.687 ± 0.142 |

Total: average relative organ weight of male, female rat.

TABLE 7

Lesion severity score standard

| | |
|---|---|
| Score = 0 (does not exist) | Under the conditions of the experiment, taking into account the age, sex and strain of the animal, it can be considered that the tissue is within the normal range and there is no pathological change. |
| Score = 1 (minimal) | The first (lowest) grade of lesions in the 5 grades of minimal, mild, moderate, severe and serious. |
| Score = 2 (mild) | The second grade of lesion degree in the 5 grades of minimal, mild, moderate, severe and serious. |
| Score = 3 (moderate) | The third grade of lesion degree in the 5 grades of minimal, mild, moderate, severe and serious. |
| Score = 4 (severe) | The fourth grade of lesion degree in the 5 grades of minimal, mild, moderate, severe and serious. |
| Score = 5 (serious) | The fifth (highest) grade of lesion degree in the 5 grades of minimal, mild, moderate, severe and serious. |

TABLE 8

Histopathological results of acute toxicity test of LNP in rats

| Group | Animal number | Heart | Liver | Kidney | Spleen | Thymus | Lymph nodes | Pancreas | Lung | Muscle tissue |
|---|---|---|---|---|---|---|---|---|---|---|
| Solvent control group | 5001 | — | — | — | — | — | — | — | — | — |
| | Score | 0 | 0 | 0 | 0 | 0 | 0 | 0 | 0 | 0 |
| | 5101 | — | — | — | — | — | — | — | — | — |
| | Score | 0 | 0 | 0 | 0 | 0 | 0 | 0 | 0 | 0 |
| Tested substance group | 1001 | — | — | — | — | — | — | — | Partial stromal cell hyperplasia | — |
| | Score | 0 | 0 | 0 | 0 | 0 | 0 | 0 | 1 | 0 |
| | 1101 | — | — | — | — | — | — | — | Partial stromal cell hyperplasia | — |
| | Score | 0 | 0 | 0 | 0 | 0 | 0 | 0 | 1 | 0 |

Note:

"—" means no abnormality.

Example 45—Immunity Study of mRNA Encapsulated by LNP

SARS-CoV-2 S protein mRNA was produced by T7 in vitro transcription method, used ionizable lipid A7, A18 and A33 encapsulated lipid nanoparticle according to synthesis method in Example 42, and their encapsulation condition, encapsulated percentage and size were shown in Table 9.

TABLE 9

| Encapsulated outcome | | | |
|---|---|---|---|
| Ionizable lipid | Encapsulated percentage (%) | Size (nm) | PI |
| A33 | 95 | 76 | 0.104 |
| A7 | 97 | 79 | 0.060 |
| A18 | 94 | 86 | 0.075 |

Immunization Program:

| Ionizable lipid | Group | Dose | Species | Administration | Numbers of animal | Animal number |
|---|---|---|---|---|---|---|
| A33 | 1 | 4 μg | BALB/c | intramuscular | 9 | 8001-8009 |
| | 2 | 50 μg | BALB/c | intramuscular | 9 | 9001-9009 |
| A7 | 1 | 4 μg | BALB/c | intramuscular | 9 | 16001-16009 |
| | 2 | 50 μg | BALB/c | intramuscular | 9 | 17001-17009 |
| A18 | 1 | 5 μg | BALB/c | intramuscular | 9 | 3001-3009 |
| | 2 | 20 μg | BALB/c | intramuscular | 9 | 4001-4009 |

Figure 5:
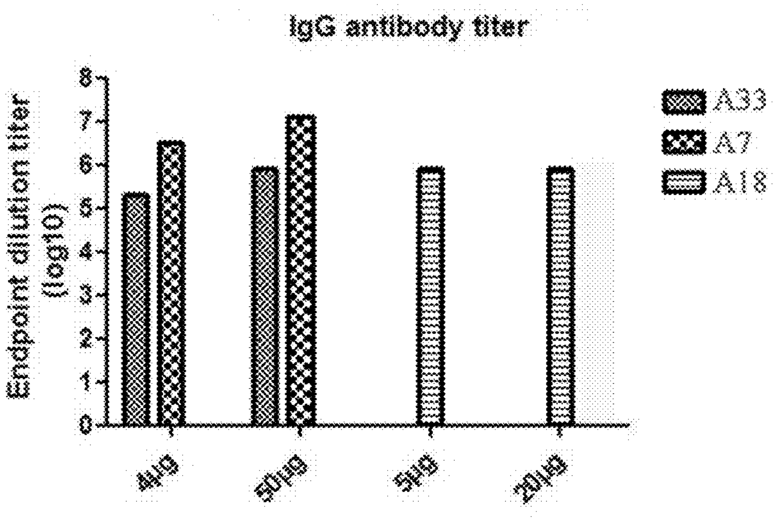
FIG. 5 depicts the IgG antibody titer of LNP-mRNA in an immunogenicity study.

The 3 obtained LNP preparations were used in BALB/c mouse immunization test. The experiment was performed as follows. 6-8 week old female BALB/c mice (9 mice in each group) were administered twice with the LNP preparations on Day 0 and Day 14 by intramuscular injection. The injection volume was 50 μL. After 7 days, the mouse spleens were isolated to separate splenic lymphocytes. The T lymphocytes secreting INFγ were detected by the ELISPOT (Enzyme-linked immune absorbent spot) method and the outcome was shown in table 10, illustrating that mRNA induced stronger cellular immune response in BALB/c mice. 14 days after the second immunization, the S protein specific IgG antibody was detected by indirect ELISA. The IgG antibody EC50 was calculated by fitting the antibody titer curves, as shown in the FIG. 5. The results showed that A7, A18 and A33 were all induced higher titers of IgG antibodies in BALB/c mice Specific operation of ELISPOT was carried according to Mouse IFN-γ precoated ELISPOT kit instruction.

TABLE 10

| Elispot counted T lymphocytes secreting INFγ after administrating different LNP preparations | | | | | | |
|---|---|---|---|---|---|---|
| | A33 | | A7 | | A18 | |
| | 4 μg | 50 μg | 4 μg | 50 μg | 5 μg | 20 μg |
| Blank control | 0 | 2 | 12 | 29 | 1 | 0 |
| S protein (1 μg) | 32 | 310 | 294 | 805 | 161 | 241 |
| | 42 | 338 | 811 | 700 | 153 | 251 |
| Positive control | 679 | 868 | 124 | N/A | 344 | 474 |

Specific operation of indirect ELISA to detect S protein specific IgG antibody titer:

1. coated antigen: S protein was diluted to 2 ng/uL with coating buffer, 100 uL/well, coated overnight at 4° C.;
2. washed plate 3 times with 1×PBST, washed 5 min each time;
3. blocked with 1% BSA blocking solution, 200 uL/well, and left to stand 1 h at 37° C.;
4. washed plate 3 times with 1×PBST, washed 5 min each time;
5. serum to be tested was diluted with dilution buffer by doubling dilution, 100 uL/well, incubated for 1 h at 37° C., and set negative serum control group and blank control group without serum;
6. washed plate 3 times with 1×PBST, washed 5 min each time;
7. anti IgG secondary antibody was diluted by 1:1000, 100 uL/well, incubated for 1 h at 37° C.;
8. washed plate 3 times with 1×PBST, washed 5 min each time;
9. added fresh TMB chromogen solution, 100 uL/well, incubated for an appropriate time at 37° C.;
10. added 2 mol/L termination solution of sulfuric acid, 50 uL/well.
11. used enzyme-labeled instrument to measure OD450 nm absorbance.

ELISA to Detect Antibody

First Immune 14 Days Antibody Detection 1. sample: first immuned 14 days mouse serum of immune group, solvent control group, mixed 6 mouse's serum in each group
2. antigen protein: SARS-CoV-2 (COVID-19) S protein (R683A, R685A), His Tag (SPN-052H4)
3. coated antigen protein: 2 ng/μL, 100 uL/well
4. second immune: Goat anti-mouse IgG (H+L), HRP conjugate 1:1000 dilution Second Immune 14 Days Antibody Detection 1. sample: second immuned 14 days mouse serum of immune group, solvent control group, mixed 6 mouse's serum in each group
2. antigen protein: SARS-CoV-2 (COVID-19) S protein (R683A, R685A), His Tag (SPN-052H4)
3. coated antigen protein: 2 ng/μL, 100 uL/well
4. second immune: Goat anti-mouse IgG (H+L), HRP conjugate 1:1000 dilution
5. outcome shown in FIG. 5.

What is claimed:

1. A compound of formula (II):

(II)

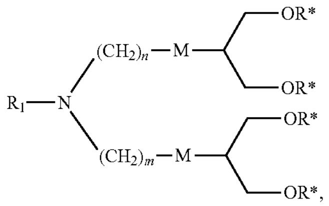

wherein $R_1$ is selected from —$R_{1'}$—X, $R_1$' is —$(CH_2)_{1-6}$—,

X is amino, hydroxyl, ethynyl, cyano, —C(O)$(CH_2)_{1-3}NR_aR_b$, —C(O)O$(CH_2)_{1-3}NR_aR_b$, —OC(O)$(CH_2)_{1-3}NR_aR_b$, —C(O)NH$(CH_2)_{1-3}NR_aR_b$, —NHC(O)$(CH_2)_{1-3}NR_aR_b$, —NHC(O)CH$(NR_aR_b)(CH_2)_{1-3}NR_aR_b$, $C_{3-7}$ cycloalkyl, 4-7 membered heterocyclic group, $C_{6-10}$ aryl or 5-10 membered heteroaryl, the said cycloalkyl, heterocyclic group, aryl or heteroaryl are optionally substituted by the following groups: —$(CH_2)_{1-3}$OH, —$(CH_2)_{1-3}NR_aR_b$, and —$(CH_2)_{1-3}$C(O) $NR_aR_b$; or X can also be:

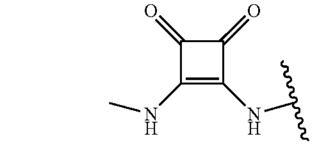

or

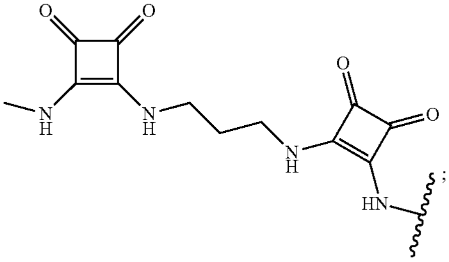

;

$R_a$, and $R_b$ are independently selected from H, $C_{1-3}$ alkyl, —$(CH_2)_{1-3}NH_2$, and —$(CH_2)_{1-3}NH(CH_2)_{1-3}NH_2$; or $R_a$, and $R_b$ together with the nitrogen to which they are attached form a 5-10 membered heterocycle including 1-3 heteroatoms selected from N, O or S, by said heterocycle is optionally substituted by one or more of the following groups: $C_{1-6}$ alkyl, $C_{1-6}$ alkyl halides, $C_{1-6}$ alkyl hydroxyl and $C_{1-6}$ alkyl amino;

each R* is independently selected from $C_{2-10}$ alkyl;

each M is independently selected from —$CH_2$—, —CH═CH—, —NH—, —C(O)—, —O—, —C(O)O—, —OC(O)—, —C(O)NH—, and —NHC(O)—;

n, m are independently selected from the integer range from 1-9;

or a salt or an isomer thereof.

2. The compound of claim 1, wherein:

$R_1$' is —$(CH_2)_{2-3}$—, X is hydroxyl, —C(O)$(CH_2)_{2-3}NR_aR_b$, —C(O)O$(CH_2)_{2-3}NR_aR_b$, —C(O)NH$(CH_2)_{2-3}NR_aR_b$, or 5-10 heteroaryl which is optionally substituted by the following groups: —$(CH_2)_{2-3}$OH, —$(CH_2)_{2-3}NR_aR_b$, —$(CH_2)_{2-3}$C(O) $NR_aR_b$; or X can also be:

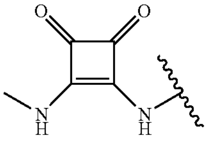

or

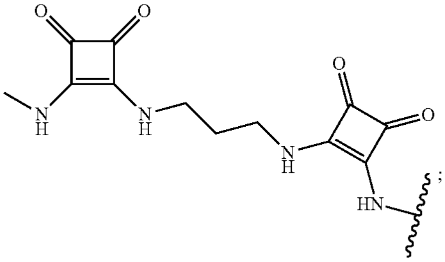

;

$R_a$, and $R_b$ are independently selected from H, $C_{1-3}$ alkyl, —$(CH_2)_{2-3}NH_2$, or —$(CH_2)_{2-3}NH(CH_2)_{2-3}NH_2$; or $R_a$, and $R_b$ together with the nitrogen to which they are attached form a 5-10 membered heterocycle including 1-3 heteroatoms selected from N or O, said heterocycle is optionally substituted by the following groups: $C_{1-6}$ alkyl, $C_{1-6}$ alkyl halides, $C_{1-6}$ alkyl hydroxyl groups and $C_{1-6}$ alkyl amino groups;

or a salt thereof.

3. The compound of claim 1, wherein:

each M is independently selected from —$CH_2$—, —CH═CH—, —C(O)O—, —OC(O)—, —C(O)NH—, —NHC(O)—;

or a salt thereof.

4. The compound of claim 1, wherein:

each n is 7, and m is 7;

or a salt thereof.

5. A compound or salts or isomers thereof, wherein:

the compound is one of

A1

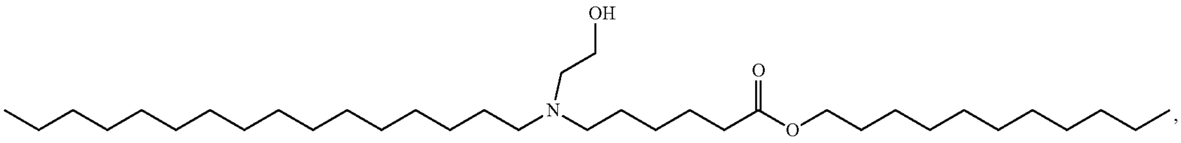

,

A6

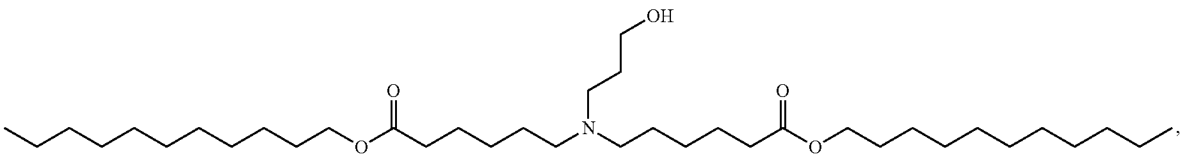

,

-continued
A9
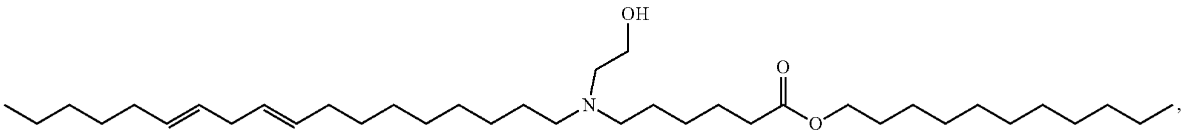
A10
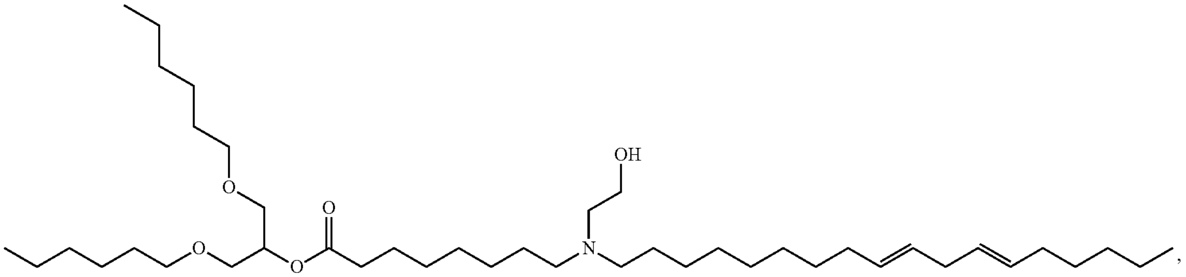
A11
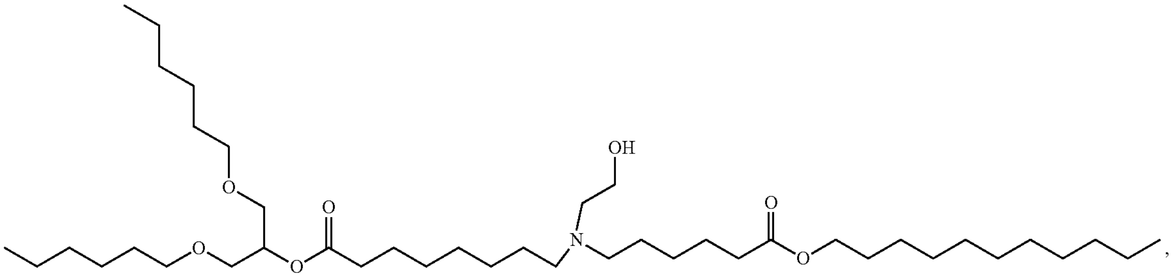
A12
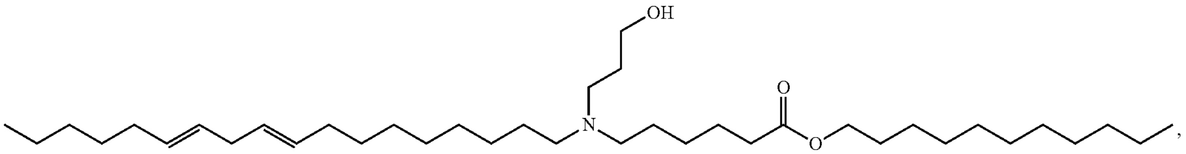
A13
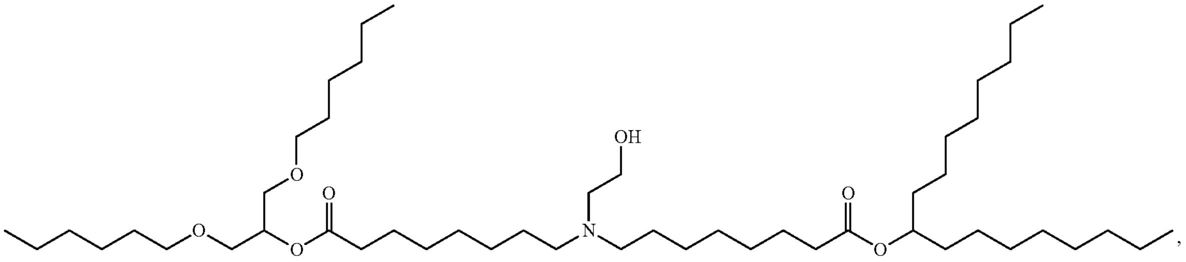
A15
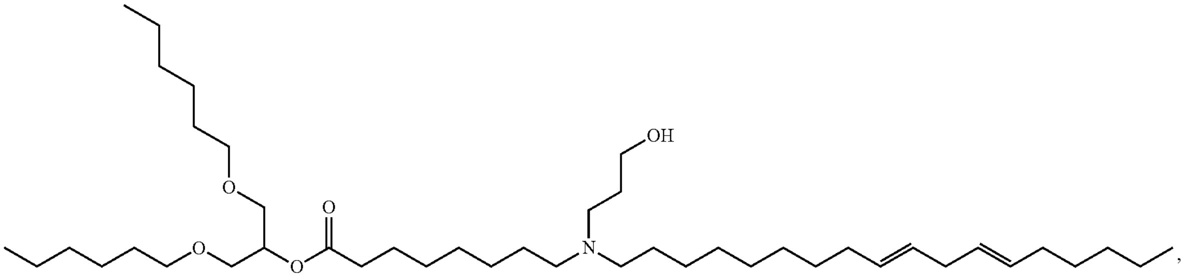

-continued
A16
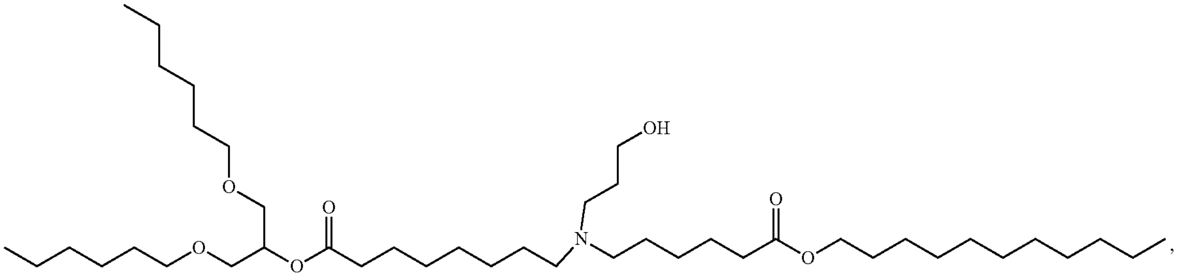
,
A17
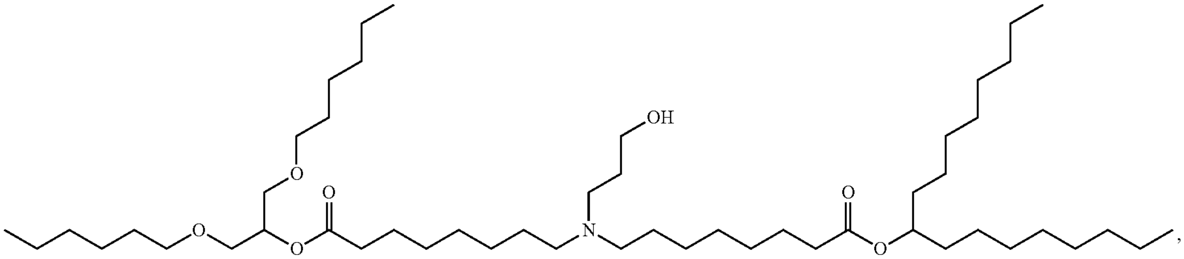
,
A18
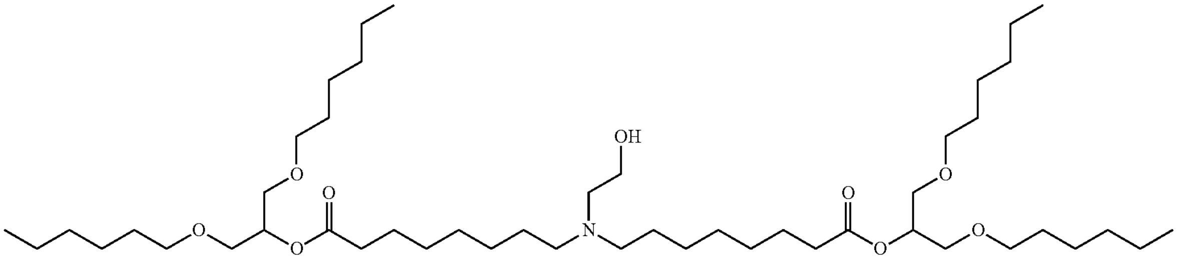
,
A19
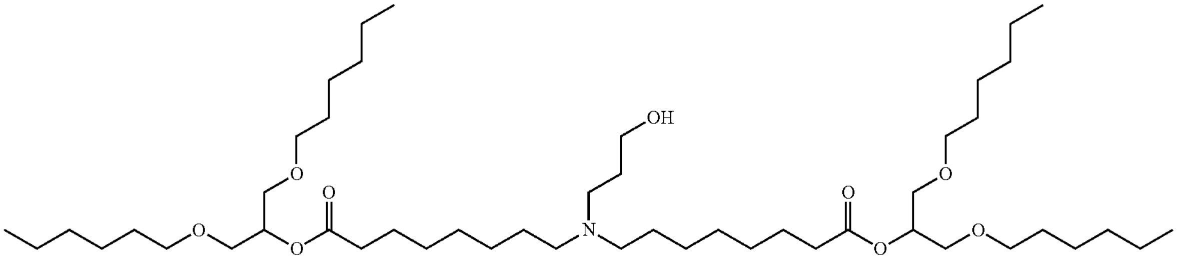
,
A20
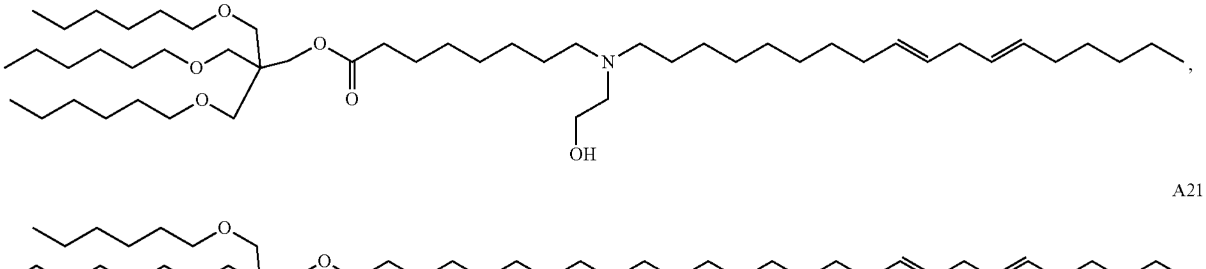
,
A21
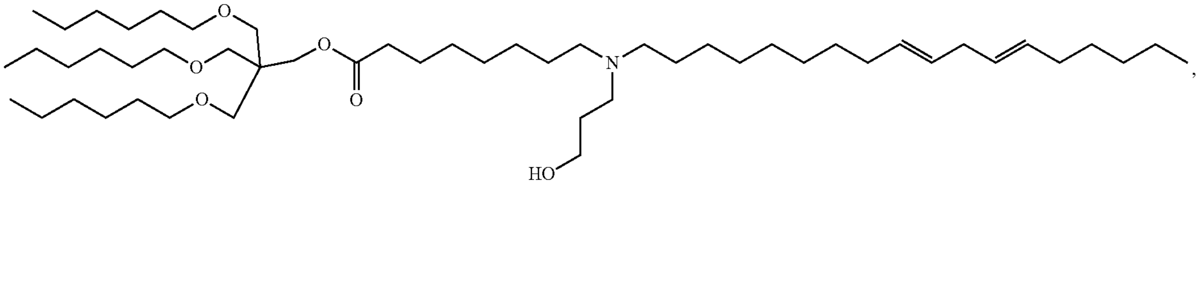
, -continued
A22
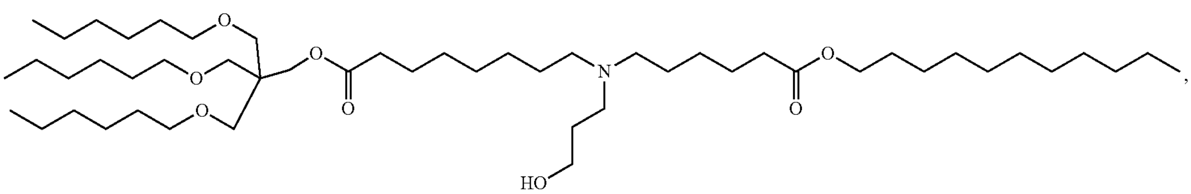
,
A23
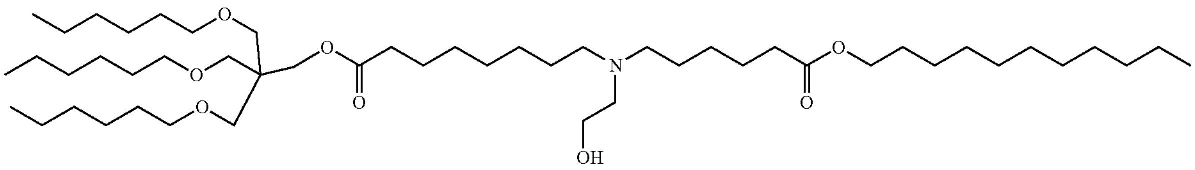
,
A24
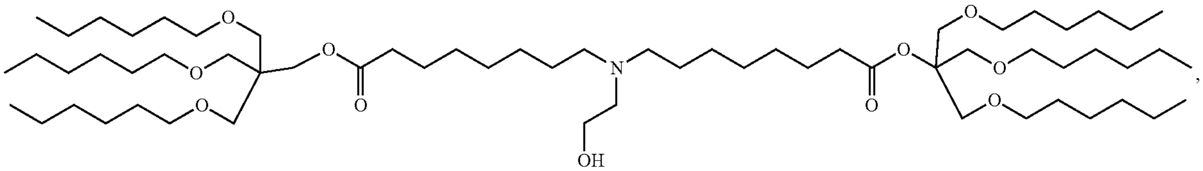
,
A25
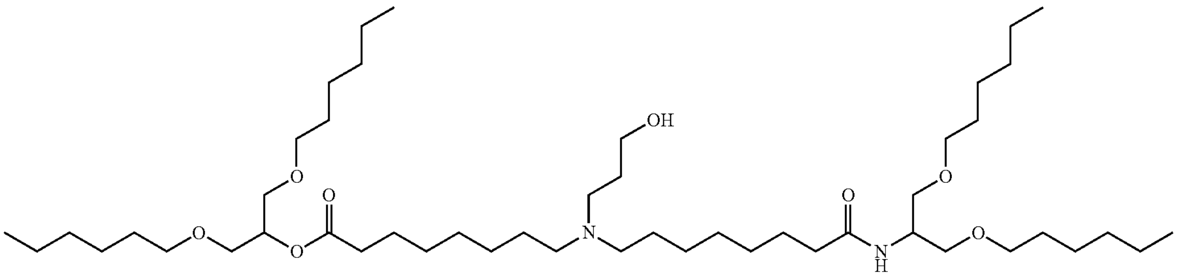
,
A26
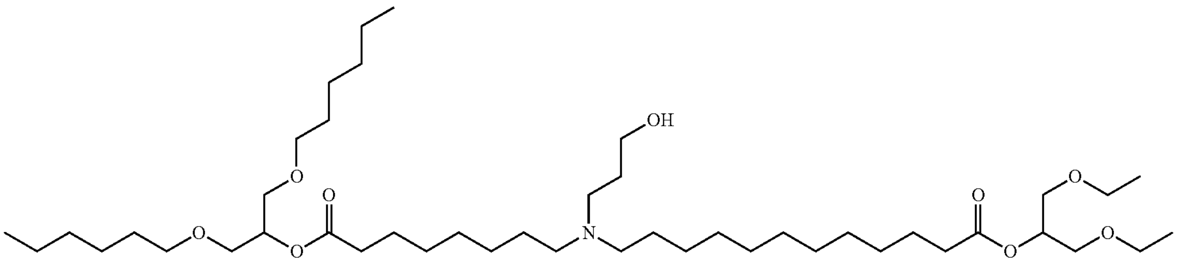
,
A27
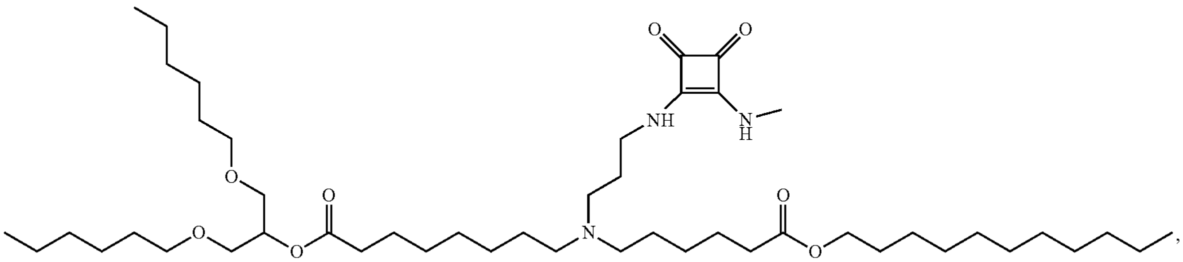
, -continued
A28
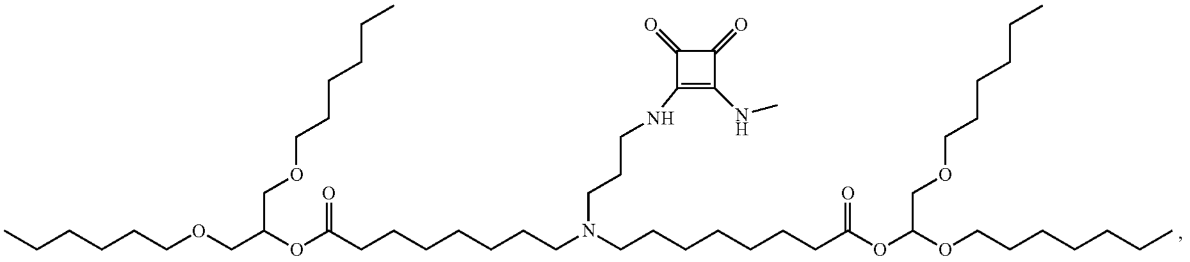
A29
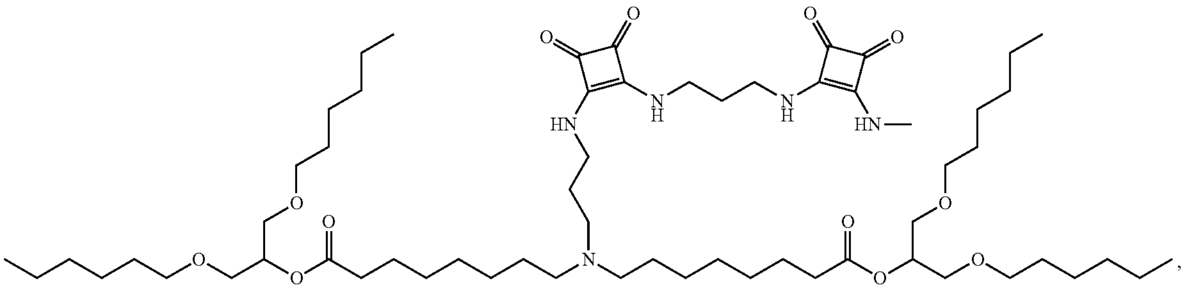
A30
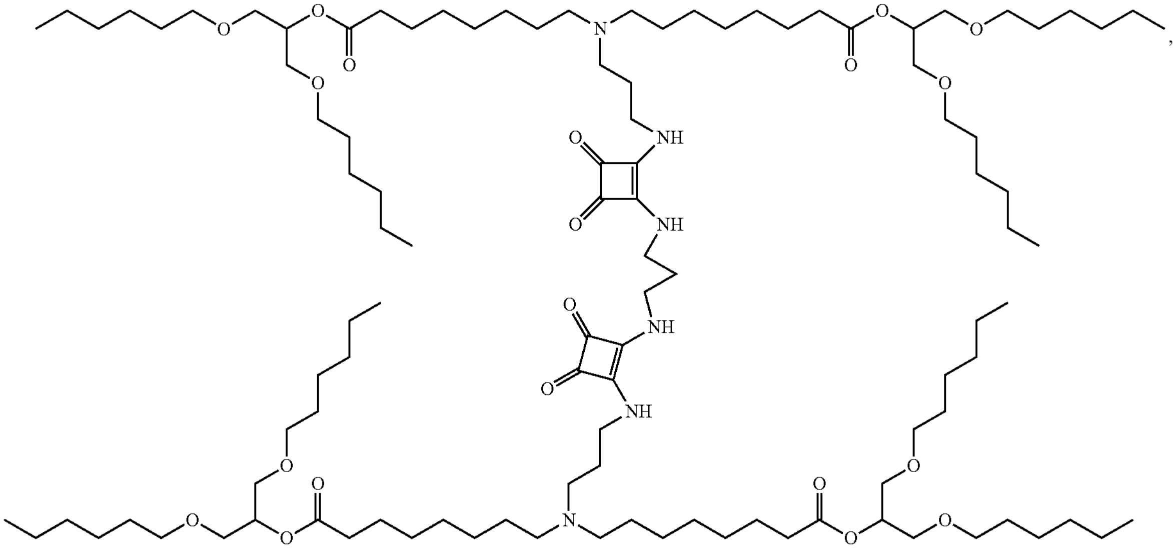
A31
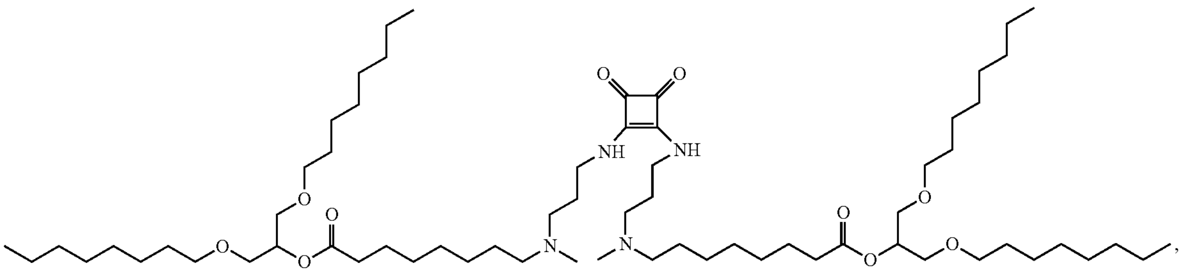

-continued
A32
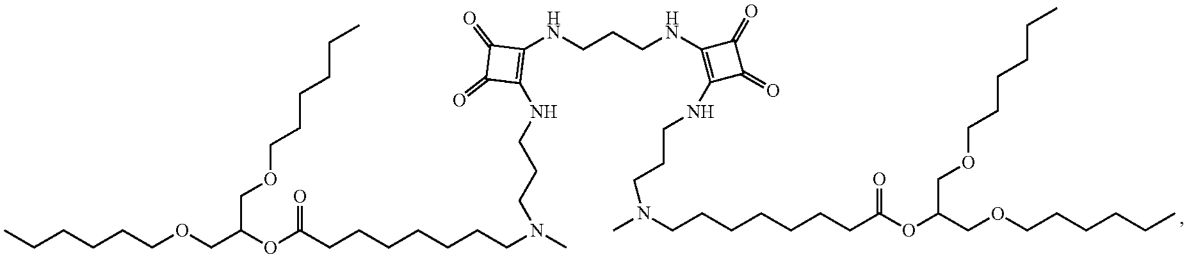
A34
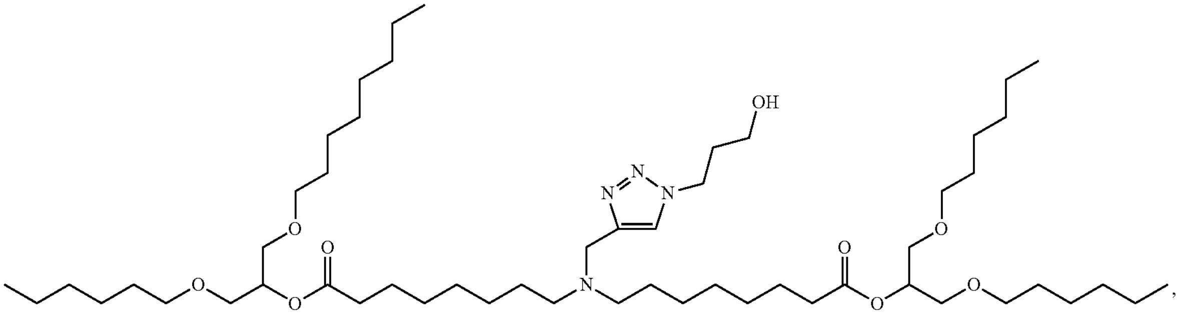
A35
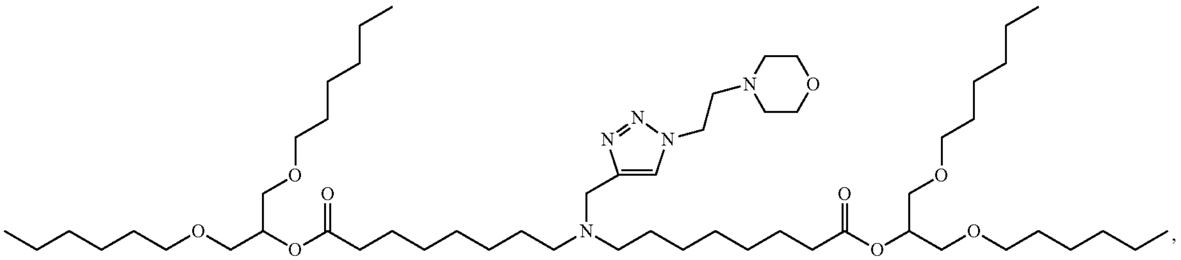
A36
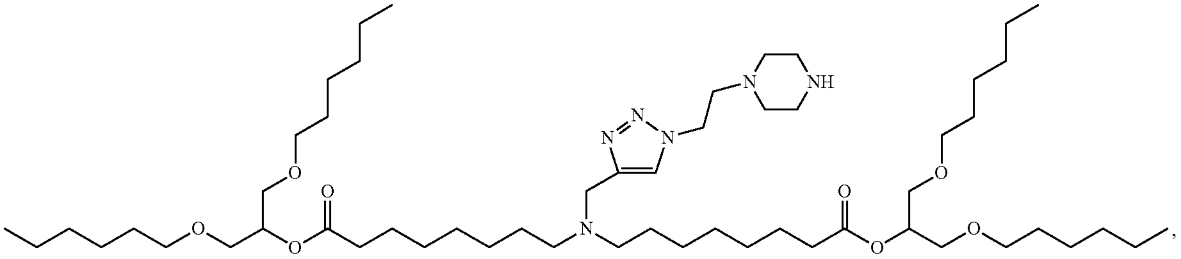
A37
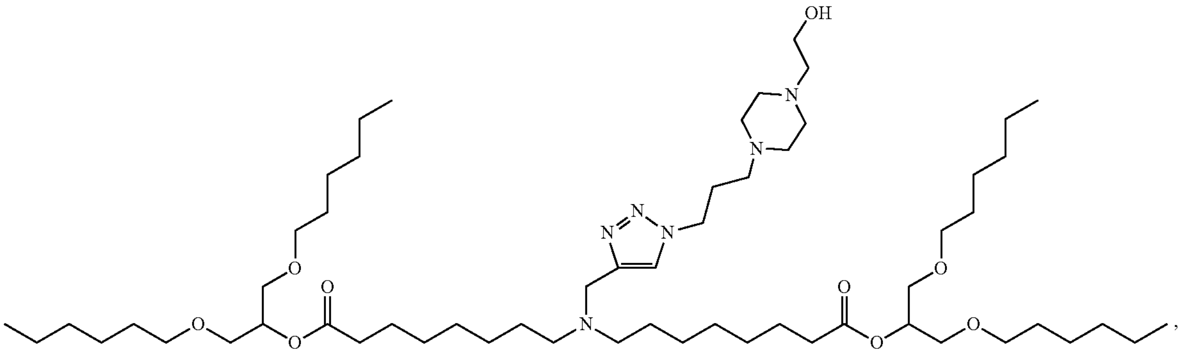

-continued
A38
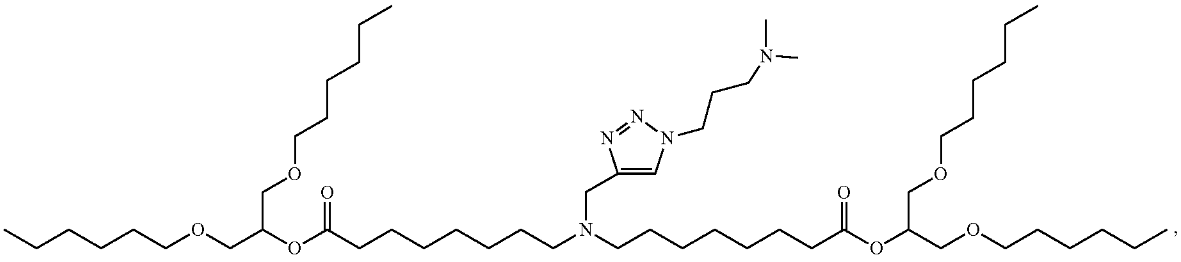
,
A39
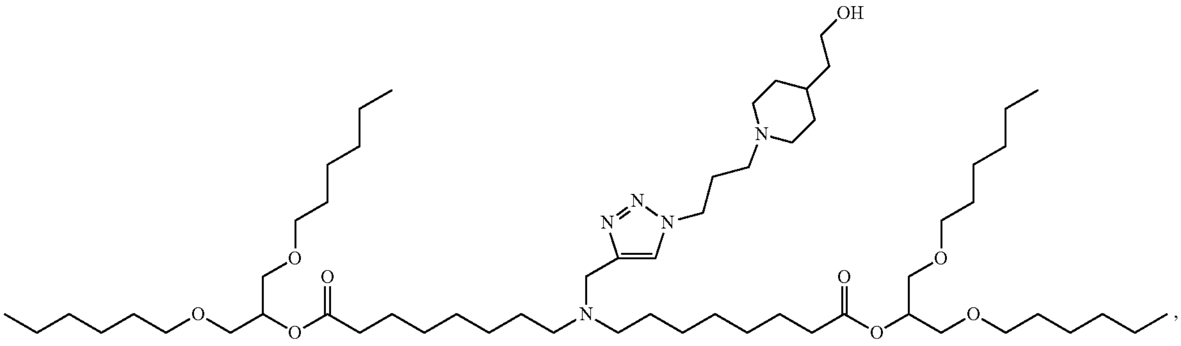
,
A40
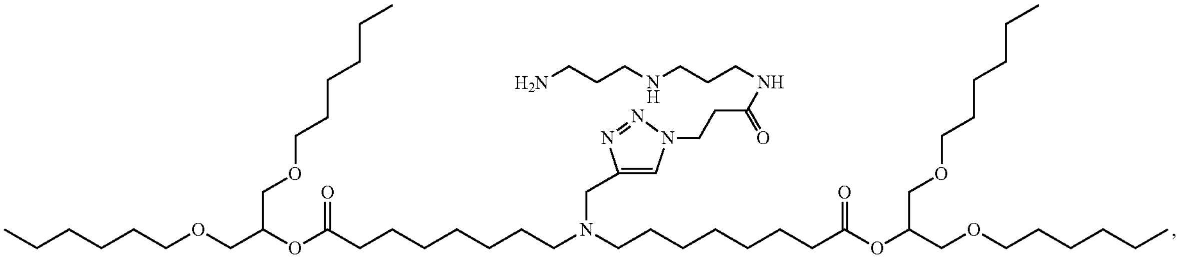
,
A42
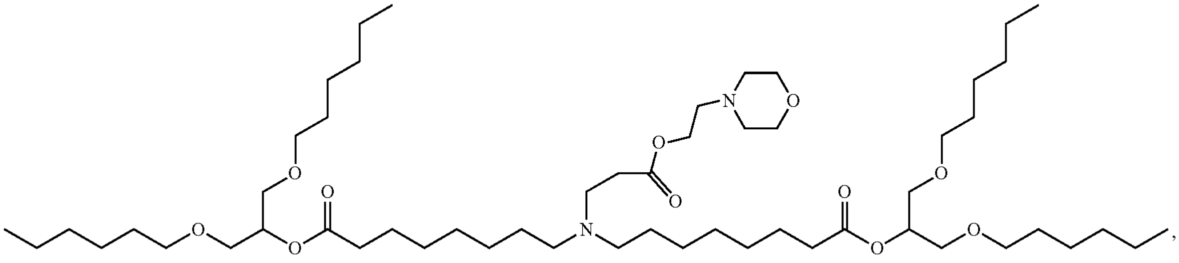
,
A43
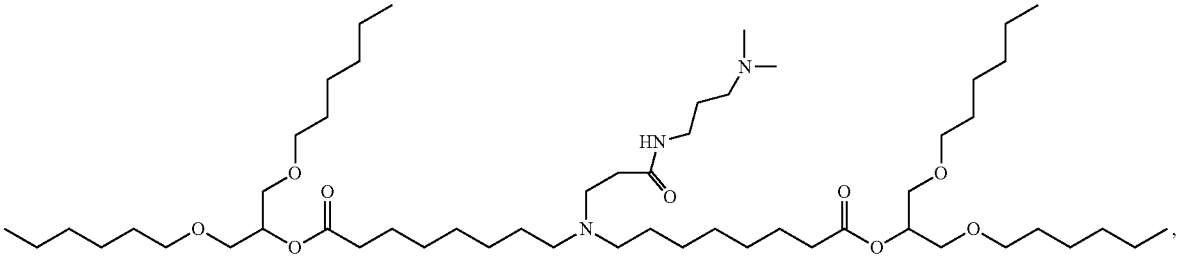
, -continued
A44
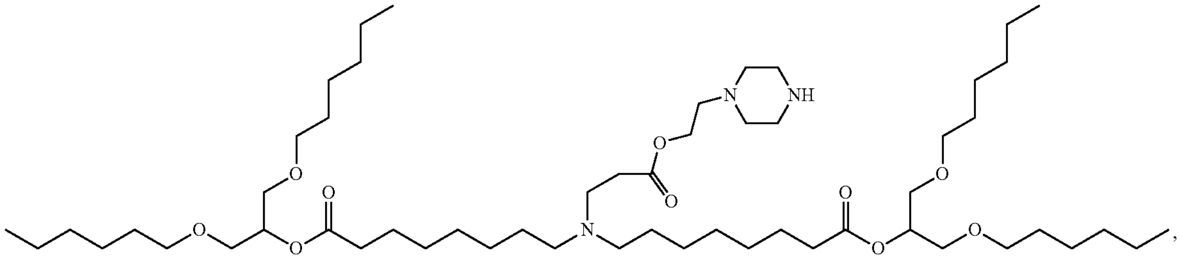
,
A45
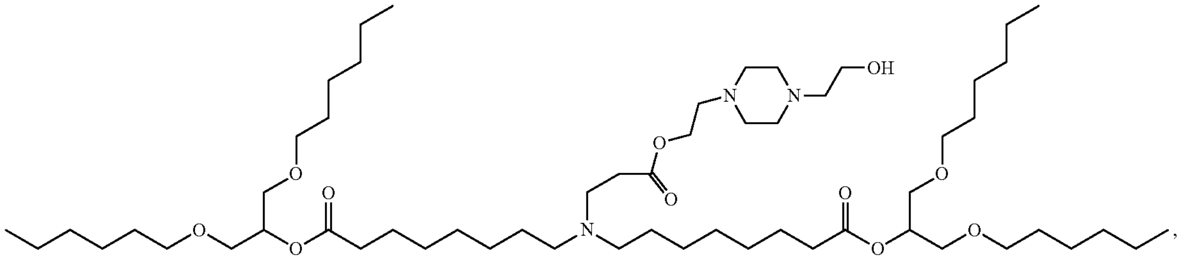
,
A46
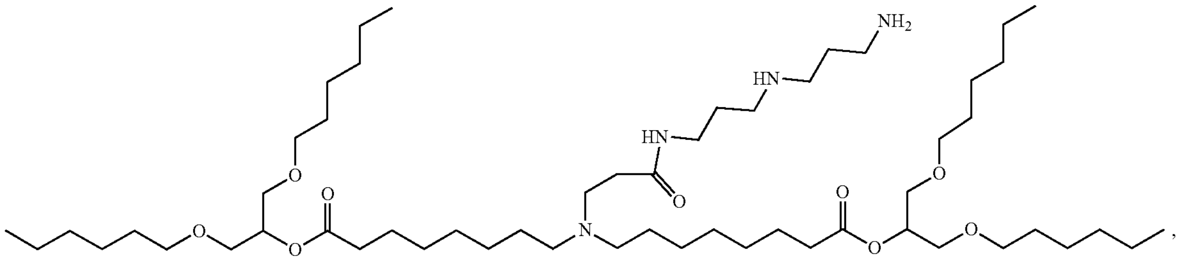
,
A47
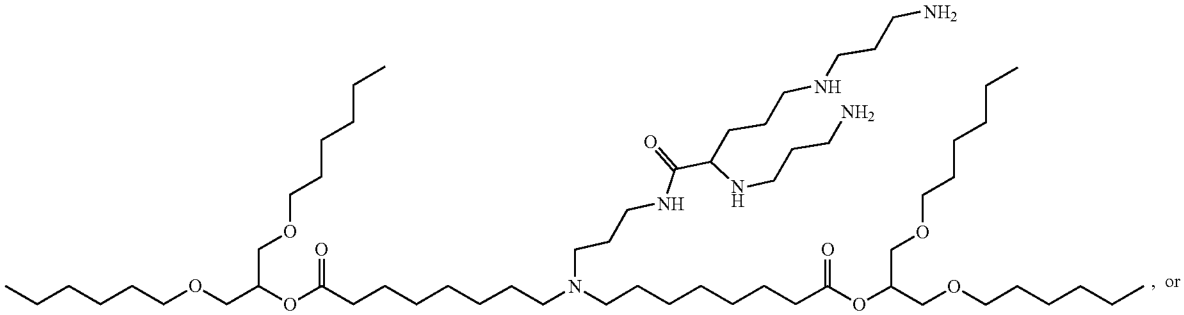
, or
A48
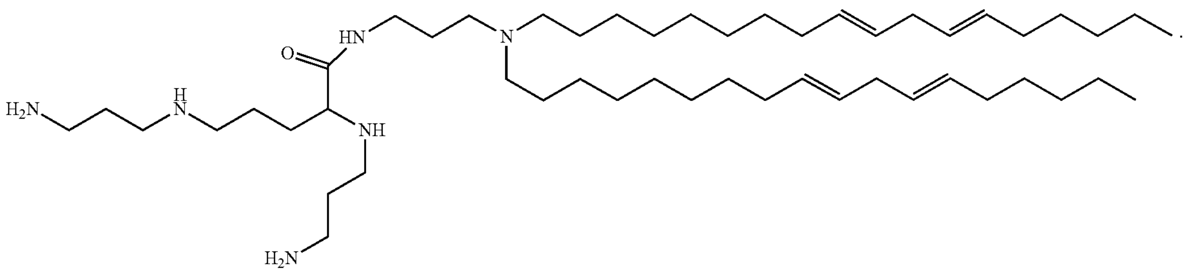
.

6. A composition comprising a compound according to claim 1 as an ionizable lipid compound, and a phospholipid.

7. The composition of claim 6, wherein the phospholipid is selected from at least any one of: 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanol amine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidyethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE), or a combination thereof.

8. The composition of claim 6, further comprising a PEG lipid, which is selected from at least any one of: PEG-modified phosphatidylethanolamine, PEG-modified phosphatidic acid, PEG-modified ceramide, PEG-modified dialkylamine, PEG-modified diacylglycerol, PEG-modified dialkylglycerol, or a combination thereof.

9. The composition of claim 6, further comprising a structural lipid, which is selected from at least any one of: cholesterol, fecosterol, sitosterol, ergosterol, campesterol, stigmasterol, brassicasterol, tomatidine, ursolic acid, alpha-tocopherol, or a combination thereof.

10. The composition of claim 9, wherein the ionizable lipid compound is from 20% to 80%, the PEG lipid is from 1% to 10%, the structural lipid is from 10% to 50% and the phospholipid is from 5% to 30%, each of these percentages being calculated based on mole percentage of all lipids in the composition.

11. The composition of claim 9, wherein the ionizable lipid compound is from 20% to 80%, the PEG lipid is from 1% to 5%, the structural lipid is from 10% to 50% and the phospholipid is from 5% to 30%, each of these percentages being calculated based on mole percentage of all lipids in the composition.

12. The composition of claim 6, further comprising an active ingredient, which is selected from at least any one of: DNA, RNA, protein, or an active pharmaceutical molecule.

13. The composition of claim 12, wherein the active agent is RNA and the RNA is selected from at least any one of: mRNA, siRNA, aiRNA, miRNA, dsRNA, aRNA, or lncRNA.

14. The composition of claim 12, wherein the active agent is a protein which is selected from at least any one of: antibody, enzyme, recombinant protein, polypeptide and short chain polypeptide.

15. The composition of claim 12, wherein:

the composition is in the form of a lipid nanoparticle.

16. A pharmaceutical composition comprising the lipid nanoparticle of claim 15 and a pharmaceutically acceptable carrier.

* * * * *